US012778785B2

(12) United States Patent
Cheng et al.

(10) Patent No.: US 12,778,785 B2
(45) **Date of Patent: *Nov. 3, 2026**

(54) FLUID COLLECTION ASSEMBLIES INCLUDING AT LEAST ONE INFLATION DEVICE AND METHODS AND SYSTEMS OF USING THE SAME

(71) Applicant: PUREWICK CORPORATION, Covington, GA (US)

(72) Inventors: Jason Jishen Cheng, Rochester, NY (US); Eric Rehm, Greensboro, GA (US); Nicholas Austerman, Atlanta, GA (US)

(73) Assignee: PUREWICK CORPORATION, Covington, GA (US)

( * ) Notice: Subject to any disclaimer, the term of this patent is extended or adjusted under 35 U.S.C. 154(b) by 293 days.

This patent is subject to a terminal disclaimer.

(21) Appl. No.: 18/758,025

(22) Filed: Jun. 28, 2024

(65) Prior Publication Data

US 2025/0000686 A1 Jan. 2, 2025

Related U.S. Application Data

(63) Continuation of application No. 17/326,980, filed on May 21, 2021, now Pat. No. 12,048,643.

(Continued)

(51) Int. Cl.

*A61F 5/451* (2006.01)
*A61F 5/44* (2006.01)

(Continued)

(52) U.S. Cl.

CPC ............ *A61F 5/451* (2013.01); *A61F 5/4405* (2013.01); *A61F 5/453* (2013.01); *A61F 5/455* (2013.01); *A61M 1/80* (2021.05)

(58) Field of Classification Search

CPC ........ A61F 5/451; A61F 5/4405; A61F 5/453; A61F 5/455; A61M 1/80

See application file for complete search history.

(56) References Cited

U.S. PATENT DOCUMENTS

| | | | |
|---|---|---|---|
| 737,443 | A | 8/1903 | Mooers |
| 976,883 | A | 11/1910 | Keagy et al. |

(Continued)

FOREIGN PATENT DOCUMENTS

| | | | |
|---|---|---|---|
| AU | 2018216821 | A1 | 8/2019 |
| AU | 2021299304 | A1 | 2/2023 |

(Continued)

OTHER PUBLICATIONS

US 9,908,683 B2, 03/2018, Sandhausen et al. (withdrawn)

(Continued)

*Primary Examiner* — Catharine L Anderson
*Assistant Examiner* — Eric Rassavong
(74) *Attorney, Agent, or Firm* — Ballard Spahr LLP

(57) ABSTRACT

Embodiments disclosed herein are directed to fluid collection assemblies that include at least one inflation device, methods for using the same, and systems including the same. An example fluid collection assembly includes a fluid impermeable barrier defining at least one opening, a chamber, and at least one fluid outlet. The fluid collection assembly also includes at least one porous material disposed in the chamber. The fluid collection assembly further includes at least one inflation device. The inflation device includes at least one bladder having one or more walls defining an interior region. The inflation device also includes at least one valve configured to selectively permit flow of at least one inflation fluid into and out of the interior region to switch the at least one bladder between a first state and a second state.

20 Claims, 8 Drawing Sheets

Related U.S. Application Data

(60) Provisional application No. 63/030,685, filed on May 27, 2020.

(51) Int. Cl.

| | |
|---|---|
| ***A61F 5/453*** | (2006.01) |
| ***A61F 5/455*** | (2006.01) |
| ***A61M 1/00*** | (2006.01) |

(56) References Cited

U.S. PATENT DOCUMENTS 1,015,905 A 1/1912 Northrop
1,032,841 A 7/1912 Koenig
1,178,644 A 4/1916 Johnson
1,229,423 A 6/1917 Eckenrode
1,387,726 A 8/1921 Karge
1,742,080 A 12/1929 Jones
1,979,899 A 11/1934 Obrien et al.
2,241,010 A 5/1941 Chipley
2,262,772 A 11/1941 Peder
2,326,881 A 8/1943 Packer
2,379,346 A 6/1945 Farrell
2,485,555 A 10/1949 Bester
2,571,357 A 10/1951 Charles
2,613,670 A 10/1952 Edward
2,616,426 A 11/1952 Adele
2,644,234 A 7/1953 Ear
2,648,335 A 8/1953 Chambers
2,789,560 A 4/1957 Weimer
2,859,786 A 11/1958 Tupper
2,944,551 A 7/1960 Carl
2,968,046 A 1/1961 Duke
2,971,512 A 2/1961 Reinhardt
3,032,038 A 5/1962 Swinn
3,077,883 A 2/1963 Hill
3,087,938 A 4/1963 Hans et al.
3,089,493 A 5/1963 Galindo
3,114,916 A 12/1963 Hadley
3,169,528 A 2/1965 Knox et al.
3,171,506 A 3/1965 Therkel
3,175,719 A 3/1965 Herndon
3,194,238 A 7/1965 Breece
3,198,994 A 8/1965 Hildebrandt et al.
3,221,742 A 12/1965 Egon
3,312,221 A 4/1967 Overment
3,312,981 A 4/1967 Mcguire et al.
3,340,876 A 9/1967 Hill
3,349,768 A 10/1967 Keane
3,356,091 A 12/1967 Patterson
3,362,590 A 1/1968 Gene
3,366,116 A 1/1968 Huck
3,368,564 A 2/1968 Selix
3,369,940 A 2/1968 Slautterback
3,398,848 A 8/1968 Donovan
3,400,717 A 9/1968 Bruce et al.
3,406,688 A 10/1968 Bruce
3,411,504 A 11/1968 Glassman
3,424,163 A 1/1969 Gravdahl
3,425,471 A 2/1969 Yates
3,434,565 A 3/1969 Fischer
3,447,536 A 6/1969 Snyder
3,511,241 A 5/1970 Lee
3,512,185 A 5/1970 Ellis
3,520,300 A 7/1970 Flower
3,528,423 A 9/1970 Lee
3,608,552 A 9/1971 Broerman
3,613,123 A 10/1971 Langstrom
3,648,700 A 3/1972 Warner
3,651,810 A 3/1972 Ormerod
3,661,155 A 5/1972 Lindan
3,683,918 A 8/1972 Pizzella
3,690,315 A 9/1972 Chittenden et al.
3,699,815 A 10/1972 Holbrook
3,720,554 A 3/1973 Stumpf
3,721,243 A 3/1973 Greth et al.
3,726,277 A 4/1973 Hirschman
3,727,788 A 4/1973 Holbrook
3,730,411 A 5/1973 Brockmuller
3,742,952 A * 7/1973 Magers ................ A61M 1/684
604/133
3,742,953 A 7/1973 Lee
3,757,355 A 9/1973 Allen et al.
3,788,324 A 1/1974 Lim
3,843,016 A 10/1974 Bornhorst et al.
3,863,638 A 2/1975 Rogers et al.
3,863,798 A 2/1975 Kurihara et al.
3,864,759 A 2/1975 Horiuchi
3,865,109 A 2/1975 Elmore et al.
3,881,486 A 5/1975 Fenton
3,881,489 A 5/1975 Hartwell
3,887,032 A 6/1975 Harris
3,915,189 A 10/1975 Holbrook et al.
3,931,650 A 1/1976 Miller
3,931,819 A 1/1976 Weedle
3,964,786 A 6/1976 Mashuda
3,998,228 A 12/1976 Poidomani
3,999,550 A 12/1976 Martin
4,006,793 A 2/1977 Robinson
4,015,604 A 4/1977 Csillag
4,020,843 A 5/1977 Kanall
4,022,211 A 5/1977 Timmons et al.
4,022,213 A 5/1977 Stein
4,023,216 A 5/1977 Li
4,027,776 A 6/1977 Douglas
4,031,897 A 6/1977 Graetz
4,042,337 A 8/1977 Griffith
4,064,962 A 12/1977 Hunt
4,069,817 A 1/1978 Fenole et al.
4,084,589 A 4/1978 Kulvi
4,096,897 A 6/1978 Cammarata, III
4,116,197 A 9/1978 Bermingham
4,117,845 A 10/1978 Brown
4,140,739 A 2/1979 Cotten
4,180,178 A 12/1979 Turner
4,187,953 A 2/1980 Turner
4,194,508 A 3/1980 Anderson
4,197,849 A 4/1980 Bostick
4,200,102 A 4/1980 Duhamel et al.
4,202,058 A 5/1980 Anderson
4,203,502 A 5/1980 Strader
4,203,503 A 5/1980 Bertotti et al.
4,209,076 A 6/1980 Bertotti et al.
D255,935 S 7/1980 Cullis et al.
4,223,677 A 9/1980 Anderson
4,233,025 A 11/1980 Larson et al.
4,233,978 A 11/1980 Hickey
4,246,901 A 1/1981 Frosch et al.
4,253,542 A 3/1981 Ruspa et al.
4,257,418 A 3/1981 Hessner
4,270,539 A 6/1981 Frosch et al.
4,280,498 A 7/1981 Jensen
4,281,655 A 8/1981 Terauchi
4,292,916 A 10/1981 Bradley et al.
4,330,239 A 5/1982 Gannaway
4,345,341 A 8/1982 Saito
4,349,029 A 9/1982 Mott
4,352,356 A 10/1982 Tong
4,356,012 A 10/1982 Hofstetter
4,360,933 A 11/1982 Kimura et al.
4,365,363 A 12/1982 Windauer
4,372,299 A 2/1983 Fixel
4,375,841 A 3/1983 Vielbig
4,387,726 A 6/1983 Denard
4,403,991 A 9/1983 Hill
4,421,511 A 12/1983 Steer et al.
4,425,130 A 1/1984 Desmarais
4,446,986 A 5/1984 Bowen et al.
4,453,938 A 6/1984 Brendling
4,457,314 A 7/1984 Knowles
4,457,758 A 7/1984 Norton
4,476,879 A 10/1984 Jackson
4,512,771 A 4/1985 Norton
4,526,688 A 7/1985 Schmidt et al.
4,528,703 A 7/1985 Kraus

(56) References Cited

U.S. PATENT DOCUMENTS

| | | | |
|---|---|---|---|
| 4,533,354 | A | 8/1985 | Jensen |
| 4,533,357 | A | 8/1985 | Hall |
| D280,438 | S | 9/1985 | Wendt |
| 4,551,141 | A | 11/1985 | Mcneil |
| 4,553,968 | A | 11/1985 | Komis |
| 4,568,341 | A | 2/1986 | Mitchell et al. |
| 4,581,026 | A | 4/1986 | Schneider |
| 4,583,983 | A | 4/1986 | Einhorn et al. |
| 4,589,516 | A | 5/1986 | Inoue et al. |
| 4,601,716 | A | 7/1986 | Smith |
| 4,610,675 | A | 9/1986 | Triunfol |
| 4,620,333 | A | 11/1986 | Ritter |
| 4,626,250 | A | 12/1986 | Schneider |
| 4,627,846 | A | 12/1986 | Ternstroem |
| 4,631,061 | A | 12/1986 | Martin |
| 4,645,275 | A | 2/1987 | Pucci |
| 4,650,477 | A | 3/1987 | Johnson |
| 4,655,754 | A | 4/1987 | Richmond et al. |
| 4,656,675 | A | 4/1987 | Fajnsztajn |
| 4,681,570 | A | 7/1987 | Dalton |
| 4,681,572 | A | 7/1987 | Tokarz et al. |
| 4,681,577 | A | 7/1987 | Stern et al. |
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |
| 4,723,953 | A | 2/1988 | Pratt et al. |
| 4,735,841 | A | 4/1988 | Sourdet |
| 4,743,236 | A | 5/1988 | Manschot |
| 4,747,166 | A | 5/1988 | Kuntz |
| 4,752,944 | A | 6/1988 | Conrads et al. |
| 4,759,753 | A | 7/1988 | Schneider et al. |
| 4,769,215 | A | 9/1988 | Ehrenkranz |
| 4,771,484 | A | 9/1988 | Mozell |
| 4,772,280 | A | 9/1988 | Rooyakkers |
| 4,775,458 | A | 10/1988 | Forester |
| 4,784,654 | A | 11/1988 | Beecher |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,813,943 | A | 3/1989 | Smith |
| 4,820,291 | A | 4/1989 | Terauchi et al. |
| 4,820,297 | A | 4/1989 | Kaufman et al. |
| 4,841,728 | A | 6/1989 | Jean et al. |
| 4,846,818 | A | 7/1989 | Keldahl et al. |
| 4,846,819 | A | 7/1989 | Welch |
| 4,846,824 | A | 7/1989 | Lassen et al. |
| 4,846,909 | A | 7/1989 | Klug et al. |
| 4,857,064 | A | 8/1989 | Mendoza |
| 4,865,595 | A | 9/1989 | Heyden |
| 4,872,299 | A | 10/1989 | Troutner et al. |
| 4,875,898 | A | 10/1989 | Eakin |
| 4,880,417 | A | 11/1989 | Yabrov et al. |
| 4,882,794 | A | 11/1989 | Stewart |
| 4,883,465 | A | 11/1989 | Brennan |
| 4,886,498 | A | 12/1989 | Newton |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,890,691 | A | 1/1990 | Ching-ho |
| 4,895,140 | A | 1/1990 | Bellak |
| 4,903,254 | A | 2/1990 | Haas |
| 4,904,248 | A | 2/1990 | Vaillancourt |
| D306,759 | S | 3/1990 | D'Alo |
| 4,905,692 | A | 3/1990 | More |
| 4,911,262 | A | 3/1990 | Tani et al. |
| 4,930,997 | A | 6/1990 | Bennett |
| 4,936,838 | A | 6/1990 | Cross et al. |
| 4,950,262 | A | 8/1990 | Takagi |
| 4,955,922 | A | 9/1990 | Terauchi |
| 4,957,487 | A | 9/1990 | Gerow |
| 4,963,134 | A | 10/1990 | Backscheider et al. |
| 4,965,460 | A | 10/1990 | Tanaka et al. |
| 4,986,823 | A | 1/1991 | Anderson et al. |
| 4,987,849 | A | 1/1991 | Sherman |
| 5,002,541 | A | 3/1991 | Conkling et al. |
| 5,004,463 | A | 4/1991 | Nigay |
| 5,013,308 | A | 5/1991 | Sullivan et al. |
| 5,030,229 | A | 7/1991 | Yang |
| 5,031,248 | A | 7/1991 | Kemper |
| 5,045,077 | A | 9/1991 | Blake |
| 5,045,283 | A | 9/1991 | Patel |
| 5,049,144 | A | 9/1991 | Payton |
| 5,053,339 | A | 10/1991 | Patel |
| 5,057,092 | A | 10/1991 | Webster |
| 5,058,088 | A | 10/1991 | Haas et al. |
| 5,071,347 | A | 12/1991 | Mcguire |
| 5,078,707 | A | 1/1992 | Peter |
| 5,084,037 | A | 1/1992 | Barnett |
| 5,100,396 | A | 3/1992 | Zamierowski |
| 5,102,404 | A | 4/1992 | Goldberg et al. |
| 5,112,324 | A | 5/1992 | Wallace |
| 5,134,994 | A | 8/1992 | Say |
| 5,137,033 | A | 8/1992 | Norton |
| 5,147,301 | A | 9/1992 | Ruvio |
| 5,176,667 | A | 1/1993 | Debring |
| 5,195,997 | A | 3/1993 | Carns |
| 5,196,654 | A | 3/1993 | Diflora et al. |
| 5,199,444 | A | 4/1993 | Wheeler |
| 5,203,699 | A | 4/1993 | Mcguire |
| 5,220,137 | A | 6/1993 | Howerton et al. |
| 5,234,419 | A | 8/1993 | Bryant et al. |
| 5,244,458 | A | 9/1993 | Takasu |
| 5,246,454 | A | 9/1993 | Peterson |
| 5,267,988 | A | 12/1993 | Farkas |
| 5,275,307 | A | 1/1994 | Freese |
| 5,282,795 | A | 2/1994 | Finney |
| 5,295,979 | A | 3/1994 | DeLaurentis et al. |
| 5,295,983 | A | 3/1994 | Kubo |
| 5,300,052 | A | 4/1994 | Kubo |
| 5,304,749 | A | 4/1994 | Crandell |
| 5,312,383 | A | 5/1994 | Kubalak |
| 5,318,550 | A | 6/1994 | Cermak et al. |
| 5,330,457 | A | 7/1994 | Cohen |
| 5,330,459 | A | 7/1994 | Lavon et al. |
| 5,334,174 | A | 8/1994 | Street |
| 5,334,176 | A | 8/1994 | Buenger et al. |
| 5,340,840 | A | 8/1994 | Park et al. |
| D354,129 | S | 1/1995 | Salvadori |
| D354,560 | S | 1/1995 | Chase |
| 5,382,244 | A | 1/1995 | Telang |
| 5,397,315 | A | 3/1995 | Schmidt et al. |
| 5,409,014 | A | 4/1995 | Napoli et al. |
| 5,409,475 | A | 4/1995 | Steer |
| 5,411,495 | A | 5/1995 | Willingham |
| 5,423,784 | A | 6/1995 | Metz |
| 5,423,788 | A | 6/1995 | Rollins et al. |
| 5,437,836 | A | 8/1995 | Yamada |
| 5,455,091 | A | 10/1995 | Oreglia et al. |
| 5,456,246 | A | 10/1995 | Schmieding et al. |
| 5,466,229 | A | 11/1995 | Elson et al. |
| 5,478,334 | A | 12/1995 | Bernstein |
| 5,499,977 | A | 3/1996 | Marx |
| 5,525,407 | A | 6/1996 | Yang |
| 5,543,042 | A | 8/1996 | Filan et al. |
| D373,928 | S | 9/1996 | Green |
| 5,582,604 | A | 12/1996 | Ahr et al. |
| 5,592,950 | A | 1/1997 | Kopelowicz |
| 5,593,389 | A | 1/1997 | Chang |
| 5,605,161 | A | 2/1997 | Cross |
| 5,614,699 | A | 3/1997 | Yashiro et al. |
| 5,618,277 | A | 4/1997 | Goulter |
| 5,628,735 | A | 5/1997 | Skow |
| 5,632,736 | A | 5/1997 | Block |
| 5,636,643 | A | 6/1997 | Argenta et al. |
| 5,637,104 | A | 6/1997 | Ball et al. |
| 5,641,277 | A | 6/1997 | Gondek |
| D380,543 | S | 7/1997 | Piontek et al. |

(56) References Cited

U.S. PATENT DOCUMENTS

| | | | |
|---|---|---|---|
| 5,662,633 | A | 9/1997 | Doak et al. |
| 5,674,212 | A | 10/1997 | Osborn et al. |
| 5,678,564 | A | 10/1997 | Lawrence et al. |
| 5,681,297 | A | 10/1997 | Hashimoto et al. |
| 5,687,429 | A | 11/1997 | Rahlff |
| 5,695,485 | A | 12/1997 | Duperret et al. |
| 5,695,487 | A | 12/1997 | Cohen et al. |
| 5,700,254 | A | 12/1997 | Mcdowall et al. |
| 5,701,612 | A | 12/1997 | Daneshvar |
| 5,705,777 | A | 1/1998 | Flanigan et al. |
| 5,735,835 | A | 4/1998 | Holland |
| 5,735,837 | A | 4/1998 | Ishikawa |
| 5,752,944 | A | 5/1998 | Dann et al. |
| 5,763,333 | A | 6/1998 | Suzuki et al. |
| 5,772,644 | A | 6/1998 | Bark et al. |
| 5,792,132 | A | 8/1998 | Garcia |
| 5,827,243 | A | 10/1998 | Palestrant |
| 5,827,247 | A | 10/1998 | Kay |
| 5,827,250 | A | 10/1998 | Fujioka et al. |
| 5,827,257 | A | 10/1998 | Fujioka et al. |
| D401,699 | S | 11/1998 | Herchenbach et al. |
| 5,859,393 | A | 1/1999 | Cummins et al. |
| 5,865,378 | A | 2/1999 | Hollinshead et al. |
| 5,873,869 | A | 2/1999 | Hammons et al. |
| 5,876,393 | A | 3/1999 | Ahr et al. |
| 5,887,291 | A | 3/1999 | Bellizzi |
| 5,891,125 | A | 4/1999 | Plumley |
| 5,894,608 | A | 4/1999 | Birbara |
| 5,895,349 | A | 4/1999 | Tihon |
| D409,303 | S | 5/1999 | Oepping |
| 5,911,222 | A | 6/1999 | Lawrence et al. |
| 5,956,782 | A | 9/1999 | Olguin |
| 5,957,904 | A | 9/1999 | Holland |
| 5,968,026 | A | 10/1999 | Osborn et al. |
| 5,972,505 | A | 10/1999 | Phillips et al. |
| 5,984,045 | A | 11/1999 | Maeda et al. |
| 6,007,524 | A | 12/1999 | Schneider |
| 6,007,526 | A | 12/1999 | Passalaqua et al. |
| D421,307 | S | 2/2000 | Harmanoglu |
| 6,039,060 | A | 3/2000 | Rower |
| 6,050,983 | A | 4/2000 | Moore et al. |
| 6,059,762 | A | 5/2000 | Boyer et al. |
| 6,061,905 | A | 5/2000 | Logic |
| 6,063,064 | A | 5/2000 | Tuckey et al. |
| 6,068,477 | A | 5/2000 | Mahlmann |
| 6,083,602 | A | 7/2000 | Caldwell et al. |
| 6,098,625 | A | 8/2000 | Winkler |
| 6,105,174 | A | 8/2000 | Karlsten et al. |
| 6,113,582 | A | 9/2000 | Dwork |
| 6,117,163 | A | 9/2000 | Bierman |
| 6,123,398 | A | 9/2000 | Arai et al. |
| 6,129,718 | A | 10/2000 | Wada et al. |
| 6,131,964 | A | 10/2000 | Sareshwala |
| 6,152,902 | A | 11/2000 | Christian et al. |
| 6,164,569 | A | 12/2000 | Hollinshead et al. |
| 6,177,606 | B1 | 1/2001 | Etheredge et al. |
| 6,209,142 | B1 | 4/2001 | Mattsson et al. |
| 6,220,050 | B1 | 4/2001 | Cooksey |
| 6,244,311 | B1 | 6/2001 | Hand et al. |
| 6,248,096 | B1 | 6/2001 | Dwork et al. |
| 6,263,887 | B1 | 7/2001 | Dunn |
| 6,283,246 | B1 | 9/2001 | Nishikawa |
| 6,296,627 | B1 | 10/2001 | Edwards |
| 6,311,339 | B1 | 11/2001 | Kraus |
| 6,316,688 | B1 | 11/2001 | Hammons et al. |
| 6,336,919 | B1 | 1/2002 | Davis et al. |
| 6,338,729 | B1 | 1/2002 | Wada et al. |
| 6,352,525 | B1 | 3/2002 | Wakabayashi |
| 6,394,988 | B1 | 5/2002 | Hashimoto |
| 6,395,956 | B1 | 5/2002 | Glasgow et al. |
| 6,398,742 | B1 | 6/2002 | Kim |
| 6,406,463 | B1 | 6/2002 | Brown |
| 6,409,712 | B1 | 6/2002 | Dutari et al. |
| 6,415,888 | B2 | 7/2002 | An et al. |
| 6,416,500 | B1 | 7/2002 | Wada et al. |
| 6,417,750 | B1 | 7/2002 | Sohn |
| 6,423,045 | B1 | 7/2002 | Wise et al. |
| 6,428,521 | B1 | 8/2002 | Droll |
| 6,428,522 | B1 | 8/2002 | Dipalma et al. |
| 6,446,454 | B1 | 9/2002 | Lee et al. |
| 6,461,340 | B1 | 10/2002 | Lenker et al. |
| 6,467,570 | B1 | 10/2002 | Herold |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,524,292 | B1 | 2/2003 | Dipalma et al. |
| 6,526,603 | B1 | 3/2003 | Murphy |
| 6,540,729 | B1 | 4/2003 | Wada et al. |
| 6,547,771 | B2 | 4/2003 | Robertson et al. |
| 6,551,293 | B1 | 4/2003 | Mitchell |
| 6,569,133 | B2 | 5/2003 | Cheng et al. |
| 6,571,910 | B2 | 6/2003 | Storm |
| D476,518 | S | 7/2003 | Doppelt |
| 6,592,560 | B2 | 7/2003 | Snyder et al. |
| 6,610,038 | B1 | 8/2003 | Dipalma et al. |
| 6,618,868 | B2 | 9/2003 | Minnick |
| 6,620,142 | B1 | 9/2003 | Flueckiger |
| 6,629,651 | B1 | 10/2003 | Male et al. |
| 6,635,037 | B1 | 10/2003 | Bennett |
| 6,635,038 | B2 | 10/2003 | Scovel |
| 6,652,495 | B1 | 11/2003 | Walker |
| 6,666,850 | B1 | 12/2003 | Ahr et al. |
| 6,685,684 | B1 | 2/2004 | Falconer |
| 6,695,828 | B1 | 2/2004 | Dipalma et al. |
| 6,699,174 | B1 | 3/2004 | Bennett |
| 6,700,034 | B1 | 3/2004 | Lindsay et al. |
| 6,702,793 | B1 | 3/2004 | Sweetser et al. |
| 6,706,027 | B2 | 3/2004 | Harvie et al. |
| 6,732,384 | B2 | 5/2004 | Scott |
| 6,736,977 | B1 | 5/2004 | Hall et al. |
| 6,740,066 | B2 | 5/2004 | Wolff et al. |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,848,719 | B2 | 2/2005 | Rowley |
| 6,849,065 | B2 | 2/2005 | Schmidt et al. |
| 6,857,137 | B2 | 2/2005 | Otto |
| 6,878,647 | B1 | 4/2005 | Rezai et al. |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 | 7/2005 | Harvie |
| 6,979,324 | B2 | 12/2005 | Bybordi et al. |
| 7,018,366 | B2 | 3/2006 | Easter |
| 7,018,367 | B2 | 3/2006 | Nava |
| 7,066,411 | B2 | 6/2006 | Male et al. |
| 7,087,043 | B2 | 8/2006 | Dolan |
| 7,122,023 | B1 | 10/2006 | Hinoki |
| 7,125,399 | B2 | 10/2006 | Miskie |
| 7,131,964 | B2 | 11/2006 | Harvie |
| 7,135,012 | B2 | 11/2006 | Harvie |
| 7,141,043 | B2 | 11/2006 | Harvie |
| D533,972 | S | 12/2006 | La |
| 7,160,273 | B2 | 1/2007 | Greter et al. |
| 7,166,092 | B2 | 1/2007 | Elson et al. |
| 7,171,699 | B2 | 2/2007 | Ernest et al. |
| 7,171,871 | B2 | 2/2007 | Kozak |
| 7,179,951 | B2 | 2/2007 | Krishnaswamy-mirle et al. |
| 7,181,781 | B1 | 2/2007 | Trabold et al. |
| 7,186,245 | B1 | 3/2007 | Cheng et al. |
| 7,192,424 | B2 | 3/2007 | Cooper |
| 7,219,764 | B1 | 5/2007 | Forbes |
| 7,220,250 | B2 | 5/2007 | Suzuki et al. |
| D562,975 | S | 2/2008 | Otto |
| 7,335,189 | B2 | 2/2008 | Harvie |
| 7,347,691 | B1 | 3/2008 | Kelly |
| 7,358,282 | B2 | 4/2008 | Krueger et al. |
| 7,390,320 | B2 | 6/2008 | Machida et al. |
| 7,438,706 | B2 | 10/2008 | Koizumi et al. |
| 7,488,310 | B2 | 2/2009 | Yang |
| 7,491,194 | B1 | 2/2009 | Oliwa |

(56) References Cited

U.S. PATENT DOCUMENTS

| | | | |
|---|---|---|---|
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,549,511 | B2 | 6/2009 | Marocco |
| 7,549,512 | B2 | 6/2009 | Newberry |
| 7,585,293 | B2 | 9/2009 | Vermaak |
| 7,588,560 | B1 | 9/2009 | Dunlop |
| 7,637,905 | B2 | 12/2009 | Saadat et al. |
| 7,658,730 | B2 | 2/2010 | Conley |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 | 4/2010 | Bengtson et al. |
| 7,700,819 | B2 | 4/2010 | Ambrosio et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| 7,803,144 | B1 | 9/2010 | Vollrath |
| D625,407 | S | 10/2010 | Koizumi et al. |
| 7,806,879 | B2 | 10/2010 | Brooks et al. |
| 7,811,272 | B2 | 10/2010 | Lindsay et al. |
| 7,815,067 | B2 | 10/2010 | Matsumoto et al. |
| 7,833,169 | B2 | 11/2010 | Hannon |
| 7,857,806 | B2 | 12/2010 | Karpowicz et al. |
| 7,866,942 | B2 | 1/2011 | Harvie |
| 7,871,385 | B2 | 1/2011 | Levinson et al. |
| 7,875,010 | B2 | 1/2011 | Frazier et al. |
| 7,901,389 | B2 | 3/2011 | Mombrinie |
| 7,927,320 | B2 | 4/2011 | Goldwasser et al. |
| 7,927,321 | B2 | 4/2011 | Marland |
| 7,931,634 | B2 | 4/2011 | Swiecicki et al. |
| 7,939,706 | B2 | 5/2011 | Okabe et al. |
| 7,946,443 | B2 | 5/2011 | Stull et al. |
| 7,947,025 | B2 | 5/2011 | Buglino et al. |
| 7,963,419 | B2 | 6/2011 | Burney et al. |
| 7,976,519 | B2 | 7/2011 | Bubb et al. |
| 7,981,087 | B2 | 7/2011 | Gesler, III |
| 7,993,318 | B2 | 8/2011 | Olsson et al. |
| 8,015,627 | B2 | 9/2011 | Baker et al. |
| 8,016,071 | B1 | 9/2011 | Martinus et al. |
| 8,028,460 | B2 | 10/2011 | Williams |
| 8,047,398 | B2 | 11/2011 | Dimartino et al. |
| 8,075,538 | B2 | 12/2011 | Vernon |
| 8,083,026 | B1 | 12/2011 | Butler |
| 8,083,094 | B2 | 12/2011 | Caulfield et al. |
| 8,128,608 | B2 | 3/2012 | Thevenin |
| 8,156,941 | B1 | 4/2012 | Simms |
| 8,167,860 | B1 | 5/2012 | Siegel |
| 8,181,651 | B2 | 5/2012 | Pinel |
| 8,181,819 | B2 | 5/2012 | Burney et al. |
| 8,211,063 | B2 | 7/2012 | Bierman et al. |
| 8,221,369 | B2 | 7/2012 | Parks et al. |
| 8,241,262 | B2 | 8/2012 | Mahnensmith |
| 8,277,426 | B2 | 10/2012 | Wilcox et al. |
| 8,287,508 | B1 | 10/2012 | Sanchez |
| 8,303,554 | B2 | 11/2012 | Tsai et al. |
| 8,322,565 | B2 | 12/2012 | Caulfield et al. |
| 8,337,477 | B2 | 12/2012 | Parks et al. |
| D674,241 | S | 1/2013 | Bickert et al. |
| 8,343,122 | B2 | 1/2013 | Gorres |
| 8,343,125 | B2 | 1/2013 | Kawazoe et al. |
| 8,353,074 | B2 | 1/2013 | Krebs |
| 8,353,886 | B2 | 1/2013 | Bester et al. |
| D676,241 | S | 2/2013 | Merrill |
| 8,388,587 | B1 | 3/2013 | Gmuer et al. |
| 8,388,588 | B2 | 3/2013 | Wada et al. |
| D679,807 | S | 4/2013 | Burgess et al. |
| 8,425,482 | B2 | 4/2013 | Khoubnazar |
| 8,430,855 | B2 | 4/2013 | Burgess et al. |
| 8,434,586 | B2 | 5/2013 | Pawelski et al. |
| 8,449,510 | B2 | 5/2013 | Martini et al. |
| D684,260 | S | 6/2013 | Lund et al. |
| 8,470,230 | B2 | 6/2013 | Caulfield et al. |
| 8,479,941 | B2 | 7/2013 | Matsumoto et al. |
| 8,479,949 | B2 | 7/2013 | Henkel |
| 8,500,719 | B1 | 8/2013 | Simpson et al. |
| 8,512,301 | B2 | 8/2013 | Ma |
| 8,529,530 | B2 | 9/2013 | Koch et al. |
| 8,535,284 | B2 | 9/2013 | Joder et al. |
| 8,546,639 | B2 | 10/2013 | Wada et al. |
| 8,551,062 | B2 | 10/2013 | Kay |
| 8,551,075 | B2 | 10/2013 | Bengtson |
| 8,568,376 | B2 | 10/2013 | Delattre et al. |
| D694,404 | S | 11/2013 | Burgess et al. |
| 8,585,683 | B2 | 11/2013 | Bengtson et al. |
| 8,652,112 | B2 | 2/2014 | Johannison et al. |
| 8,669,412 | B2 | 3/2014 | Fernkvist et al. |
| D702,973 | S | 4/2014 | Norland et al. |
| 8,702,667 | B1 | 4/2014 | Johnson |
| 8,703,032 | B2 | 4/2014 | Menon et al. |
| D704,330 | S | 5/2014 | Cicatelli |
| D704,510 | S | 5/2014 | Mason et al. |
| D705,423 | S | 5/2014 | Walsh Cutler |
| D705,926 | S | 5/2014 | Burgess et al. |
| 8,714,394 | B2 | 5/2014 | Wulf |
| 8,715,267 | B2 | 5/2014 | Bengtson et al. |
| 8,740,852 | B2 | 6/2014 | Aviles |
| 8,757,425 | B2 | 6/2014 | Copeland |
| 8,777,032 | B2 | 7/2014 | Biesecker et al. |
| 8,808,260 | B2 | 8/2014 | Koch et al. |
| 8,839,792 | B2 | 9/2014 | Brunner |
| 8,864,730 | B2 | 10/2014 | Conway et al. |
| 8,881,923 | B2 | 11/2014 | Higginson |
| 8,882,731 | B2 | 11/2014 | Suzuki et al. |
| 8,936,585 | B2 | 1/2015 | Carson et al. |
| D729,581 | S | 5/2015 | Boroski |
| 9,028,460 | B2 | 5/2015 | Medeiros |
| 9,056,698 | B2 | 6/2015 | Noer |
| 9,078,792 | B2 | 7/2015 | Ruiz |
| 9,145,879 | B2 | 9/2015 | Pirovano et al. |
| 9,173,602 | B2 | 11/2015 | Gilbert |
| 9,173,799 | B2 | 11/2015 | Tanimoto et al. |
| 9,187,220 | B2 | 11/2015 | Biesecker et al. |
| 9,199,772 | B2 | 12/2015 | Krippendorf |
| 9,233,020 | B2 | 1/2016 | Matsumiya |
| 9,248,058 | B2 | 2/2016 | Conway et al. |
| 9,308,118 | B1 | 4/2016 | Dupree et al. |
| 9,309,029 | B2 | 4/2016 | Incorvia et al. |
| 9,333,281 | B2 | 5/2016 | Giezendanner et al. |
| 9,381,108 | B2 | 7/2016 | Longoni et al. |
| 9,382,047 | B2 | 7/2016 | Schmidtner et al. |
| 9,402,424 | B2 | 8/2016 | Roy |
| 9,415,191 | B2 | 8/2016 | Aviles |
| 9,456,937 | B2 | 10/2016 | Ellis |
| 9,480,595 | B2 | 11/2016 | Baham et al. |
| 9,517,865 | B2 | 12/2016 | Albers et al. |
| D777,941 | S | 1/2017 | Piramoon |
| 9,533,806 | B2 | 1/2017 | Ding et al. |
| 9,550,611 | B2 | 1/2017 | Hodge |
| 9,555,930 | B2 | 1/2017 | Campbell et al. |
| 9,623,159 | B2 | 4/2017 | Locke |
| D789,522 | S | 6/2017 | Burgess et al. |
| 9,687,849 | B2 | 6/2017 | Bruno et al. |
| 9,694,949 | B2 | 7/2017 | Hendricks et al. |
| 9,709,048 | B2 | 7/2017 | Kinjo |
| 9,713,547 | B2 | 7/2017 | Lee et al. |
| 9,732,754 | B2 | 8/2017 | Huang et al. |
| 9,737,433 | B2 | 8/2017 | Joh |
| 9,752,564 | B2 | 9/2017 | Arceno et al. |
| 9,788,992 | B2 | 10/2017 | Harvie |
| D804,907 | S | 12/2017 | Sandoval |
| D806,236 | S | 12/2017 | Lin |
| 9,868,564 | B2 | 1/2018 | Mcgirr et al. |
| D814,239 | S | 4/2018 | Arora |
| D817,484 | S | 5/2018 | Lafond |
| 9,968,908 | B2 | 5/2018 | Ladrech et al. |

(56) References Cited

U.S. PATENT DOCUMENTS

| | | | |
|---|---|---|---|
| 10,010,393 | B1 | 7/2018 | Nguyen et al. |
| 10,037,640 | B2 | 7/2018 | Gordon |
| 10,058,470 | B2 | 8/2018 | Phillips |
| 10,098,990 | B2 | 10/2018 | Koch et al. |
| D835,264 | S | 12/2018 | Mozzicato et al. |
| D835,779 | S | 12/2018 | Mozzicato et al. |
| D840,533 | S | 2/2019 | Mozzicato et al. |
| D840,534 | S | 2/2019 | Mozzicato et al. |
| 10,225,376 | B2 | 3/2019 | Perez Martinez |
| 10,226,376 | B2 | 3/2019 | Sanchez et al. |
| 10,258,517 | B1 | 4/2019 | Maschino et al. |
| D848,612 | S | 5/2019 | Mozzicato et al. |
| 10,307,305 | B1 | 6/2019 | Hodges |
| 10,335,121 | B2 | 7/2019 | Desai |
| D856,512 | S | 8/2019 | Cowart et al. |
| 10,376,406 | B2 | 8/2019 | Newton |
| 10,376,407 | B2 | 8/2019 | Newton |
| 10,390,989 | B2 | 8/2019 | Sanchez et al. |
| D858,144 | S | 9/2019 | Fu |
| 10,406,039 | B2 | 9/2019 | Villarreal |
| 10,407,222 | B2 | 9/2019 | Allen |
| 10,478,356 | B2 | 11/2019 | Griffin |
| 10,500,108 | B1 | 12/2019 | Maschino et al. |
| 10,502,198 | B2 | 12/2019 | Stumpf et al. |
| 10,538,366 | B2 | 1/2020 | Pentelovitch et al. |
| 10,569,938 | B2 | 2/2020 | Zhao et al. |
| 10,577,156 | B2 | 3/2020 | Dagnelie et al. |
| RE47,930 | E | 4/2020 | Cho |
| 10,618,721 | B2 | 4/2020 | Vazin |
| D884,390 | S | 5/2020 | Wang |
| 10,669,079 | B2 | 6/2020 | Freedman et al. |
| D892,315 | S | 8/2020 | Airy |
| 10,730,672 | B2 | 8/2020 | Bertram et al. |
| 10,737,848 | B2 | 8/2020 | Philip et al. |
| 10,765,854 | B2 | 9/2020 | Law et al. |
| 10,766,670 | B2 | 9/2020 | Kittmann |
| 10,799,386 | B1 | 10/2020 | Harrison |
| 10,806,623 | B2 | 10/2020 | VanMiddendorp et al. |
| 10,806,642 | B2 | 10/2020 | Tagomori et al. |
| D901,214 | S | 11/2020 | Hu |
| 10,849,799 | B2 | 12/2020 | Nishikawa et al. |
| 10,857,025 | B2 | 12/2020 | Davis et al. |
| 10,865,017 | B1 | 12/2020 | Cowart et al. |
| 10,889,412 | B2 | 1/2021 | West et al. |
| 10,913,581 | B2 | 2/2021 | Stahlecker |
| D912,244 | S | 3/2021 | Rehm et al. |
| 10,952,889 | B2 | 3/2021 | Newton et al. |
| 10,973,378 | B2 | 4/2021 | Ryu et al. |
| 10,973,678 | B2 | 4/2021 | Newton et al. |
| 10,974,874 | B2 | 4/2021 | Ragias et al. |
| 11,000,401 | B2 | 5/2021 | Ecklund et al. |
| 11,002,165 | B2 | 5/2021 | Poulin |
| D923,365 | S | 6/2021 | Wang |
| 11,020,567 | B2 | 6/2021 | Rule et al. |
| 11,026,829 | B2 | 6/2021 | Harvie |
| 11,027,900 | B2 | 6/2021 | Liu |
| 11,045,346 | B2 | 6/2021 | Argent et al. |
| D928,946 | S | 8/2021 | Sanchez et al. |
| 11,090,183 | B2 | 8/2021 | Sanchez et al. |
| 11,160,695 | B2 | 11/2021 | Febo et al. |
| 11,160,697 | B2 | 11/2021 | Maschino et al. |
| 11,168,420 | B2 | 11/2021 | Kinugasa et al. |
| 11,179,506 | B2 | 11/2021 | Barr et al. |
| 11,199,116 | B2 | 12/2021 | Ostromecki et al. |
| 11,207,206 | B2 | 12/2021 | Sharma et al. |
| D941,998 | S | 1/2022 | Tretheway et al. |
| 11,226,376 | B2 | 1/2022 | Yamauchi et al. |
| 11,253,389 | B2 | 2/2022 | Sharma et al. |
| 11,253,407 | B2 | 2/2022 | Miao et al. |
| 11,326,586 | B2 | 5/2022 | Milner et al. |
| 11,369,508 | B2 | 6/2022 | Ecklund et al. |
| 11,369,524 | B2 | 6/2022 | Hubbard et al. |
| 11,376,152 | B2 | 7/2022 | Sanchez et al. |
| 11,382,786 | B2 | 7/2022 | Sanchez et al. |
| 11,382,788 | B2 | 7/2022 | Hjorth et al. |
| 11,389,318 | B2 | 7/2022 | Radl et al. |
| 11,395,871 | B2 | 7/2022 | Radl et al. |
| 11,399,990 | B2 | 8/2022 | Suyama |
| 11,426,303 | B2 | 8/2022 | Davis et al. |
| 11,446,174 | B2 | 9/2022 | Newton |
| 11,504,265 | B2 | 11/2022 | Godinez et al. |
| 11,529,252 | B2 | 12/2022 | Glithero et al. |
| 11,547,788 | B2 | 1/2023 | Radl et al. |
| 11,702,969 | B2 | 7/2023 | Bartu et al. |
| 11,806,266 | B2 | 11/2023 | Sanchez et al. |
| 11,813,189 | B2 | 11/2023 | Hussey et al. |
| 11,839,567 | B2 | 12/2023 | Davis et al. |
| D1,010,109 | S | 1/2024 | Ecklund et al. |
| 11,857,716 | B2 | 1/2024 | Lee et al. |
| 11,865,030 | B2 | 1/2024 | Davis et al. |
| 11,877,948 | B2 | 1/2024 | Pinlac |
| 11,890,221 | B2 | 2/2024 | Ulreich et al. |
| 11,911,160 | B2 | 2/2024 | Woodard et al. |
| 11,925,575 | B2 | 3/2024 | Newton |
| 11,938,053 | B2 | 3/2024 | Austermann et al. |
| 11,944,740 | B2 | 4/2024 | Hughett et al. |
| 11,994,122 | B2 | 5/2024 | Bodain |
| 11,998,475 | B2 | 6/2024 | Becker et al. |
| 12,023,457 | B2 | 7/2024 | Mann et al. |
| 12,042,422 | B2 | 7/2024 | Davis et al. |
| 12,048,644 | B2 | 7/2024 | Davis |
| D1,038,385 | S | 8/2024 | Ecklund et al. |
| 12,064,372 | B2 | 8/2024 | Godinez et al. |
| 12,070,432 | B2 | 8/2024 | Tourchak et al. |
| 12,090,083 | B2 | 9/2024 | Ecklund et al. |
| 12,121,468 | B2 | 10/2024 | Sanchez et al. |
| 12,133,813 | B2 | 11/2024 | Ulreich et al. |
| 12,138,195 | B2 | 11/2024 | Alder et al. |
| D1,054,019 | S | 12/2024 | Miyawaki |
| 12,161,579 | B2 | 12/2024 | Sanchez et al. |
| D1,059,585 | S | 1/2025 | Miyawaki |
| D1,059,586 | S | 1/2025 | Miyawaki |
| 12,186,229 | B2 | 1/2025 | Davis et al. |
| 12,193,962 | B2 | 1/2025 | Newton et al. |
| 12,208,031 | B2 | 1/2025 | Knapp et al. |
| 12,233,003 | B2 | 2/2025 | Newton |
| D1,067,424 | S | 3/2025 | Naughton et al. |
| 12,245,966 | B2 | 3/2025 | Newton |
| 12,257,173 | B2 | 3/2025 | Newton et al. |
| 12,274,638 | B2 | 4/2025 | Spector |
| D1,074,995 | S | 5/2025 | Laffay et al. |
| 12,324,765 | B2 | 6/2025 | Sanchez et al. |
| 12,350,190 | B2 | 7/2025 | Hughett, Sr. et al. |
| 12,447,042 | B2 | 10/2025 | Martin et al. |
| 12,465,515 | B2 | 11/2025 | Brooks |
| D1,104,255 | S | 12/2025 | Hanna et al. |
| D1,107,222 | S | 12/2025 | Ecklund et al. |
| 12,594,182 | B2 | 4/2026 | Davis et al. |
| 2001/0037097 | A1 | 11/2001 | Cheng et al. |
| 2001/0037098 | A1 | 11/2001 | Snyder |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |
| 2002/0033200 | A1 | 3/2002 | Alex et al. |
| 2002/0042945 | A1 | 4/2002 | Sands |
| 2002/0058915 | A1 | 5/2002 | Wakabayashi |
| 2002/0087131 | A1 | 7/2002 | Wolff et al. |
| 2002/0091364 | A1 | 7/2002 | Prabhakar |
| 2002/0189992 | A1 | 12/2002 | Schmidt et al. |
| 2002/0193760 | A1 | 12/2002 | Thompson |
| 2002/0193762 | A1 | 12/2002 | Suydam |
| 2003/0004436 | A1 | 1/2003 | Schmidt et al. |
| 2003/0018309 | A1 | 1/2003 | Breznock |
| 2003/0032931 | A1 | 2/2003 | Grundke et al. |
| 2003/0032944 | A1 | 2/2003 | Cawood |
| 2003/0073964 | A1 | 4/2003 | Palumbo et al. |
| 2003/0074724 | A1 | 4/2003 | Sands |
| 2003/0097100 | A1 | 5/2003 | Watson |
| 2003/0110868 | A1 | 6/2003 | Muller et al. |
| 2003/0120178 | A1 | 6/2003 | Heki |
| 2003/0129178 | A1 | 7/2003 | Wegman et al. |
| 2003/0132352 | A1 | 7/2003 | Weaver |
| 2003/0157859 | A1 | 8/2003 | Ishikawa |

(56) References Cited

U.S. PATENT DOCUMENTS

| | | | |
|---|---|---|---|
| 2003/0178360 | A1 | 9/2003 | Haldopoulos et al. |
| 2003/0181880 | A1 | 9/2003 | Schwartz |
| 2003/0195484 | A1 | 10/2003 | Harvie |
| 2003/0204173 | A1 | 10/2003 | Burns et al. |
| 2003/0233079 | A1 | 12/2003 | Parks et al. |
| 2004/0002687 | A1 | 1/2004 | Burns et al. |
| 2004/0006321 | A1 | 1/2004 | Cheng et al. |
| 2004/0015141 | A1 | 1/2004 | Cheng et al. |
| 2004/0056122 | A1 | 3/2004 | Male et al. |
| 2004/0084465 | A1 | 5/2004 | Luburic |
| 2004/0098794 | A1 | 5/2004 | Ernest et al. |
| 2004/0102753 | A1 | 5/2004 | Butler |
| 2004/0127872 | A1 | 7/2004 | Petryk et al. |
| 2004/0128749 | A1 | 7/2004 | Scott |
| 2004/0143229 | A1 | 7/2004 | Easter |
| 2004/0147863 | A1 | 7/2004 | Diaz et al. |
| 2004/0147894 | A1 | 7/2004 | Mizutani et al. |
| 2004/0147895 | A1 | 7/2004 | Mizutani et al. |
| 2004/0158221 | A1 | 8/2004 | Mizutani et al. |
| 2004/0176731 | A1 | 9/2004 | Cheng et al. |
| 2004/0176746 | A1 | 9/2004 | Forral |
| 2004/0181201 | A1 | 9/2004 | Mizutani et al. |
| 2004/0187200 | A1 | 9/2004 | Otto et al. |
| 2004/0191919 | A1 | 9/2004 | Unger et al. |
| 2004/0194792 | A1 | 10/2004 | Zhuang et al. |
| 2004/0200936 | A1 | 10/2004 | Opperthauser |
| 2004/0207530 | A1 | 10/2004 | Nielsen |
| 2004/0215133 | A1 | 10/2004 | Weber et al. |
| 2004/0236292 | A1 | 11/2004 | Tazoe et al. |
| 2004/0243075 | A1 | 12/2004 | Harvie |
| 2004/0254547 | A1 | 12/2004 | Okabe et al. |
| 2005/0010182 | A1 | 1/2005 | Parks et al. |
| 2005/0010197 | A1 | 1/2005 | Lau et al. |
| 2005/0033248 | A1 | 2/2005 | Machida et al. |
| 2005/0065471 | A1 | 3/2005 | Kuntz |
| 2005/0070861 | A1 | 3/2005 | Okabe et al. |
| 2005/0070862 | A1 | 3/2005 | Tazoe et al. |
| 2005/0082300 | A1 | 4/2005 | Modrell et al. |
| 2005/0097662 | A1 | 5/2005 | Leimkuhler et al. |
| 2005/0101924 | A1 | 5/2005 | Elson et al. |
| 2005/0119630 | A1 | 6/2005 | Harvie |
| 2005/0131361 | A1 | 6/2005 | Miskie |
| 2005/0137557 | A1 | 6/2005 | Swiecicki et al. |
| 2005/0137560 | A1 | 6/2005 | Mizutani et al. |
| 2005/0137561 | A1 | 6/2005 | Mizutani et al. |
| 2005/0148984 | A1 | 7/2005 | Lindsay et al. |
| 2005/0154360 | A1 | 7/2005 | Harvie |
| 2005/0177070 | A1 | 8/2005 | Levinson et al. |
| 2005/0197645 | A1 | 9/2005 | Karpowicz et al. |
| 2005/0215969 | A1 | 9/2005 | Mizutani et al. |
| 2005/0273069 | A1 | 12/2005 | Mizutani et al. |
| 2005/0273920 | A1 | 12/2005 | Marinas |
| 2005/0277903 | A1 | 12/2005 | Mizutani et al. |
| 2005/0277904 | A1 | 12/2005 | Chase et al. |
| 2005/0279359 | A1 | 12/2005 | LeBlanc et al. |
| 2006/0004332 | A1 | 1/2006 | Marx |
| 2006/0005307 | A1 | 1/2006 | Arguelles |
| 2006/0015080 | A1 | 1/2006 | Mahnensmith |
| 2006/0015081 | A1 | 1/2006 | Suzuki et al. |
| 2006/0016778 | A1 | 1/2006 | Park |
| 2006/0054384 | A1 | 3/2006 | Chen |
| 2006/0069359 | A1 | 3/2006 | Dipalma et al. |
| 2006/0079852 | A1 | 4/2006 | Bubb et al. |
| 2006/0079854 | A1 | 4/2006 | Kay et al. |
| 2006/0084932 | A1 | 4/2006 | Koizumi et al. |
| 2006/0100596 | A1 | 5/2006 | Miskie |
| 2006/0111648 | A1 | 5/2006 | Vermaak |
| 2006/0113334 | A1 | 6/2006 | Mikhail et al. |
| 2006/0155214 | A1 | 7/2006 | Wightman |
| 2006/0166350 | A1 | 7/2006 | Lowe et al. |
| 2006/0171997 | A1 | 8/2006 | Gruenbacher et al. |
| 2006/0180566 | A1 | 8/2006 | Mataya |
| 2006/0200102 | A1 | 9/2006 | Cooper |
| 2006/0229575 | A1 | 10/2006 | Boiarski |
| 2006/0229576 | A1 | 10/2006 | Conway et al. |
| 2006/0231648 | A1 | 10/2006 | Male et al. |
| 2006/0235266 | A1 | 10/2006 | Nan |
| 2006/0235359 | A1 | 10/2006 | Marland |
| 2006/0241553 | A1 | 10/2006 | Harvie |
| 2006/0269439 | A1 | 11/2006 | White |
| 2006/0277670 | A1 | 12/2006 | Baker et al. |
| 2007/0006368 | A1 | 1/2007 | Key et al. |
| 2007/0010797 | A1 | 1/2007 | Nishtala et al. |
| 2007/0016152 | A1 | 1/2007 | Karpowicz et al. |
| 2007/0025886 | A1 | 2/2007 | Yong |
| 2007/0032765 | A1 | 2/2007 | Honda |
| 2007/0038194 | A1 | 2/2007 | Wada et al. |
| 2007/0055209 | A1 | 3/2007 | Patel et al. |
| 2007/0073252 | A1 | 3/2007 | Forgrave |
| 2007/0106177 | A1 | 5/2007 | Hama |
| 2007/0117880 | A1 | 5/2007 | Elson et al. |
| 2007/0118993 | A1 | 5/2007 | Bates |
| 2007/0135786 | A1 | 6/2007 | Schmidt et al. |
| 2007/0137718 | A1 | 6/2007 | Rushlander et al. |
| 2007/0149935 | A1 | 6/2007 | Dirico |
| 2007/0191804 | A1 | 8/2007 | Coley |
| 2007/0203464 | A1 | 8/2007 | Green et al. |
| 2007/0214553 | A1 | 9/2007 | Carromba et al. |
| 2007/0225663 | A1 | 9/2007 | Watt et al. |
| 2007/0225666 | A1 | 9/2007 | Otto |
| 2007/0225668 | A1 | 9/2007 | Otto |
| 2007/0266486 | A1 | 11/2007 | Ramirez |
| 2007/0270716 | A1 | 11/2007 | Wu et al. |
| 2007/0282309 | A1 | 12/2007 | Bengtson et al. |
| 2008/0004576 | A1 | 1/2008 | Tanaka et al. |
| 2008/0015526 | A1 | 1/2008 | Reiner et al. |
| 2008/0015527 | A1 | 1/2008 | House |
| 2008/0033386 | A1 | 2/2008 | Okabe et al. |
| 2008/0041869 | A1 | 2/2008 | Backaert |
| 2008/0077099 | A1 | 3/2008 | House |
| 2008/0091153 | A1 | 4/2008 | Harvie |
| 2008/0091158 | A1 | 4/2008 | Yang |
| 2008/0091162 | A1 | 4/2008 | Maldonado et al. |
| 2008/0114327 | A1 | 5/2008 | Barge |
| 2008/0140033 | A1 | 6/2008 | Burgess et al. |
| 2008/0167634 | A1 | 7/2008 | Kouta et al. |
| 2008/0183157 | A1 | 7/2008 | Walters |
| 2008/0200884 | A1 | 8/2008 | Perkins et al. |
| 2008/0215031 | A1 | 9/2008 | Belfort et al. |
| 2008/0234642 | A1 | 9/2008 | Patterson et al. |
| 2008/0269703 | A1 | 10/2008 | Collins et al. |
| 2008/0281282 | A1 | 11/2008 | Finger et al. |
| 2008/0287894 | A1 | 11/2008 | Van Den Heuvel et al. |
| 2008/0312550 | A1 | 12/2008 | Nishtala et al. |
| 2009/0025717 | A1 | 1/2009 | Pinel |
| 2009/0048570 | A1 | 2/2009 | Jensen |
| 2009/0056003 | A1 | 3/2009 | Ivie et al. |
| 2009/0069761 | A1 | 3/2009 | Vogel |
| 2009/0069765 | A1 | 3/2009 | Wortham |
| 2009/0120179 | A1 | 5/2009 | Nylander et al. |
| 2009/0192482 | A1 | 7/2009 | Dodge et al. |
| 2009/0199857 | A1 | 8/2009 | Peake et al. |
| 2009/0226541 | A1 | 9/2009 | Scholz et al. |
| 2009/0234312 | A1 | 9/2009 | Otoole et al. |
| 2009/0247968 | A1 | 10/2009 | Brooks et al. |
| 2009/0251510 | A1 | 10/2009 | Noro et al. |
| 2009/0254040 | A1 | 10/2009 | Bierman et al. |
| 2009/0259206 | A1 | 10/2009 | Kai et al. |
| 2009/0264840 | A1 | 10/2009 | Virginio |
| 2009/0270822 | A1 | 10/2009 | Medeiros |
| 2009/0281510 | A1 | 11/2009 | Fisher |
| 2009/0283982 | A1 | 11/2009 | Thomas |
| 2009/0306610 | A1 | 12/2009 | Van Den Heuvel et al. |
| 2010/0004612 | A1 | 1/2010 | Thevenin |
| 2010/0030189 | A1 | 2/2010 | Fleming |
| 2010/0031429 | A1 | 2/2010 | Kim et al. |
| 2010/0032789 | A1 | 2/2010 | Schoen et al. |
| 2010/0058660 | A1 | 3/2010 | Williams |
| 2010/0121289 | A1 | 5/2010 | Parks et al. |
| 2010/0160882 | A1 | 6/2010 | Lowe |
| 2010/0174250 | A1 | 7/2010 | Hu et al. |
| 2010/0179493 | A1 | 7/2010 | Heagle et al. |
| 2010/0185168 | A1 | 7/2010 | Graauw et al. |
| 2010/0198172 | A1 | 8/2010 | Wada et al. |

(56) References Cited

U.S. PATENT DOCUMENTS

| | | | |
|---|---|---|---|
| 2010/0211032 | A1 | 8/2010 | Tsai et al. |
| 2010/0234820 | A1 | 9/2010 | Tsai et al. |
| 2010/0241104 | A1 | 9/2010 | Gilbert |
| 2010/0263113 | A1 | 10/2010 | Shelton et al. |
| 2010/0310845 | A1 | 12/2010 | Bond et al. |
| 2011/0022011 | A1 | 1/2011 | Edward |
| 2011/0028920 | A1 | 2/2011 | Johannison |
| 2011/0028922 | A1 | 2/2011 | Kay et al. |
| 2011/0034889 | A1 | 2/2011 | Smith |
| 2011/0036837 | A1 | 2/2011 | Shang |
| 2011/0040267 | A1 | 2/2011 | Wada et al. |
| 2011/0040271 | A1 | 2/2011 | Rogers et al. |
| 2011/0054426 | A1 | 3/2011 | Stewart et al. |
| 2011/0060299 | A1 | 3/2011 | Wada et al. |
| 2011/0060300 | A1 | 3/2011 | Weig et al. |
| 2011/0077495 | A1 | 3/2011 | Gilbert |
| 2011/0077606 | A1 | 3/2011 | Wilcox et al. |
| 2011/0087337 | A1 | 4/2011 | Forsell |
| 2011/0145993 | A1 | 6/2011 | Rader et al. |
| 2011/0152802 | A1 | 6/2011 | Dicamillo et al. |
| 2011/0152842 | A1 | 6/2011 | Graffam et al. |
| 2011/0164147 | A1 | 7/2011 | Takahashi et al. |
| 2011/0172620 | A1 | 7/2011 | Khambatta |
| 2011/0172625 | A1 | 7/2011 | Wada et al. |
| 2011/0198904 | A1 | 8/2011 | Thomas et al. |
| 2011/0202024 | A1 | 8/2011 | Cozzens |
| 2011/0238023 | A1 | 9/2011 | Slayton |
| 2011/0240648 | A1 | 10/2011 | Tucker |
| 2011/0251572 | A1 | 10/2011 | Nishtala et al. |
| 2011/0265889 | A1 | 11/2011 | Tanaka et al. |
| 2011/0276020 | A1 | 11/2011 | Mitsui |
| 2011/0319804 | A1 | 12/2011 | Greener |
| 2012/0004079 | A1 | 1/2012 | Hyacinth |
| 2012/0029452 | A1 | 2/2012 | Roedsten |
| 2012/0035577 | A1 | 2/2012 | Tomes et al. |
| 2012/0041400 | A1 | 2/2012 | Christensen |
| 2012/0059328 | A1 | 3/2012 | Dikeman et al. |
| 2012/0066825 | A1 | 3/2012 | Birbara et al. |
| 2012/0103347 | A1 | 5/2012 | Wheaton et al. |
| 2012/0116336 | A1 | 5/2012 | Sharma et al. |
| 2012/0137420 | A1 | 6/2012 | Gordon et al. |
| 2012/0165768 | A1 | 6/2012 | Sekiyama et al. |
| 2012/0209216 | A1 | 8/2012 | Jensen et al. |
| 2012/0209225 | A1 | 8/2012 | Hu et al. |
| 2012/0210503 | A1 | 8/2012 | Anzivino et al. |
| 2012/0215187 | A1 | 8/2012 | Tippet et al. |
| 2012/0228055 | A1 | 9/2012 | Kato et al. |
| 2012/0233761 | A1 | 9/2012 | Huang |
| 2012/0245541 | A1 | 9/2012 | Suzuki et al. |
| 2012/0245542 | A1 | 9/2012 | Suzuki et al. |
| 2012/0245547 | A1 | 9/2012 | Wilcox et al. |
| 2012/0253303 | A1 | 10/2012 | Suzuki et al. |
| 2012/0271259 | A1 | 10/2012 | Ulert |
| 2012/0296305 | A1 | 11/2012 | Barraza Khaled et al. |
| 2012/0316522 | A1 | 12/2012 | Carter et al. |
| 2012/0330256 | A1 | 12/2012 | Wilcox et al. |
| 2013/0006206 | A1 | 1/2013 | Wada et al. |
| 2013/0019374 | A1 | 1/2013 | Schwartz |
| 2013/0036544 | A1 | 2/2013 | Lee et al. |
| 2013/0045651 | A1 | 2/2013 | Esteves et al. |
| 2013/0046258 | A1 | 2/2013 | Chambers |
| 2013/0053804 | A1 | 2/2013 | Soerensen et al. |
| 2013/0096523 | A1 | 4/2013 | Chang et al. |
| 2013/0110059 | A1 | 5/2013 | Kossow et al. |
| 2013/0138064 | A1 | 5/2013 | Stroebech et al. |
| 2013/0144240 | A1 | 6/2013 | Ellis |
| 2013/0150813 | A1 | 6/2013 | Gordon et al. |
| 2013/0158494 | A1 | 6/2013 | Ong et al. |
| 2013/0165880 | A1 | 6/2013 | Amos et al. |
| 2013/0190706 | A1 | 7/2013 | Kleiner |
| 2013/0211385 | A1 | 8/2013 | Lazarus |
| 2013/0218112 | A1 | 8/2013 | Thompson |
| 2013/0245496 | A1 | 9/2013 | Wells et al. |
| 2013/0245586 | A1 | 9/2013 | Jha |
| 2013/0253528 | A1 | 9/2013 | Haffner et al. |
| 2013/0274711 | A1 | 10/2013 | O'Day |
| 2013/0292537 | A1 | 11/2013 | Dirico |
| 2013/0324954 | A1 | 12/2013 | Friedrich |
| 2013/0330501 | A1 | 12/2013 | Aizenberg et al. |
| 2014/0005647 | A1 | 1/2014 | Shuffler et al. |
| 2014/0031774 | A1 | 1/2014 | Bengtson |
| 2014/0039432 | A1 | 2/2014 | Dunbar et al. |
| 2014/0039440 | A1 | 2/2014 | Doescher |
| 2014/0058347 | A1 | 2/2014 | Marquette |
| 2014/0107595 | A1 | 4/2014 | Blott et al. |
| 2014/0107599 | A1 | 4/2014 | Fink et al. |
| 2014/0157499 | A1 | 6/2014 | Suzuki et al. |
| 2014/0171889 | A1 | 6/2014 | Hopman et al. |
| 2014/0182051 | A1 | 7/2014 | Tanimoto et al. |
| 2014/0196189 | A1 | 7/2014 | Lee et al. |
| 2014/0216478 | A1 | 8/2014 | Park et al. |
| 2014/0230831 | A1 | 8/2014 | Zaltsberg et al. |
| 2014/0257231 | A1 | 9/2014 | Wang et al. |
| 2014/0303582 | A1 | 10/2014 | Wright et al. |
| 2014/0316381 | A1 | 10/2014 | Reglin |
| 2014/0325746 | A1 | 11/2014 | Block |
| 2014/0343516 | A1 | 11/2014 | Coulthard et al. |
| 2014/0348139 | A1 | 11/2014 | Gomez Martinez |
| 2014/0352050 | A1 | 12/2014 | Yao et al. |
| 2014/0371628 | A1 | 12/2014 | Desai |
| 2015/0045757 | A1 | 2/2015 | Lee et al. |
| 2015/0047114 | A1 | 2/2015 | Ramirez |
| 2015/0048089 | A1 | 2/2015 | Robertson |
| 2015/0135423 | A1 | 5/2015 | Sharpe et al. |
| 2015/0157300 | A1 | 6/2015 | Ealovega et al. |
| 2015/0209188 | A1 | 7/2015 | Scheremet et al. |
| 2015/0209194 | A1 | 7/2015 | Heyman |
| 2015/0216714 | A1 | 8/2015 | Sasaki et al. |
| 2015/0238687 | A1 | 8/2015 | Novakovic et al. |
| 2015/0267862 | A1 | 9/2015 | Mishler |
| 2015/0290421 | A1 | 10/2015 | Glickman et al. |
| 2015/0290425 | A1 | 10/2015 | Macy et al. |
| 2015/0320583 | A1 | 11/2015 | Harvie |
| 2015/0329255 | A1 | 11/2015 | Rzepecki |
| 2015/0342799 | A1 | 12/2015 | Michiels et al. |
| 2015/0359660 | A1 | 12/2015 | Harvie |
| 2015/0359996 | A1 | 12/2015 | Arora et al. |
| 2015/0366699 | A1 | 12/2015 | Nelson |
| 2015/0374535 | A1 | 12/2015 | Davis et al. |
| 2016/0008193 | A1 | 1/2016 | Schulke |
| 2016/0029998 | A1 | 2/2016 | Brister et al. |
| 2016/0030228 | A1 | 2/2016 | Jones |
| 2016/0038356 | A1 | 2/2016 | Yao et al. |
| 2016/0051395 | A1 | 2/2016 | Ugarte |
| 2016/0058322 | A1 | 3/2016 | Brister et al. |
| 2016/0060001 | A1 | 3/2016 | Wada et al. |
| 2016/0100976 | A1 | 4/2016 | Conway et al. |
| 2016/0106604 | A1 | 4/2016 | Timm |
| 2016/0113809 | A1 | 4/2016 | Kim |
| 2016/0135792 | A1 | 5/2016 | Cai |
| 2016/0136338 | A1 | 5/2016 | Lee et al. |
| 2016/0183689 | A1 | 6/2016 | Miner |
| 2016/0256022 | A1 | 9/2016 | Le |
| 2016/0270982 | A1 | 9/2016 | Raycheck et al. |
| 2016/0278662 | A1 | 9/2016 | Brister et al. |
| 2016/0327553 | A1 | 11/2016 | Edwards et al. |
| 2016/0354268 | A1 | 12/2016 | Fennell |
| 2016/0357400 | A1 | 12/2016 | Penha et al. |
| 2016/0366699 | A1 | 12/2016 | Zhang et al. |
| 2016/0367226 | A1 | 12/2016 | Newton et al. |
| 2016/0367411 | A1 | 12/2016 | Justiz et al. |
| 2016/0374848 | A1 | 12/2016 | Sanchez et al. |
| 2017/0007438 | A1 | 1/2017 | Harvie |
| 2017/0014560 | A1 | 1/2017 | Minskoff et al. |
| 2017/0028110 | A1 | 2/2017 | Smith et al. |
| 2017/0042724 | A1 | 2/2017 | Ugarte |
| 2017/0042748 | A1 | 2/2017 | Griffin |
| 2017/0049605 | A1 | 2/2017 | Wisniewski |
| 2017/0100276 | A1 | 4/2017 | Joh |
| 2017/0107312 | A1 | 4/2017 | Hinayama et al. |
| 2017/0128638 | A1 | 5/2017 | Giezendanner et al. |
| 2017/0136209 | A1 | 5/2017 | Burnett et al. |
| 2017/0143534 | A1 | 5/2017 | Sanchez |
| 2017/0165100 | A1 | 6/2017 | Jackson et al. |

(56) References Cited

U.S. PATENT DOCUMENTS

2017/0165405 A1 6/2017 Muser et al.
2017/0189225 A1 7/2017 Voorhees et al.
2017/0202692 A1 7/2017 Laniado
2017/0216081 A1 8/2017 Accosta
2017/0238911 A1 8/2017 Duval
2017/0246026 A1 8/2017 Laniado
2017/0252014 A1 9/2017 Siller Gonzalez et al.
2017/0252202 A9 9/2017 Sanchez et al.
2017/0266031 A1* 9/2017 Sanchez ................ A61F 5/4404
2017/0266658 A1 9/2017 Bruno et al.
2017/0281399 A1 10/2017 Vanmiddendorp et al.
2017/0281419 A1 10/2017 Pintado
2017/0312114 A1 11/2017 Glithero
2017/0312116 A1 11/2017 Laniado
2017/0312405 A1 11/2017 Newton
2017/0325788 A1 11/2017 Ealovega et al.
2017/0333244 A1 11/2017 Laniado
2017/0340489 A1 11/2017 Yamada
2017/0348139 A1 12/2017 Newton et al.
2017/0354532 A1 12/2017 Holt
2017/0354551 A1 12/2017 Gawley et al.
2017/0367873 A1 12/2017 Grannum
2018/0002075 A1 1/2018 Lee
2018/0008451 A1 1/2018 Stroebech
2018/0008804 A1 1/2018 Laniado
2018/0021218 A1 1/2018 Brosch et al.
2018/0028349 A1 2/2018 Newton et al.
2018/0037384 A1 2/2018 Archeny et al.
2018/0049910 A1 2/2018 Newton
2018/0064572 A1 3/2018 Wiltshire
2018/0104131 A1 4/2018 Killian
2018/0127187 A1 5/2018 Sewell
2018/0149635 A1 5/2018 Abir
2018/0169281 A1 6/2018 Russell et al.
2018/0193215 A1 7/2018 Davies et al.
2018/0200101 A1 7/2018 Su
2018/0214297 A1 8/2018 Hughett et al.
2018/0215649 A1 8/2018 Wada et al.
2018/0221216 A1 8/2018 Benz et al.
2018/0228642 A1* 8/2018 Davis ...................... A61F 5/451
2018/0229014 A1 8/2018 Guirguis et al.
2018/0256384 A1 9/2018 Kasirye
2018/0271694 A1 9/2018 Fernandez et al.
2018/0280236 A1 10/2018 Ludin et al.
2018/0317892 A1 11/2018 Catlin
2018/0325748 A1 11/2018 Sharma et al.
2019/0001029 A1 1/2019 Davie et al.
2019/0001030 A1 1/2019 Braga et al.
2019/0021899 A1 1/2019 Vlet
2019/0029869 A1 1/2019 Huchthausen
2019/0038451 A1 2/2019 Harvie
2019/0046102 A1 2/2019 Kushnir et al.
2019/0059938 A1 2/2019 Holsten
2019/0060138 A1 2/2019 Marquez et al.
2019/0091059 A1 3/2019 Gabriel
2019/0100362 A1 4/2019 Meyers et al.
2019/0133126 A1 5/2019 Modak et al.
2019/0133814 A1 5/2019 Tammen et al.
2019/0142624 A1 5/2019 Sanchez et al.
2019/0224036 A1 7/2019 Sanchez et al.
2019/0226189 A1 7/2019 Braxton
2019/0240079 A1 8/2019 Tuli
2019/0247222 A1 8/2019 Ecklund et al.
2019/0247223 A1 8/2019 Brun et al.
2019/0247623 A1 8/2019 Helm et al.
2019/0282391 A1 9/2019 Johannes et al.
2019/0314189 A1 10/2019 Acosta
2019/0314190 A1 10/2019 Sanchez et al.
2019/0321587 A1 10/2019 Mcmenamin et al.
2019/0344934 A1 11/2019 Faerber et al.
2019/0350746 A1 11/2019 Trachsel
2019/0358372 A1 11/2019 Askem et al.
2019/0365303 A1 12/2019 Bullington et al.
2019/0365307 A1 12/2019 Laing et al.
2019/0365561 A1 12/2019 Newton et al.
2019/0374373 A1 12/2019 Joh
2020/0008985 A1 1/2020 Nguyen et al.
2020/0016012 A1 1/2020 Dutkiewicz
2020/0030595 A1 1/2020 Boukidjian et al.
2020/0040561 A1 2/2020 Sugawara
2020/0046544 A1 2/2020 Godinez et al.
2020/0055638 A1 2/2020 Lau et al.
2020/0070392 A1 3/2020 Huber et al.
2020/0085609 A1 3/2020 Schelch et al.
2020/0085610 A1 3/2020 Cohn et al.
2020/0086090 A1 3/2020 Von Weymarn-schärli et al.
2020/0107518 A1 4/2020 Hiroshima et al.
2020/0129322 A1 4/2020 Leuckel
2020/0171217 A9 6/2020 Braga et al.
2020/0179177 A1 6/2020 Erdem et al.
2020/0187918 A1 6/2020 Wiygul
2020/0206015 A1 7/2020 Langer
2020/0206039 A1 7/2020 Mclain
2020/0214910 A1 7/2020 Varona et al.
2020/0216898 A1 7/2020 Hubbell
2020/0216989 A1 7/2020 Kinugasa et al.
2020/0229964 A1 7/2020 Staali et al.
2020/0231343 A1 7/2020 Freedman et al.
2020/0232841 A1 7/2020 Satish et al.
2020/0246172 A1 8/2020 Ho
2020/0246203 A1 8/2020 Tulk et al.
2020/0255189 A1 8/2020 Liu
2020/0261280 A1 8/2020 Heyman
2020/0276046 A1 9/2020 Staali et al.
2020/0306075 A1 10/2020 Newton et al.
2020/0315837 A1 10/2020 Radl et al.
2020/0315838 A1 10/2020 Eckert
2020/0315872 A1 10/2020 Viens et al.
2020/0315874 A1 10/2020 Viens et al.
2020/0331672 A1 10/2020 Bertram et al.
2020/0345332 A1 11/2020 Duval
2020/0352774 A1 11/2020 Rabinowitz et al.
2020/0353135 A1 11/2020 Gregory et al.
2020/0367677 A1 11/2020 Silsby et al.
2020/0369444 A1 11/2020 Silsby et al.
2020/0375781 A1 12/2020 Staali et al.
2020/0375810 A1 12/2020 Carlin et al.
2020/0384242 A1 12/2020 Havard et al.
2020/0385179 A1 12/2020 Mccourt
2020/0390591 A1 12/2020 Glithero et al.
2020/0390592 A1 12/2020 Merrill
2020/0398024 A1 12/2020 Fletter et al.
2020/0405521 A1 12/2020 Glasroe
2020/0405523 A1 12/2020 Obst et al.
2021/0007910 A1 1/2021 Furukawa
2021/0008771 A1 1/2021 Huber et al.
2021/0009323 A1 1/2021 Markarian et al.
2021/0020072 A1 1/2021 Moehring et al.
2021/0023279 A1 1/2021 Radl et al.
2021/0059853 A1 3/2021 Davis et al.
2021/0061523 A1 3/2021 Bytheway
2021/0069005 A1 3/2021 Sanchez et al.
2021/0069008 A1 3/2021 Blabas et al.
2021/0069009 A1 3/2021 Im
2021/0069030 A1 3/2021 Nishikawa et al.
2021/0077993 A1 3/2021 Nazareth et al.
2021/0113749 A1 4/2021 Radl et al.
2021/0121318 A1 4/2021 Pinlac
2021/0137724 A1 5/2021 Ecklund et al.
2021/0138190 A1 5/2021 Erbey et al.
2021/0154055 A1 5/2021 Villarreal
2021/0170079 A1 6/2021 Radl et al.
2021/0178390 A1 6/2021 Oueslati et al.
2021/0186742 A1 6/2021 Newton et al.
2021/0186744 A1 6/2021 Spector
2021/0206144 A1 7/2021 Ewell
2021/0211568 A1 7/2021 Zhou et al.
2021/0212865 A1 7/2021 Wallajapet et al.
2021/0220162 A1 7/2021 Jamison
2021/0220163 A1 7/2021 Mayrand
2021/0228400 A1 7/2021 Glithero
2021/0228401 A1 7/2021 Becker et al.
2021/0228795 A1 7/2021 Hughett et al.
2021/0229877 A1 7/2021 Ragias et al.

(56) References Cited

U.S. PATENT DOCUMENTS

| | | | |
|---|---|---|---|
| 2021/0236323 | A1 | 8/2021 | Austermann et al. |
| 2021/0236324 | A1 | 8/2021 | Sweeney |
| 2021/0251814 | A1 | 8/2021 | Jönegren et al. |
| 2021/0267787 | A1 | 9/2021 | Nazemi |
| 2021/0275343 | A1 | 9/2021 | Sanchez et al. |
| 2021/0275344 | A1 | 9/2021 | Wing |
| 2021/0290454 | A1 | 9/2021 | Yamada |
| 2021/0290464 | A1 | 9/2021 | Furuta |
| 2021/0315726 | A1 | 10/2021 | Lin |
| 2021/0315727 | A1 | 10/2021 | Jiang |
| 2021/0353449 | A1 | 11/2021 | Sharma et al. |
| 2021/0353450 | A1 | 11/2021 | Sharma et al. |
| 2021/0361469 | A1 | 11/2021 | Liu et al. |
| 2021/0369495 | A1 | 12/2021 | Cheng et al. |
| 2021/0386925 | A1 | 12/2021 | Hartwell et al. |
| 2021/0393433 | A1 | 12/2021 | Godinez et al. |
| 2022/0015958 | A1 | 1/2022 | Ito |
| 2022/0023091 | A1 | 1/2022 | Ecklund et al. |
| 2022/0026546 | A1 | 1/2022 | Aono et al. |
| 2022/0031290 | A1 | 2/2022 | Weed |
| 2022/0031523 | A1 | 2/2022 | Pierpoint |
| 2022/0039995 | A1 | 2/2022 | Johannes et al. |
| 2022/0047410 | A1 | 2/2022 | Walthall |
| 2022/0062025 | A1 | 3/2022 | Shields et al. |
| 2022/0062027 | A1 | 3/2022 | Mitchell et al. |
| 2022/0062028 | A1 | 3/2022 | Mitchell et al. |
| 2022/0062029 | A1 | 3/2022 | Johannes et al. |
| 2022/0066825 | A1 | 3/2022 | Saraf et al. |
| 2022/0071811 | A1 | 3/2022 | Cheng et al. |
| 2022/0071826 | A1 | 3/2022 | Kulkarni et al. |
| 2022/0104965 | A1 | 4/2022 | Vaninetti et al. |
| 2022/0104976 | A1 | 4/2022 | Hoeger et al. |
| 2022/0104981 | A1 | 4/2022 | Jones |
| 2022/0117773 | A1 | 4/2022 | Davis et al. |
| 2022/0117774 | A1 | 4/2022 | Meyer et al. |
| 2022/0117775 | A1 | 4/2022 | Jones et al. |
| 2022/0118165 | A1 | 4/2022 | Knapp et al. |
| 2022/0133524 | A1 | 5/2022 | Davis |
| 2022/0151817 | A1 | 5/2022 | Mann |
| 2022/0160949 | A1 | 5/2022 | Simiele et al. |
| 2022/0168159 | A1 | 6/2022 | Triado et al. |
| 2022/0193312 | A1 | 6/2022 | Lee et al. |
| 2022/0211536 | A1 | 7/2022 | Johannes et al. |
| 2022/0218510 | A1 | 7/2022 | Metzger et al. |
| 2022/0229053 | A1 | 7/2022 | Levin et al. |
| 2022/0241106 | A1 | 8/2022 | Johannes et al. |
| 2022/0241115 | A1 | 8/2022 | Lang et al. |
| 2022/0247407 | A1 | 8/2022 | Yamamoto et al. |
| 2022/0248836 | A1 | 8/2022 | Cagle et al. |
| 2022/0257407 | A1 | 8/2022 | Johannes et al. |
| 2022/0265460 | A1 | 8/2022 | Coker |
| 2022/0265462 | A1 | 8/2022 | Alder et al. |
| 2022/0270711 | A1 | 8/2022 | Feala et al. |
| 2022/0273482 | A1 | 9/2022 | Johannes et al. |
| 2022/0280357 | A1 | 9/2022 | Jagannathan et al. |
| 2022/0280710 | A1 | 9/2022 | Agrawal et al. |
| 2022/0287689 | A1 | 9/2022 | Johannes |
| 2022/0287691 | A1 | 9/2022 | Wormser et al. |
| 2022/0287867 | A1 | 9/2022 | Jones et al. |
| 2022/0287868 | A1 | 9/2022 | Garvey et al. |
| 2022/0296406 | A1 | 9/2022 | Keelen |
| 2022/0296408 | A1 | 9/2022 | Evans et al. |
| 2022/0305191 | A1 | 9/2022 | Joseph et al. |
| 2022/0313222 | A1 | 10/2022 | Austermann et al. |
| 2022/0313474 | A1 | 10/2022 | Kriscovich et al. |
| 2022/0331170 | A1 | 10/2022 | Erdem et al. |
| 2022/0339023 | A1 | 10/2022 | Davis et al. |
| 2022/0339024 | A1 | 10/2022 | Johannes et al. |
| 2022/0354685 | A1 | 11/2022 | Davis et al. |
| 2022/0362049 | A1 | 11/2022 | Austermann et al. |
| 2022/0370231 | A1 | 11/2022 | Wang et al. |
| 2022/0370234 | A1 | 11/2022 | Hughett et al. |
| 2022/0370235 | A1 | 11/2022 | Johannes et al. |
| 2022/0370237 | A1 | 11/2022 | Parmar et al. |
| 2022/0387001 | A1 | 12/2022 | Askenazi et al. |
| 2022/0387693 | A1 | 12/2022 | Bannwart et al. |
| 2022/0395390 | A1 | 12/2022 | Brooks |
| 2022/0395391 | A1 | 12/2022 | Saunders et al. |
| 2022/0401252 | A1 | 12/2022 | Warren |
| 2022/0409419 | A1 | 12/2022 | Garvey et al. |
| 2022/0409422 | A1 | 12/2022 | Schneider et al. |
| 2023/0018845 | A1 | 1/2023 | Lee |
| 2023/0020563 | A1 | 1/2023 | Sharma et al. |
| 2023/0031640 | A1 | 2/2023 | Hughett et al. |
| 2023/0037159 | A1 | 2/2023 | Brennan et al. |
| 2023/0049924 | A1 | 2/2023 | Johannes et al. |
| 2023/0052238 | A1 | 2/2023 | Oluwasogo |
| 2023/0062994 | A1 | 3/2023 | Ecklund et al. |
| 2023/0070347 | A1 | 3/2023 | Watson et al. |
| 2023/0073708 | A1 | 3/2023 | Xu et al. |
| 2023/0089032 | A1 | 3/2023 | Hughett et al. |
| 2023/0091118 | A1 | 3/2023 | Watson |
| 2023/0099821 | A1 | 3/2023 | Radl et al. |
| 2023/0099991 | A1 | 3/2023 | Bianchi et al. |
| 2023/0105001 | A1 | 4/2023 | Whittome et al. |
| 2023/0110577 | A1 | 4/2023 | Choi |
| 2023/0138269 | A1 | 5/2023 | Abdelal et al. |
| 2023/0145365 | A1 | 5/2023 | Martin et al. |
| 2023/0155253 | A1 | 5/2023 | Yin et al. |
| 2023/0190511 | A1 | 6/2023 | Sharma et al. |
| 2023/0210504 | A1 | 7/2023 | Kuroda et al. |
| 2023/0210685 | A1 | 7/2023 | Fallows et al. |
| 2023/0218426 | A1 | 7/2023 | Hughett |
| 2023/0240884 | A1 | 8/2023 | Davis et al. |
| 2023/0248562 | A1 | 8/2023 | Sanchez et al. |
| 2023/0248564 | A1 | 8/2023 | Mann et al. |
| 2023/0255812 | A1 | 8/2023 | Sanchez et al. |
| 2023/0255813 | A1 | 8/2023 | Sanchez et al. |
| 2023/0255815 | A1 | 8/2023 | Newton |
| 2023/0263650 | A1 | 8/2023 | Sanchez et al. |
| 2023/0263655 | A1 | 8/2023 | Johannes et al. |
| 2023/0277360 | A1 | 9/2023 | Lambert et al. |
| 2023/0277362 | A1 | 9/2023 | Davis et al. |
| 2023/0285178 | A1 | 9/2023 | Sanchez et al. |
| 2023/0293339 | A1 | 9/2023 | James |
| 2023/0301846 | A1 | 9/2023 | Greenwood |
| 2023/0355423 | A1 | 11/2023 | Stevenson et al. |
| 2023/0389900 | A1 | 12/2023 | Xie et al. |
| 2023/0404791 | A1 | 12/2023 | Ecklund et al. |
| 2024/0000617 | A1 | 1/2024 | Locke |
| 2024/0008444 | A1 | 1/2024 | Su et al. |
| 2024/0009023 | A1 | 1/2024 | Johannes et al. |
| 2024/0024170 | A1 | 1/2024 | Scott |
| 2024/0033148 | A1 | 2/2024 | Gordon et al. |
| 2024/0041638 | A1 | 2/2024 | Johannes et al. |
| 2024/0058157 | A1 | 2/2024 | Davis |
| 2024/0058160 | A1 | 2/2024 | Young Joyner et al. |
| 2024/0058161 | A1 | 2/2024 | Ulreich et al. |
| 2024/0058520 | A1 | 2/2024 | Yin et al. |
| 2024/0065881 | A1 | 2/2024 | Kuroda et al. |
| 2024/0082044 | A1 | 3/2024 | Nguyen et al. |
| 2024/0099874 | A1 | 3/2024 | Sanchez et al. |
| 2024/0108268 | A1 | 4/2024 | Woodard et al. |
| 2024/0110318 | A1 | 4/2024 | Bendt et al. |
| 2024/0122773 | A1 | 4/2024 | Nguyen et al. |
| 2024/0123134 | A1 | 4/2024 | Kharkar et al. |
| 2024/0130885 | A1 | 4/2024 | Young Joyner et al. |
| 2024/0148539 | A1 | 5/2024 | Austermann et al. |
| 2024/0156633 | A1 | 5/2024 | Fallows et al. |
| 2024/0164935 | A1 | 5/2024 | Newton |
| 2024/0164937 | A1 | 5/2024 | Gloeckner et al. |
| 2024/0180737 | A1 | 6/2024 | Newton |
| 2024/0252343 | A1 | 8/2024 | Voda |
| 2024/0261131 | A1 | 8/2024 | Garvey et al. |
| 2024/0268986 | A1 | 8/2024 | Barnes et al. |
| 2024/0268989 | A1 | 8/2024 | Martin et al. |
| 2024/0268991 | A1 | 8/2024 | Davis |
| 2024/0269027 | A1 | 8/2024 | Tourchak et al. |
| 2024/0285425 | A1 | 8/2024 | Donohoe et al. |
| 2024/0325190 | A1 | 10/2024 | Minchew et al. |
| 2024/0335599 | A1 | 10/2024 | Cheng et al. |
| 2024/0341998 | A1 | 10/2024 | Julian et al. |
| 2024/0358539 | A1 | 10/2024 | Gallup |
| 2024/0358542 | A1 | 10/2024 | Richardson et al. |

(56) References Cited

U.S. PATENT DOCUMENTS

| | | | |
|---|---|---|---|
| 2024/0374414 | A1 | 11/2024 | Richardson et al. |
| 2025/0009552 | A1 | 1/2025 | Blabas et al. |
| 2025/0017761 | A1 | 1/2025 | Lee |
| 2025/0073055 | A1 | 3/2025 | Ecklund et al. |
| 2025/0107920 | A1 | 4/2025 | Fallows et al. |
| 2025/0107921 | A1 | 4/2025 | Sanchez et al. |
| 2025/0367358 | A1 | 12/2025 | Smith et al. |
| 2026/0020972 | A1 | 1/2026 | Godinez et al. |

FOREIGN PATENT DOCUMENTS

| | | | |
|---|---|---|---|
| AU | 2022349367 | A1 | 4/2024 |
| CA | 2165286 | C | 9/1999 |
| CA | 2335223 | A1 | 1/2000 |
| CA | 2354132 | A1 | 6/2000 |
| CA | 2359091 | C | 9/2003 |
| CA | 2488867 | C | 8/2007 |
| CA | 3031934 | A1 | 2/2018 |
| CA | 3050918 | A1 | 8/2018 |
| CA | 3098571 | A1 | 11/2019 |
| CA | 3144181 | A1 | 1/2021 |
| CA | 3188651 | A1 | 7/2023 |
| CN | 2269203 | Y | 12/1997 |
| CN | 1332620 | A | 1/2002 |
| CN | 1434693 | A | 8/2003 |
| CN | 2569779 | Y | 9/2003 |
| CN | 1533755 | A | 10/2004 |
| CN | 1579348 | A | 2/2005 |
| CN | 1602825 | A | 4/2005 |
| CN | 1638708 | A | 7/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451607 | A | 3/2016 |
| CN | 105451693 | A | 3/2016 |
| CN | 105534632 | A | 5/2016 |
| CN | 105616072 | A | 6/2016 |
| CN | 106132360 | A | 11/2016 |
| CN | 106137631 | A | 11/2016 |
| CN | 205849719 | U | 1/2017 |
| CN | 205924282 | U | 2/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 207785556 | U | 8/2018 |
| CN | 110171118 | A | 8/2019 |
| CN | 209285902 | U | 8/2019 |
| CN | 110381883 | A | 10/2019 |
| CN | 111465375 | A | 7/2020 |
| CN | 211198839 | U | 8/2020 |
| CN | 111991136 | A | 11/2020 |
| CN | 112022488 | A | 12/2020 |
| CN | 212234893 | U | 12/2020 |
| CN | 112384178 | A | 2/2021 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 1516466 | A1 | 6/1969 |
| DE | 2721330 | A1 | 11/1977 |
| DE | 2742298 | A1 | 3/1978 |
| DE | 3104356 | A1 | 9/1982 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 202005013173 | U1 | 6/2006 |
| DE | 102005037762 | B3 | 9/2006 |
| DE | 202006018506 | U1 | 3/2007 |
| DE | 102011103783 | A1 | 12/2012 |
| DE | 102012112818 | A1 | 6/2014 |
| DE | 202015104597 | U1 | 7/2016 |
| DE | 102018118570 | A1 | 2/2020 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0711536 | A1 | 5/1996 |
| EP | 0613355 | B1 | 1/1997 |
| EP | 0680296 | B1 | 5/1997 |
| EP | 0787472 | A1 | 8/1997 |
| EP | 0945231 | A2 | 9/1999 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2470251 | B1 | 12/2014 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3749230 | B1 | 3/2023 |
| EP | 3569205 | B1 | 6/2023 |
| EP | 4192402 | A1 | 6/2023 |
| EP | 4218702 | A1 | 8/2023 |
| EP | 3624742 | B1 | 1/2024 |
| EP | 4382082 | A2 | 6/2024 |
| EP | 4445881 | A2 | 10/2024 |
| EP | 4464288 | A2 | 11/2024 |
| EP | 4215134 | B1 | 1/2025 |
| EP | 4494611 | A2 | 1/2025 |
| EP | 4527361 | A2 | 3/2025 |
| EP | 4294336 | B1 | 9/2025 |
| FR | 2294812 | A1 | 7/1976 |
| FR | 2826704 | A1 | 1/2003 |
| GB | 871820 | A | 7/1961 |
| GB | 0873045 | A | 7/1961 |
| GB | 996370 | A | 6/1965 |

(56) References Cited

FOREIGN PATENT DOCUMENTS

| | | | |
|---|---|---|---|
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58130026 | A | 8/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0625981 | U | 4/1994 |
| JP | H0626264 | U | 4/1994 |
| JP | 3087938 | B2 | 10/1995 |
| JP | H085630 | A | 1/1996 |
| JP | H08117271 | A | 5/1996 |
| JP | H08510924 | A | 11/1996 |
| JP | 2686634 | B2 | 12/1997 |
| JP | H1038669 | A | 2/1998 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 2005323842 | A | 11/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2008278928 | A | 11/2008 |
| JP | 2009500111 | A | 1/2009 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012522014 | A | 9/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022536986 | A | 8/2022 |
| JP | 2022540178 | A | 9/2022 |
| JP | 2022554252 | A | 12/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |

(56) References Cited

FOREIGN PATENT DOCUMENTS

| | | | | |
|---|---|---|---|---|
| KR | 20090104426 | A | 10/2009 | |
| KR | 20090110359 | A | 10/2009 | |
| KR | 20100137210 | A | 12/2010 | |
| KR | 101035745 | B1 | 5/2011 | |
| KR | 20120005922 | A | 1/2012 | |
| KR | 20140039485 | A | 4/2014 | |
| KR | 101432639 | B1 | 8/2014 | |
| KR | 20180022173 | A | 3/2018 | |
| KR | 200486827 | Y1 | 7/2018 | |
| KR | 20180106659 | A | 10/2018 | |
| KR | 20180108774 | A | 10/2018 | |
| KR | 101976679 | B1 | 5/2019 | |
| KR | 101998130 | B1 | 7/2019 | |
| KR | 20230034343 | A | 3/2023 | |
| PT | 2068717 | E | 6/2013 | |
| SE | 505542 | C2 | 9/1997 | |
| TW | 408207 | B | 10/2000 | |
| TW | 202123903 | A | 7/2021 | |
| WO | 8101957 | A1 | 7/1981 | |
| WO | 8804558 | A1 | 6/1988 | |
| WO | 9104714 | A2 | 4/1991 | |
| WO | 9104714 | A3 | 6/1991 | |
| WO | 9220299 | A3 | 2/1993 | |
| WO | 9303690 | A1 | 3/1993 | |
| WO | 9307839 | A1 | 4/1993 | |
| WO | 9309736 | A2 | 5/1993 | |
| WO | 9309736 | A3 | 6/1993 | |
| WO | 9416914 | A1 | 8/1994 | |
| WO | 9514448 | A2 | 6/1995 | |
| WO | 9600096 | A1 | 1/1996 | |
| WO | 9634636 | A1 | 11/1996 | |
| WO | 9817211 | A1 | 4/1998 | |
| WO | 9830336 | A1 | 7/1998 | |
| WO | 0000112 | A1 | 1/2000 | |
| WO | 0000113 | A1 | 1/2000 | |
| WO | 0025651 | A1 | 5/2000 | |
| WO | 0033773 | A1 | 6/2000 | |
| WO | 0057784 | A1 | 10/2000 | |
| WO | 0069377 | A1 | 11/2000 | |
| WO | 0079497 | A1 | 12/2000 | |
| WO | 0145618 | A1 | 6/2001 | |
| WO | 0145621 | A1 | 6/2001 | |
| WO | 02094160 | A1 | 11/2002 | |
| WO | 03013967 | A1 | 2/2003 | |
| WO | 03015671 | A1 | 2/2003 | |
| WO | 03024824 | A1 | 3/2003 | |
| WO | 03055423 | A1 | 7/2003 | |
| WO | 03071931 | A2 | 9/2003 | |
| WO | 03079942 | A1 | 10/2003 | |
| WO | 03071931 | A3 | 2/2004 | |
| WO | 2004019836 | A1 | 3/2004 | |
| WO | 2004024046 | A1 | 3/2004 | |
| WO | 2004026195 | A1 | 4/2004 | |
| WO | 2005003725 | A2 | 1/2005 | |
| WO | 2005051252 | A1 | 6/2005 | |
| WO | 2005060558 | A2 | 7/2005 | |
| WO | 2005074571 | A3 | 9/2005 | |
| WO | 2005089687 | A2 | 9/2005 | |
| WO | 2005107661 | A2 | 11/2005 | |
| WO | 2006021220 | A1 | 3/2006 | |
| WO | 2006037140 | A2 | 4/2006 | |
| WO | 2007005851 | A2 | 1/2007 | |
| WO | 2007007845 | A1 | 1/2007 | |
| WO | 2007042823 | A2 | 4/2007 | |
| WO | 2007055651 | A1 | 5/2007 | |
| WO | 2006098950 | A3 | 11/2007 | |
| WO | 2007128156 | A3 | 2/2008 | |
| WO | 2008026106 | A2 | 3/2008 | |
| WO | 2008078117 | A1 | 7/2008 | |
| WO | 2008104019 | A1 | 9/2008 | |
| WO | 2008141471 | A1 | 11/2008 | |
| WO | 2009004368 | A1 | 1/2009 | |
| WO | 2009004369 | A1 | 1/2009 | |
| WO | 2009052496 | A1 | 4/2009 | |
| WO | 2009052502 | A1 | 4/2009 | |
| WO | 2009007702 | A4 | 7/2009 | |
| WO | 2009101738 | A1 | 8/2009 | |
| WO | 2010058192 | A1 | 5/2010 | |
| WO | 2010030122 | A3 | 7/2010 | |
| WO | 2010101915 | A3 | 1/2011 | |
| WO | 2011018132 | A1 | 2/2011 | |
| WO | 2011018133 | A1 | 2/2011 | |
| WO | 2011024864 | A1 | 3/2011 | |
| WO | 2011054118 | A1 | 5/2011 | |
| WO | 2011079132 | A1 | 6/2011 | |
| WO | 2011107972 | A1 | 9/2011 | |
| WO | 2011108972 | A1 | 9/2011 | |
| WO | 2011117292 | A1 | 9/2011 | |
| WO | 2011123219 | A1 | 10/2011 | |
| WO | 2011132043 | A1 | 10/2011 | |
| WO | 2012012908 | A1 | 2/2012 | |
| WO | 2012020506 | A1 | 2/2012 | |
| WO | 2012065274 | A1 | 5/2012 | |
| WO | 2012097462 | A1 | 7/2012 | |
| WO | 2012098796 | A1 | 7/2012 | |
| WO | 2012101288 | A1 | 8/2012 | |
| WO | 2012175916 | A1 | 12/2012 | |
| WO | 2013018435 | A1 | 2/2013 | |
| WO | 2013033429 | A1 | 3/2013 | |
| WO | 2013055434 | A1 | 4/2013 | |
| WO | 2013082397 | A1 | 6/2013 | |
| WO | 2013103291 | A2 | 7/2013 | |
| WO | 2013131109 | A1 | 9/2013 | |
| WO | 2013167478 | A1 | 11/2013 | |
| WO | 2013177716 | A1 | 12/2013 | |
| WO | 2014041534 | A1 | 3/2014 | |
| WO | 2014046420 | A1 | 3/2014 | |
| WO | 2014118518 | A1 | 8/2014 | |
| WO | 2014160852 | A1 | 10/2014 | |
| WO | 2015023599 | A1 | 2/2015 | |
| WO | 2015052348 | A1 | 4/2015 | |
| WO | 2015068384 | A1 | 5/2015 | |
| WO | 2015169403 | A1 | 11/2015 | |
| WO | 2015170307 | A1 | 11/2015 | |
| WO | 2015197462 | A1 | 12/2015 | |
| WO | 2016051385 | A1 | 4/2016 | |
| WO | 2016055989 | A1 | 4/2016 | |
| WO | 2016071894 | A1 | 5/2016 | |
| WO | 2016103242 | A1 | 6/2016 | |
| WO | 2016116915 | A1 | 7/2016 | |
| WO | 2016124203 | A1 | 8/2016 | |
| WO | 2016139448 | A1 | 9/2016 | |
| WO | 2016166562 | A1 | 10/2016 | |
| WO | 2016167535 | A1 | 10/2016 | |
| WO | 2016191574 | A1 | 12/2016 | |
| WO | 2016200088 | A1 | 12/2016 | |
| WO | 2016200361 | A1 | 12/2016 | |
| WO | 2016204731 | A1 | 12/2016 | |
| WO | 2017001532 | A2 | 1/2017 | |
| WO | WO-2017075226 | A1 * | 5/2017 | ........ A61M 25/0017 |
| WO | 2017100511 | A1 | 6/2017 | |
| WO | 2017152198 | A1 | 9/2017 | |
| WO | 2017153357 | A1 | 9/2017 | |
| WO | 2017162559 | A1 | 9/2017 | |
| WO | 2017205446 | A1 | 11/2017 | |
| WO | 2017209779 | A1 | 12/2017 | |
| WO | 2017210524 | A1 | 12/2017 | |
| WO | 2018022414 | A1 | 2/2018 | |
| WO | 2018044781 | A1 | 3/2018 | |
| WO | 2018056953 | A1 | 3/2018 | |
| WO | 2018090550 | A1 | 5/2018 | |
| WO | 2018138513 | A1 | 8/2018 | |
| WO | 2018144318 | A1 | 8/2018 | |
| WO | 2018144463 | A1 | 8/2018 | |
| WO | 2018150263 | A1 | 8/2018 | |
| WO | 2018150268 | A1 | 8/2018 | |
| WO | 2018152156 | A1 | 8/2018 | |
| WO | 2018183791 | A1 | 10/2018 | |
| WO | 2018150267 | A3 | 11/2018 | |
| WO | 2018200721 | A1 | 11/2018 | |
| WO | 2018235026 | A1 | 12/2018 | |
| WO | 2018235065 | A1 | 12/2018 | |
| WO | 2019004404 | A1 | 1/2019 | |
| WO | 2019038732 | A1 | 2/2019 | |

(56) References Cited

FOREIGN PATENT DOCUMENTS

| | | | |
|---|---|---|---|
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023146529 | A1 | 8/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025048789 | A1 | 3/2025 |
| WO | 2025071622 | A1 | 4/2025 |
| WO | 2025179267 | A1 | 8/2025 |
| WO | 2026035497 | A1 | 2/2026 |

OTHER PUBLICATIONS

Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/245,726 mailed Apr. 19, 2023.
Advisory Action for U.S. Appl. No. 16/369,676 mailed Mar. 24, 2023.

(56) References Cited

OTHER PUBLICATIONS

Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/452,258 mailed Oct. 26, 2022.
Advisory Action for U.S. Appl. No. 16/478,180 mailed Jun. 7, 2024.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/899,956 mailed Jul. 9, 2021.
Advisory Action for U.S. Appl. No. 16/904,868 mailed Jan. 2, 2024.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed Mar. 21, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/330,657 mailed Dec. 9, 2021.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/449,039 mailed Nov. 21, 2023.
Final Office Action for U.S. Appl. No. 16/452,145 mailed Mar. 25, 2022.
Final Office Action for U.S. Appl. No. 16/452,258 mailed Dec. 21, 2023.
Final Office Action for U.S. Appl. No. 16/452,258 mailed Jun. 14, 2022.
Final Office Action for U.S. Appl. No. 16/478,180 mailed Feb. 28, 2024.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/904,868 mailed Nov. 2, 2023.
Final Office Action for U.S. Appl. No. 16/905,400 mailed Apr. 6, 2021.

(56) References Cited

OTHER PUBLICATIONS

Final Office Action for U.S. Appl. No. 16/905,400 mailed Dec. 9, 2021.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/051,600 mailed Jun. 27, 2024.
Final Office Action for U.S. Appl. No. 17/088,272 mailed May 25, 2021.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
Final Office Action for U.S. Appl. No. 29/624,661 mailed Feb. 18, 2020.
International Search Report and Written Opinion from International Application No. PCT/IB2021/057173 mailed Nov. 5, 2021.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.

(56) References Cited

OTHER PUBLICATIONS

International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.

(56) References Cited

OTHER PUBLICATIONS

International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/077208 mailed May 10, 2024.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 16/245,726 mailed Oct. 18, 2023.
Issue Notification for U.S. Appl. No. 16/449,039 mailed Jun. 19, 2024.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 17/461,036 mailed Oct. 11, 2023.
Issue Notification for U.S. Appl. No. 17/657,474 mailed Jun. 19, 2024.
Issue Notification for U.S. Appl. No. 17/663,046 mailed Dec. 20, 2023.
Issue Notification for U.S. Appl. No. 18/299,788 mailed Feb. 21, 2024.
Issue Notification for U.S. Appl. No. 29/624,661 mailed Aug. 4, 2021.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Feb. 29, 2024.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/449,039 mailed Dec. 8, 2021.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,145 mailed Sep. 28, 2021.
Non-Final Office Action for U.S. Appl. No. 16/452,258 mailed Apr. 26, 2023.
Non-Final Office Action for U.S. Appl. No. 16/452,258 mailed Jun. 20, 2024.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Mar. 12, 2024.
Non-Final Office Action for U.S. Appl. No. 16/904,868 mailed Mar. 15, 2023.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/088,272 mailed Jan. 25, 2021.

(56) References Cited

OTHER PUBLICATIONS

Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/330,657 mailed Aug. 11, 2021.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/450,864 mailed May 29, 2024.
Non-Final Office Action for U.S. Appl. No. 17/451,345 mailed Dec. 7, 2022.
Non-Final Office Action for U.S. Appl. No. 17/451,345 mailed Jan. 17, 2024.
Non-Final Office Action for U.S. Appl. No. 17/451,354 mailed Apr. 4, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/645,821 mailed Oct. 25, 2023.
Non-Final Office Action for U.S. Appl. No. 17/646,771 mailed Apr. 24, 2024.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 14, 2023.
Non-Final Office Action for U.S. Appl. No. 17/655,464 mailed Mar. 26, 2024.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/661,090 mailed May 22, 2024.
Non-Final Office Action for U.S. Appl. No. 17/662,700 mailed Jul. 22, 2022.
Non-Final Office Action for U.S. Appl. No. 17/663,330 mailed Jun. 29, 2023.
Non-Final Office Action for U.S. Appl. No. 17/664,487 mailed Jun. 17, 2024.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Jun. 21, 2024.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/245,726 mailed Jul. 6, 2023.
Notice of Allowance for U.S. Appl. No. 16/369,676 mailed Jun. 17, 2024.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/449,039 mailed Mar. 28, 2024.
Notice of Allowance for U.S. Appl. No. 16/899,956 mailed Apr. 19, 2022.
Notice of Allowance for U.S. Appl. No. 16/899,956 mailed Aug. 10, 2022.

(56) References Cited

OTHER PUBLICATIONS

Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jul. 28, 2023.
Notice of Allowance for U.S. Appl. No. 17/662,700 mailed Jun. 12, 2024.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/198,464 mailed Apr. 17, 2024.
Notice of Allowance for U.S. Appl. No. 18/299,788 mailed Jul. 24, 2023.
Notice of Allowance for U.S. Appl. No. 18/299,788 mailed Nov. 6, 2023.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/527,769 mailed Jun. 17, 2024.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/444,792, filed Aug. 10, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.

(56) References Cited

OTHER PUBLICATIONS

U.S. Appl. No. 17/451,354, filed Oct. 19, 2021.
U.S. Appl. No. 17/451,719, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/073,545, filed Sep. 2, 2020.
U.S. Appl. No. 63/073,553, filed Sep. 2, 2020.

(56) References Cited

OTHER PUBLICATIONS

U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/150,640, filed Feb. 18, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
Defendant and Counterclaim Plaintiff Sage Products, Llc's Answer, Defenses, and Counterclaims to Plaintiff's Amended Complaint, Nov. 1, 2019.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
Memorandum Order, Feb. 2021.
Sage's Initial Invalidity Contentions Regarding U.S. Pat. Nos. 8,287,508; 10,226,375; and 10,390,989, May 29, 2020.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020.
Sage's Second Supplemental Invalidity Contentions Regarding U.S. Pat. Nos. 8,287,508, 10,226,375, 10,390,989, and 10,376,407.
Boehringer CareDry System—Second Generation for Non-Invasive Urinary Management for Females, Mar. 2021.
*PureWick Corporation* v. *Sage Products, LLC* Transcripts vol. 5, Apr. 1, 2022.
Excerpts from the 508 (U.S. Pat. No. 8,278,508) Patent's Prosecution History, 2020.
*PureWick Corporation* v. *Sage Products, LLC* Transcripts vol. 1, Mar. 28, 2022.
Plaintiff's Opening Claim Construction Brief, Oct. 16, 2020.
Plaintiff's Identification of Claim Terms and Proposed Constructions.
PureWick's Response to Interrogatory No. 9 in *PureWick, LLC* v. *Sage Products, LLC*, Mar. 23, 2020.
Sage's Preliminary Identification of Claim Elements and Proposed Constructions for U.S. Pat. Nos. 8,287,508, 10,226,376, 10,390,989 and 10,376,407.
Decision Granting Institution of Inter Partes Review for U.S. Pat. No. 8,287,508, Feb. 17, 2021.
Corrected Certificate of Service, 2020.
Declaration of Diane K. Newman Curriculum Vitae, 2020.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit", Omni Medical Systems, Inc., 1 page.
"AMXD Control Starter Kit Brochure", https://www.omnimedicalsys.com/index.php?page=products, 8 pages.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"Combat Force Multiplier in Flight Bladder Relief Cockpit Essential Equipment Brochure", Omni Medical, 20 pages.
"External Urine Management for Female Anatomy", https://www.stryker.com/us/en/sage/products/sage-primafit.html, Jul. 2020, 4 pages.
"GSA Price List", Omni Medical, Apr. 2011, 2 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"How Period Panties Work", www.shethinx.com/pages/thinx-itworks, 2020, 10 pages.

(56) References Cited

OTHER PUBLICATIONS

"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Letter to Mark Harvie of Omni Measurement Systems", Department of Veterans Affairs, Nov. 1, 2007, 11 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Oblong", Cambridge Dictionary, https://dictionary.cambridge.org/dictionary/english/oblong, 2024, 1 page.
"Research and Development Work Relating to Assistive Technology 2005-06", British Department of Health, Nov. 2006, 40 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover—Catheter Bag Cover 2000 ml Volume—Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Britannica, "Polyolefin", Britannica Online Encyclopedia, T. Editors of Encyclopaedia, https://www.britannica.com/science/polyolefin, Jul. 26, 2012.
Cañas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hollister, "Female Urinary and Pouch and Male Urinary Pouch Brochure", www.hollister.com, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister, "Retracted Penis Pouch by Hollister", Vitality Medical.com.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Macaulay, et al., "A Noninvasive Continence Management System: Development and Evaluation of a Novel Toileting Device for Women", The Wound, Ostomy and Continence Nurses Society, 2007, pp. 641-648.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Merriam-Webster Dictionary,, "Embed Definition & Meaning", https://www.merriam-webster.com/dictionary/embed last accessed Aug. 3, 2023, 2003.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", , 11 pages.
Parmar, "10 Finalists Chosen for Dare-to-Dream Medtech Design Challenge (PureWick)", Design Services, Nov. 10, 2014, 3 pages.
Parness, et al., "A microfabricated wedge-shaped adhesive array displaying gecko-like dynamic adhesion, directionality", J.R. Soc. Interface, 2009, pp. 1223-1232.
Pieper, et al., "An external urine-collection device for women: A clinical trial", Journal of ER Nursing, vol. 20, No. 2, Mar./Apr. 1993, pp. 51-55.
Purewick, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
Tsipenyuk, et al., "Use of biomimetic hexagonal surface texture in friction against lubricated skin", Journal of the Royal Society—Interface, 2014, pp. 1-6.
Vinas, "A Solution for an Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article, "Decibel", https://web.archive.org/web/20200415211917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
"Abut Definition & Meaning", Dictionary.com, https://www.dictionary.com/browse/abut, 2024, 1 page.
"Proximate Definition & Meaning" <https://www.merriam-webster.com/dictionary/> 2025.
"Surface Energy Data for Cellulose acetate, CAS # 9004-35-7", Diviersified Enterprises, 2009, 1 page.
"Tube Definition & Meaning" Merriam Webster Dictionary, 2025, <https://www.merriam-webster.com/dictionary/tube>.
Advisory Action for U.S. Appl. No. 16/452,258 mailed Apr. 17, 2026.
Advisory Action for U.S. Appl. No. 16/452,258 mailed May 5, 2025.
Advisory Action for U.S. Appl. No. 17/051,585 mailed Oct. 8, 2024.
Advisory Action for U.S. Appl. No. 17/378,015 mailed Oct. 28, 2025.
Advisory Action for U.S. Appl. No. 17/394,055 mailed Jan. 9, 2026.
Advisory Action for U.S. Appl. No. 17/446,256 mailed Nov. 19, 2024.
Advisory Action for U.S. Appl. No. 17/446,256 mailed Nov. 6, 2025.

(56) References Cited

OTHER PUBLICATIONS

Advisory Action for U.S. Appl. No. 17/446,654 mailed Apr. 16, 2026.
Advisory Action for U.S. Appl. No. 17/446,654 mailed Feb. 28, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/597,673 mailed Jan. 7, 2025.
Advisory Action for U.S. Appl. No. 17/653,137 mailed Nov. 20, 2024.
Advisory Action for U.S. Appl. No. 17/653,314 mailed Apr. 8, 2025.
Advisory Action for U.S. Appl. No. 17/653,920 mailed Oct. 28, 2024.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/664,487 mailed Apr. 9, 2026.
Advisory Action for U.S. Appl. No. 17/757,311 mailed Jul. 2, 2025.
Advisory Action for U.S. Appl. No. 17/929,887 mailed Apr. 16, 2026.
Advisory Action for U.S. Appl. No. 17/933,590 mailed Jun. 2, 2026.
Advisory Action for U.S. Appl. No. 18/003,029 mailed Jan. 8, 2025.
Advisory Action for U.S. Appl. No. 18/006,807 mailed May 4, 2026.
Advisory Action for U.S. Appl. No. 18/042,842 mailed Apr. 14, 2026.
Advisory Action for U.S. Appl. No. 18/134,857 mailed Oct. 23, 2024.
Advisory Action for U.S. Appl. No. 18/164,800 mailed Apr. 9, 2026.
Advisory Action for U.S. Appl. No. 18/164,800 mailed Jan. 8, 2025.
Advisory Action for U.S. Appl. No. 18/247,986 mailed Apr. 1, 2026.
Advisory Action for U.S. Appl. No. 18/265,736 mailed Mar. 4, 2026.
Corrected Notice of Allowability for U.S. Appl. No. 17/444,792 mailed Jun. 24, 2025.
Corrected Notice of Allowability for U.S. Appl. No. 17/450,864 mailed Oct. 24, 2024.
Corrected Notice of Allowability for U.S. Appl. No. 17/646,771 mailed Jan. 17, 2025.
Corrected Notice of Allowability for U.S. Appl. No. 17/653,314 mailed Oct. 29, 2025.
Corrected Notice of Allowability for U.S. Appl. No. 17/754,736 mailed Feb. 12, 2026.
Corrected Notice of Allowability for U.S. Appl. No. 17/808,354 mailed Nov. 25, 2025.
Corrected Notice of Allowability for U.S. Appl. No. 17/996,253 mailed Apr. 28, 2025.
Corrected Notice of Allowability for U.S. Appl. No. 18/041,109 mailed Apr. 2, 2026.
Corrected Notice of Allowability for U.S. Appl. No. 18/134,857 mailed Mar. 14, 2025.
Corrected Notice of Allowability for U.S. Appl. No. 18/249,577 mailed Apr. 15, 2026.
Corrected Notice of Allowability for U.S. Appl. No. 18/260,122 mailed Aug. 11, 2025.
Corrected Notice of Allowability for U.S. Appl. No. 18/264,004 mailed Feb. 10, 2026.
Corrected Notice of Allowability for U.S. Appl. No. 18/264,004 mailed Feb. 3, 2026.
Corrected Notice of Allowability for U.S. Appl. No. 18/294,370 mailed Mar. 31, 2026.
Corrected Notice of Allowability for U.S. Appl. No. 18/426,795 mailed Dec. 4, 2024.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 16/452,258 mailed Feb. 11, 2026.
Final Office Action for U.S. Appl. No. 16/452,258 mailed Jan. 6, 2025.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 18, 2024.
Final Office Action for U.S. Appl. No. 17/446,654 mailed Dec. 22, 2025.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/595,747 mailed Feb. 19, 2026.
Final Office Action for U.S. Appl. No. 17/597,408 mailed Mar. 24, 2025.
Final Office Action for U.S. Appl. No. 17/597,673 mailed Oct. 22, 2024.
Final Office Action for U.S. Appl. No. 17/614,173 mailed May 20, 2025.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/628,411 mailed Apr. 7, 2026.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,314 mailed Jan. 30, 2025.
Final Office Action for U.S. Appl. No. 17/653,920 mailed Apr. 24, 2025.
Final Office Action for U.S. Appl. No. 17/655,464 mailed Feb. 17, 2026.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/757,311 mailed Mar. 31, 2025.
Final Office Action for U.S. Appl. No. 17/758,152 mailed Apr. 7, 2026.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/809,083 mailed Jan. 23, 2026.
Final Office Action for U.S. Appl. No. 17/907,125 mailed Apr. 30, 2025.
Final Office Action for U.S. Appl. No. 17/929,887 mailed Jan. 13, 2026.
Final Office Action for U.S. Appl. No. 17/933,590 mailed Feb. 19, 2026.
Final Office Action for U.S. Appl. No. 18/003,029 mailed Nov. 26, 2025.

(56) References Cited

OTHER PUBLICATIONS

Final Office Action for U.S. Appl. No. 18/003,029 mailed Oct. 22, 2024.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/043,618 mailed Nov. 26, 2025.
Final Office Action for U.S. Appl. No. 18/115,444 mailed May 19, 2026.
Final Office Action for U.S. Appl. No. 18/139,523 mailed May 8, 2025.
Final Office Action for U.S. Appl. No. 18/150,360 mailed Apr. 10, 2026.
Final Office Action for U.S. Appl. No. 18/164,800 mailed Dec. 5, 2025.
Final Office Action for U.S. Appl. No. 18/164,800 mailed Oct. 22, 2024.
Final Office Action for U.S. Appl. No. 18/247,986 mailed Jan. 7, 2026.
Final Office Action for U.S. Appl. No. 18/254,638 mailed Apr. 8, 2026.
Final Office Action for U.S. Appl. No. 18/265,736 mailed Dec. 1, 2025.
Final Office Action for U.S. Appl. No. 18/548,152 mailed Apr. 15, 2026.
Final Office Action for U.S. Appl. No. 18/556,945 mailed May 29, 2026.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
International Search Report and Written Opinion from International Application No. PCT/US2023/031432 mailed Feb. 29, 2024.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
International Search Report and Written Opinion from International Application No. PCT/US2025/035383 mailed Oct. 10, 2025.
Issue Notification for U.S. Appl. No. 16/369,676 mailed Oct. 2, 2024.
Issue Notification for U.S. Appl. No. 16/433,773 mailed Jan. 21, 2026.
Issue Notification for U.S. Appl. No. 16/452,145 mailed Oct. 23, 2024.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,399 mailed Mar. 4, 2026.
Issue Notification for U.S. Appl. No. 17/051,585 mailed Mar. 26, 2025.
Issue Notification for U.S. Appl. No. 17/051,600 mailed Apr. 29, 2026.
Issue Notification for U.S. Appl. No. 17/179,116 mailed Dec. 25, 2024.
Issue Notification for U.S. Appl. No. 17/444,792 mailed Jun. 25, 2025.
Issue Notification for U.S. Appl. No. 17/447,123 mailed Nov. 13, 2024.
Issue Notification for U.S. Appl. No. 17/450,864 mailed Jan. 8, 2025.
Issue Notification for U.S. Appl. No. 17/451,354 mailed Feb. 25, 2026.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/625,941 mailed Feb. 25, 2026.
Issue Notification for U.S. Appl. No. 17/645,821 mailed Apr. 1, 2026.
Issue Notification for U.S. Appl. No. 17/646,771 mailed Mar. 19, 2025.
Issue Notification for U.S. Appl. No. 17/653,137 mailed Feb. 4, 2025.
Issue Notification for U.S. Appl. No. 17/653,314 mailed Feb. 11, 2026.
Issue Notification for U.S. Appl. No. 17/653,920 mailed Oct. 22, 2025.
Issue Notification for U.S. Appl. No. 17/661,090 mailed Feb. 5, 2025.
Issue Notification for U.S. Appl. No. 17/662,700 mailed Oct. 23, 2024.
Issue Notification for U.S. Appl. No. 17/663,330 mailed Feb. 26, 2025.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/759,697 mailed May 6, 2026.
Issue Notification for U.S. Appl. No. 17/808,354 mailed Mar. 4, 2026.
Issue Notification for U.S. Appl. No. 17/878,268 mailed Feb. 4, 2026.
Issue Notification for U.S. Appl. No. 17/907,125 mailed Dec. 30, 2025.
Issue Notification for U.S. Appl. No. 17/912,147 mailed Mar. 18, 2026.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/044,413 mailed Dec. 30, 2025.
Issue Notification for U.S. Appl. No. 18/134,857 mailed May 28, 2025.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/260,122 mailed Nov. 12, 2025.

(56) References Cited

OTHER PUBLICATIONS

Issue Notification for U.S. Appl. No. 18/389,009 mailed Dec. 18, 2024.
Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Laerdal Medical, "LSCU 4—Laerdal Compact Suction Unit", Aug. 17, 2012, Youtube, https://www.youtube.com/watch?v= EWCAcc-Crwys.
Non-Final Office Action for U.S. Appl. No. 16/433,773 mailed Feb. 28, 2025.
Non-Final Office Action for U.S. Appl. No. 16/452,258 mailed Jun. 3, 2026.
Non-Final Office Action for U.S. Appl. No. 16/452,258 mailed Sep. 24, 2025.
Non-Final Office Action for U.S. Appl. No. 17/051,600 mailed Feb. 28, 2025.
Non-Final Office Action for U.S. Appl. No. 17/378,015 mailed Dec. 12, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,256 mailed Dec. 2, 2025.
Non-Final Office Action for U.S. Appl. No. 17/446,654 mailed May 1, 2025.
Non-Final Office Action for U.S. Appl. No. 17/446,654 mailed May 14, 2026.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/597,408 mailed Apr. 7, 2026.
Non-Final Office Action for U.S. Appl. No. 17/614,173 mailed Dec. 29, 2025.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Dec. 22, 2025.
Non-Final Office Action for U.S. Appl. No. 17/628,411 mailed Sep. 23, 2024.
Non-Final Office Action for U.S. Appl. No. 17/631,619 mailed Mar. 19, 2025.
Non-Final Office Action for U.S. Appl. No. 17/635,866 mailed Jul. 29, 2025.
Non-Final Office Action for U.S. Appl. No. 17/645,821 mailed Mar. 31, 2025.
Non-Final Office Action for U.S. Appl. No. 17/653,137 mailed Jan. 28, 2025.
Non-Final Office Action for U.S. Appl. No. 17/653,314 mailed May 8, 2025.
Non-Final Office Action for U.S. Appl. No. 17/653,920 mailed Nov. 27, 2024.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/757,311 mailed Oct. 22, 2024.
Non-Final Office Action for U.S. Appl. No. 17/757,311 mailed Sep. 2, 2025.
Non-Final Office Action for U.S. Appl. No. 17/758,152 mailed Apr. 8, 2025.
Non-Final Office Action for U.S. Appl. No. 17/759,587 mailed Jan. 26, 2026.
Non-Final Office Action for U.S. Appl. No. 17/759,697 mailed Dec. 4, 2024.
Non-Final Office Action for U.S. Appl. No. 17/759,697 mailed Sep. 17, 2025.
Non-Final Office Action for U.S. Appl. No. 17/808,354 mailed Dec. 13, 2024.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/809,083 mailed May 21, 2026.
Non-Final Office Action for U.S. Appl. No. 17/878,268 mailed Mar. 17, 2025.
Non-Final Office Action for U.S. Appl. No. 17/907,125 mailed Dec. 13, 2024.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 17/996,064 mailed Mar. 6, 2025.
Non-Final Office Action for U.S. Appl. No. 17/996,556 mailed Dec. 22, 2025.
Non-Final Office Action for U.S. Appl. No. 18/003,029 mailed Apr. 18, 2025.
Non-Final Office Action for U.S. Appl. No. 18/003,029 mailed Apr. 20, 2026.
Non-Final Office Action for U.S. Appl. No. 18/006,807 mailed May 29, 2025.
Non-Final Office Action for U.S. Appl. No. 18/034,902 mailed Mar. 20, 2026.
Non-Final Office Action for U.S. Appl. No. 18/042,842 mailed May 22, 2025.
Non-Final Office Action for U.S. Appl. No. 18/043,618 mailed May 1, 2026.
Non-Final Office Action for U.S. Appl. No. 18/043,618 mailed May 19, 2025.
Non-Final Office Action for U.S. Appl. No. 18/043,807 mailed Feb. 10, 2026.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/164,800 mailed Apr. 25, 2025.
Non-Final Office Action for U.S. Appl. No. 18/246,121 mailed Jan. 22, 2026.
Non-Final Office Action for U.S. Appl. No. 18/247,986 mailed Jun. 4, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jan. 30, 2026.

(56) References Cited

OTHER PUBLICATIONS

Non-Final Office Action for U.S. Appl. No. 18/259,626 mailed Jul. 11, 2025.
Non-Final Office Action for U.S. Appl. No. 18/260,391 mailed Apr. 29, 2026.
Non-Final Office Action for U.S. Appl. No. 18/260,394 mailed Jan. 13, 2026.
Non-Final Office Action for U.S. Appl. No. 18/263,800 mailed Feb. 5, 2026.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/265,736 mailed Jun. 2, 2026.
Non-Final Office Action for U.S. Appl. No. 18/294,403 mailed May 15, 2026.
Non-Final Office Action for U.S. Appl. No. 18/335,579 mailed Apr. 24, 2026.
Non-Final Office Action for U.S. Appl. No. 18/373,424 mailed Jun. 3, 2026.
Non-Final Office Action for U.S. Appl. No. 18/376,274 mailed Mar. 9, 2026.
Non-Final Office Action for U.S. Appl. No. 18/546,465 mailed Apr. 1, 2026.
Non-Final Office Action for U.S. Appl. No. 18/548,152 mailed Sep. 16, 2025.
Non-Final Office Action for U.S. Appl. No. 18/549,387 mailed Mar. 4, 2026.
Non-Final Office Action for U.S. Appl. No. 18/549,658 mailed May 29, 2026.
Non-Final Office Action for U.S. Appl. No. 18/551,492 mailed Mar. 19, 2026.
Non-Final Office Action for U.S. Appl. No. 18/553,625 mailed Oct. 2, 2025.
Non-Final Office Action for U.S. Appl. No. 18/556,945 mailed Dec. 19, 2025.
Non-Final Office Action for U.S. Appl. No. 18/562,626 mailed Feb. 11, 2026.
Non-Final Office Action for U.S. Appl. No. 18/563,672 mailed Feb. 12, 2026.
Non-Final Office Action for U.S. Appl. No. 18/569,711 mailed Mar. 30, 2026.
Non-Final Office Action for U.S. Appl. No. 18/569,778 mailed May 1, 2026.
Non-Final Office Action for U.S. Appl. No. 18/662,216 mailed Mar. 9, 2026.
Non-Final Office Action for U.S. Appl. No. 18/681,987 mailed Mar. 30, 2026.
Non-Final Office Action for U.S. Appl. No. 18/682,006 mailed Mar. 4, 2026.
Non-Final Office Action for U.S. Appl. No. 18/689,532 mailed Mar. 19, 2026.
Non-Final Office Action for U.S. Appl. No. 18/690,392 mailed Feb. 9, 2026.
Non-Final Office Action for U.S. Appl. No. 18/694,090 mailed Mar. 17, 2026.
Non-Final Office Action for U.S. Appl. No. 18/757,964 mailed Aug. 20, 2025.
Non-Final Office Action for U.S. Appl. No. 18/757,964 mailed Mar. 27, 2026.
Non-Final Office Action for U.S. Appl. No. 18/834,176 mailed May 18, 2026.
Non-Final Office Action for U.S. Appl. No. 18/835,068 mailed May 19, 2026.
Non-Final Office Action for U.S. Appl. No. 18/835,444 mailed Apr. 24, 2026.
Non-Final Office Action for U.S. Appl. No. 18/836,204 mailed Jun. 9, 2026.
Non-Final Office Action for U.S. Appl. No. 19/237,368 mailed Apr. 6, 2026.
Non-Final Office Action for U.S. Appl. No. 19/353,151 mailed May 15, 2026.
Non-Final Office Action for U.S. Appl. No. 29/892,478 mailed Mar. 12, 2026.
Notice of Allowance for U.S. Appl. No. 16/433,773 mailed Oct. 10, 2025.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,399 mailed Nov. 17, 2025.
Notice of Allowance for U.S. Appl. No. 17/051,585 mailed Dec. 26, 2024.
Notice of Allowance for U.S. Appl. No. 17/051,600 mailed Jan. 5, 2026.
Notice of Allowance for U.S. Appl. No. 17/378,015 mailed Jun. 8, 2026.
Notice of Allowance for U.S. Appl. No. 17/394,055 mailed Mar. 20, 2026.
Notice of Allowance for U.S. Appl. No. 17/444,792 mailed Mar. 28, 2025.
Notice of Allowance for U.S. Appl. No. 17/451,345 mailed Jun. 24, 2025.
Notice of Allowance for U.S. Appl. No. 17/451,354 mailed Nov. 18, 2025.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.
Notice of Allowance for U.S. Appl. No. 17/596,629 mailed May 27, 2025.
Notice of Allowance for U.S. Appl. No. 17/597,673 mailed Feb. 26, 2025.
Notice of Allowance for U.S. Appl. No. 17/614,173 mailed May 7, 2026.
Notice of Allowance for U.S. Appl. No. 17/625,887 mailed Mar. 3, 2026.
Notice of Allowance for U.S. Appl. No. 17/625,941 mailed Nov. 13, 2025.
Notice of Allowance for U.S. Appl. No. 17/635,866 mailed Mar. 2, 2026.
Notice of Allowance for U.S. Appl. No. 17/645,821 mailed Nov. 24, 2025.
Notice of Allowance for U.S. Appl. No. 17/646,771 mailed Dec. 17, 2024.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/661,090 mailed Oct. 30, 2024.
Notice of Allowance for U.S. Appl. No. 17/663,330 mailed Nov. 20, 2024.
Notice of Allowance for U.S. Appl. No. 17/664,487 mailed Jun. 1, 2026.
Notice of Allowance for U.S. Appl. No. 17/749,340 mailed Feb. 14, 2025.
Notice of Allowance for U.S. Appl. No. 17/754,736 mailed Jan. 28, 2026.
Notice of Allowance for U.S. Appl. No. 17/755,236 mailed Jul. 17, 2025.

(56) References Cited

OTHER PUBLICATIONS

Notice of Allowance for U.S. Appl. No. 17/757,311 mailed May 5, 2025.
Notice of Allowance for U.S. Appl. No. 17/758,316 mailed Mar. 24, 2025.
Notice of Allowance for U.S. Appl. No. 17/759,697 mailed Jan. 30, 2026.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/041,109 mailed Mar. 25, 2026.
Notice of Allowance for U.S. Appl. No. 18/044,413 mailed Sep. 16, 2025.
Notice of Allowance for U.S. Appl. No. 18/134,857 mailed Feb. 20, 2025.
Notice of Allowance for U.S. Appl. No. 18/139,523 mailed Jun. 5, 2026.
Notice of Allowance for U.S. Appl. No. 18/140,751 mailed Nov. 1, 2024.
Notice of Allowance for U.S. Appl. No. 18/164,800 mailed Jun. 11, 2026.
Notice of Allowance for U.S. Appl. No. 18/246,121 mailed May 12, 2026.
Notice of Allowance for U.S. Appl. No. 18/249,577 mailed Mar. 31, 2026.
Notice of Allowance for U.S. Appl. No. 18/260,122 mailed Jul. 30, 2025.
Notice of Allowance for U.S. Appl. No. 18/264,004 mailed Jan. 30, 2026.
Notice of Allowance for U.S. Appl. No. 18/264,278 mailed Apr. 24, 2026.
Notice of Allowance for U.S. Appl. No. 18/294,370 mailed Mar. 17, 2026.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/553,625 mailed Apr. 15, 2026.
Notice of Allowance for U.S. Appl. No. 18/558,502 mailed May 6, 2026.
Notice of Allowance for U.S. Appl. No. 18/584,002 mailed Jan. 8, 2025.
Notice of Allowance for U.S. Appl. No. 18/610,523 mailed Mar. 4, 2026.
Notice of Allowance for U.S. Appl. No. 18/688,023 mailed Jun. 11, 2026.
Restriction Requirement for U.S. Appl. No. 17/625,887 mailed Sep. 2, 2025.
Restriction Requirement for U.S. Appl. No. 17/754,736 mailed Nov. 20, 2024.
Restriction Requirement for U.S. Appl. No. 17/755,236 mailed Apr. 24, 2025.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/294,403 mailed Jan. 27, 2026.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/558,502 mailed Jan. 29, 2026.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 18/687,117 mailed Mar. 26, 2026.
Restriction Requirement for U.S. Appl. No. 18/693,638 mailed Jun. 11, 2026.
Restriction Requirement for U.S. Appl. No. 19/237,368 mailed Dec. 18, 2025.
Supplemental Notice of Allowance for U.S. Appl. No. 17/597,673 mailed Apr. 10, 2025.
U.S. Appl. No. 17/051,399, filed Oct. 28, 2020.
U.S. Appl. No. 17/596,629, filed Dec. 15, 2021.
U.S. Appl. No. 17/625,941, filed Jan. 10, 2022.
U.S. Appl. No. 17/635,866, filed Feb. 16, 2022.
U.S. Appl. No. 18/034,902, filed May 2, 2023.

(56) References Cited

OTHER PUBLICATIONS

U.S. Appl. No. 18/546,465, filed Aug. 15, 2023.
U.S. Appl. No. 18/851,197, filed Sep. 26, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/353,151, filed Oct. 8, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/490,075, filed Dec. 4, 2025.
U.S. Appl. No. 19/491,481, filed Dec. 9, 2025.
U.S. Appl. No. 19/494,631, filed Dec. 18, 2025.
U.S. Appl. No. 19/510,850, filed Feb. 12, 2026.
U.S. Appl. No. 19/513,755, filed Feb. 24, 2026.
U.S. Appl. No. 19/513,838, filed Feb. 24, 2026.
U.S. Appl. No. 19/514,100, filed Feb. 25, 2026.
U.S. Appl. No. 19/534,156, filed Feb. 9, 2026.
U.S. Appl. No. 19/535,649, filed Feb. 10, 2026.
U.S. Appl. No. 19/539,961, filed Feb. 13, 2026.
U.S. Appl. No. 19/541,655, filed Feb. 17, 2026.
U.S. Appl. No. 19/544,501, filed Feb. 19, 2026.
U.S. Appl. No. 19/554,125, filed Mar. 2, 2026.
U.S. Appl. No. 19/579,050, filed Apr. 16, 2026.
U.S. Appl. No. 19/582,525, filed Apr. 28, 2026.
U.S. Appl. No. 19/584,751, filed May 5, 2026.
U.S. Appl. No. 19/584,819, filed May 5, 2026.
U.S. Appl. No. 19/588,736 mailed May 19, 2026.
U.S. Appl. No. 19/595,261, filed Jun. 10, 2026.
U.S. Appl. No. 19/638,741, filed Apr. 3, 2026.
U.S. Appl. No. 19/657,823, filed Apr. 24, 2026.
U.S. Appl. No. 19/695,314, filed Jun. 2, 2026.
U.S. Appl. No. 62/665,711, filed May 2, 2018.
U.S. Appl. No. 63/564,696, filed Mar. 13, 2024.
U.S. Appl. No. 63/181,709, filed Apr. 29, 2021.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
Advisory Action for U.S. Appl. No. 17/444,792 mailed Jul. 8, 2024.
Advisory Action for U.S. Appl. No. 17/451,345 mailed Jul. 3, 2024.
Advisory Action for U.S. Appl. No. 17/645,821 mailed Jul. 2, 2024.
Corrected Notice of Allowability for U.S. Appl. No. 17/501,591 mailed Aug. 9, 2024.
Corrected Notice of Allowability for U.S. Appl. No. 17/664,914 mailed Aug. 9, 2024.
Final Office Action for U.S. Appl. No. 16/433,773 mailed Sep. 9, 2024.
Final Office Action for U.S. Appl. No. 17/051,585 mailed Jul. 5, 2024.
Final Office Action for U.S. Appl. No. 17/446,256 mailed Aug. 7, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 18/134,857 mailed Jul. 25, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/453,560 mailed Aug. 7, 2024.
Non-Final Office Action for U.S. Appl. No. 16/478,180 mailed Aug. 7, 2024.
Non-Final Office Action for U.S. Appl. No. 17/378,015 mailed Jul. 5, 2024.
Non-Final Office Action for U.S. Appl. No. 17/451,345 mailed Jul. 25, 2024.
Non-Final Office Action for U.S. Appl. No. 17/597,408 mailed Aug. 15, 2024.
Non-Final Office Action for U.S. Appl. No. 17/645,821 mailed Sep. 6, 2024.
Non-Final Office Action for U.S. Appl. No. 17/653,314 mailed Aug. 29, 2024.
Non-Final Office Action for U.S. Appl. No. 17/663,330 mailed Jul. 1, 2024.
Non-Final Office Action for U.S. Appl. No. 17/749,340 mailed Aug. 14, 2024.
Non-Final Office Action for U.S. Appl. No. 17/758,316 mailed Aug. 28, 2024.
Non-Final Office Action for U.S. Appl. No. 18/139,523 mailed Aug. 26, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/452,145 mailed Jul. 11, 2024.
Notice of Allowance for U.S. Appl. No. 17/179,116 mailed Sep. 13, 2024.
Notice of Allowance for U.S. Appl. No. 17/447,123 mailed Jul. 26, 2024.

(56) References Cited

OTHER PUBLICATIONS

Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/198,464 mailed Jul. 30, 2024.
Notice of Allowance for U.S. Appl. No. 18/389,009 mailed Aug. 28, 2024.
Restriction Requirement for U.S. Appl. No. 17/596,629 mailed Sep. 19, 2024.
Restriction Requirement for U.S. Appl. No. 17/625,941 mailed Aug. 7, 2024.
U.S. Appl. No. 15/611,587, filed Jun. 1, 2017.
U.S. Appl. No. 17/013,822, filed Sep. 7, 2020.
U.S. Appl. No. 18/728,604, filed Jul. 12, 2024.
U.S. Appl. No. 18/757,964, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/886,306, filed Sep. 16, 2024.
U.S. Appl. No. 63/568,615, filed Mar. 22, 2024.
U.S. Appl. No. 63/683,428, filed Aug. 15, 2024.

* cited by examiner

FLUID COLLECTION ASSEMBLIES INCLUDING AT LEAST ONE INFLATION DEVICE AND METHODS AND SYSTEMS OF USING THE SAME

BACKGROUND

A person or animal may have limited or impaired mobility so typical urination processes are challenging or impossible. For example, a person may experience or have a disability that impairs mobility. A person may have restricted travel conditions such as those experienced by pilots, drivers, and workers in hazardous areas. Additionally, sometimes bodily fluids collection is needed for monitoring purposes or clinical testing.

Urinary catheters, such as a Foley catheter, can address some of these circumstances, such as incontinence. Unfortunately, urinary catheters can be uncomfortable, painful, and can lead to complications, such as infections. Additionally, bed pans, which are receptacles used for the toileting of bedridden patients are sometimes used. However, bedpans can be prone to discomfort, spills, and other hygiene issues.

SUMMARY

Embodiments disclosed herein are directed to fluid collection assemblies that include at least one inflation device, methods for using the same, and systems including the same. In an embodiment, a fluid collection assembly is disclosed. The fluid collection assembly includes a fluid impermeable barrier defining a chamber, at least one opening, and at least one fluid outlet. The fluid collection assembly also includes at least one porous material disposed in the chamber. The fluid collection assembly further includes at least one inflation device including at least one bladder and at least one valve. The at least one bladder includes one or more walls defining an interior region. The at least one valve is configured to selectively permit at least one inflation fluid to flow into and out of the interior region to switch the at least one bladder between a first state and a second state. An amount of the at least one inflation fluid present in the interior region is greater when the at least one bladder is in the second state than when the at least one bladder is in the first state.

In an embodiment, a system is disclosed. The system includes a fluid collection assembly, a fluid storage container, a vacuum source, and one or more conduits. The one or more conduits operably couple at least one fluid outlet of the fluid collection assembly, the fluid storage container, and the vacuum source together. The fluid collection assembly of the system includes any one of the fluid collection assemblies disclosed herein.

In an embodiment, a method of using a fluid collection assembly is disclosed. The method includes positioning at least one opening of the fluid collection assembly adjacent to a female urethra or to receive a male penis therethrough. The fluid collection assembly includes a fluid impermeable barrier defining the at least one opening, a chamber, and the at least one fluid outlet. The fluid collection assembly also includes at least one porous material disposed in the chamber. The fluid collection assembly further includes at least one inflation device including at least one bladder and at least one valve, the at least one bladder including one or more walls defining an interior region. The method includes flowing at least one inflation fluid through the at least one valve and into the interior region of the at least one inflation element.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
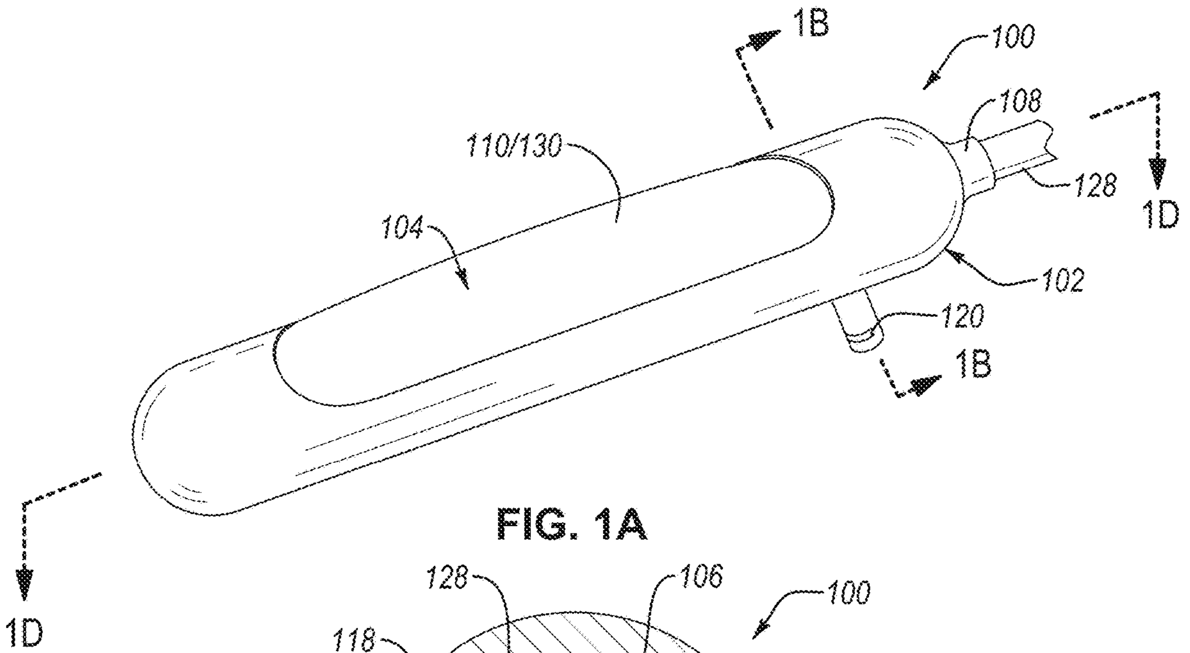
FIG. 1A is an isometric view of a fluid collection assembly configured to be used to collect bodily fluids from a female urethral opening, according to an embodiment.

Embodiments disclosed herein are directed to fluid collection assemblies that include at least one inflation device, methods for using the same, and systems including the same. An example fluid collection assembly includes a fluid impermeable barrier defining at least one opening, a chamber, and at least one fluid outlet. The fluid collection assembly also includes at least one porous material disposed in the chamber. As previously discussed, the fluid collection assembly further includes at least one inflation device. The inflation device includes at least one bladder having one or more walls defining an interior region. The inflation device also includes at least one valve configured to selectively permit fluid flow into and out of the interior region to switch the at least one bladder between a first state (e.g., a deflated and/or initial state) and a second state (e.g., an at least partially inflated state). The inflation device may facilitate securement of the fluid collection assembly with certain patients (e.g., underweight patients or patients with thin thighs) when the bladder of the inflation device is in the second state.

The fluid collection assembly is configured to be positioned about or around the pubic region of a patient. When the patient is a female, the pubic region may include the vulva (e.g., labia majora, labia minora, clitoris, urethral opening, etc.), mons pubis, the perineum, buttocks, and the inner thighs of the patient. When the patient is a male, the pubic region may include the penis, the testicles, the mons pubis, the buttocks, and the inner thighs of the patient.

The fluid collection assembly may be flexible thereby allowing the fluid collection assembly to conform to the size and topography of the pubic region since the size and topography of the pubic region may vary significantly from person to person. Conforming the fluid collection assembly to the pubic region may prevent or inhibit embarrassing and unsanitary leaks of bodily fluids (e.g., urine, blood, sweat, etc.). In some embodiments, the fluid collection assembly may rely on contact pressure from the thighs of the individual to remain conformed to the pubic region. However, it has been found that the thighs of some individuals may not provide sufficient contact pressure to allow the fluid collection assembly to remain conformed to the pubic when the fluid collection assembly is in the first (e.g., deflated) state. For instance, it has been found that underweight patients and other patients having thin thighs may not provide sufficient contact pressure to the fluid collection assembly to allow the fluid collection assembly to remain conformed to the pubic region when the fluid collection assembly is in the first state. Some conventional fluid collection assemblies that do not include the inflation device may have similar problems remaining conformed to the pubic region.

The inflatable devices disclosed herein allow the fluid collection assemblies disclosed herein to remain conformed to the pubic region even when the patient is underweight or has thin thighs. For example, when the fluid collection assembly does not have sufficient contact pressure from the thighs to remain conformed to the pubic region, at least one inflation fluid (e.g., gas or liquid) may be added to the interior region of the bladder through the valve. Adding the fluid to the interior region switches the bladder from the first state to the second state. Changing the bladder from the first state to the second shape also changes the shape and/or size of the fluid collection assembly. The changes in the shape and/or size of the fluid collection assembly may allow the fluid collection assembly to press against the thighs so the thighs provide sufficient contact pressure to allow the fluid collection assembly to remain conformed to the female anatomy.

The fluid collection assembly is configured to be disposed against the patient so the opening of the fluid impermeable barrier is disposed adjacent to at least the urethral opening of the patient. After positioning the fluid collection assembly, the patient may discharge bodily fluids, either controllably or uncontrollably. The porous material may remove the bodily fluids from the patient and move the bodily fluids through the opening and the chamber to the fluid outlet. The bodily fluids may be removed from the chamber via the fluid outlet by using at least one gravity (e.g., the fluid outlet is at the gravimetric low point of the chamber) or a suction force provided by a vacuum which suctions the bodily fluids from the chamber.

Figure 1B:
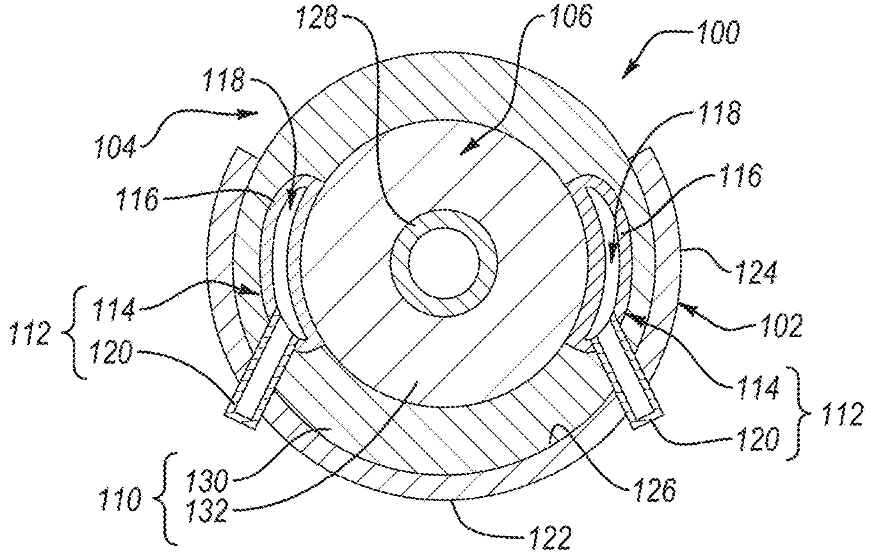
FIGS. 1B and 1C are schematic cross-sectional views of the fluid collection assembly taken along plane 1B-1B when a bladder of the fluid collection assembly is in a first state and in a second state, respectively, according to an embodiment.
Figure 1C:
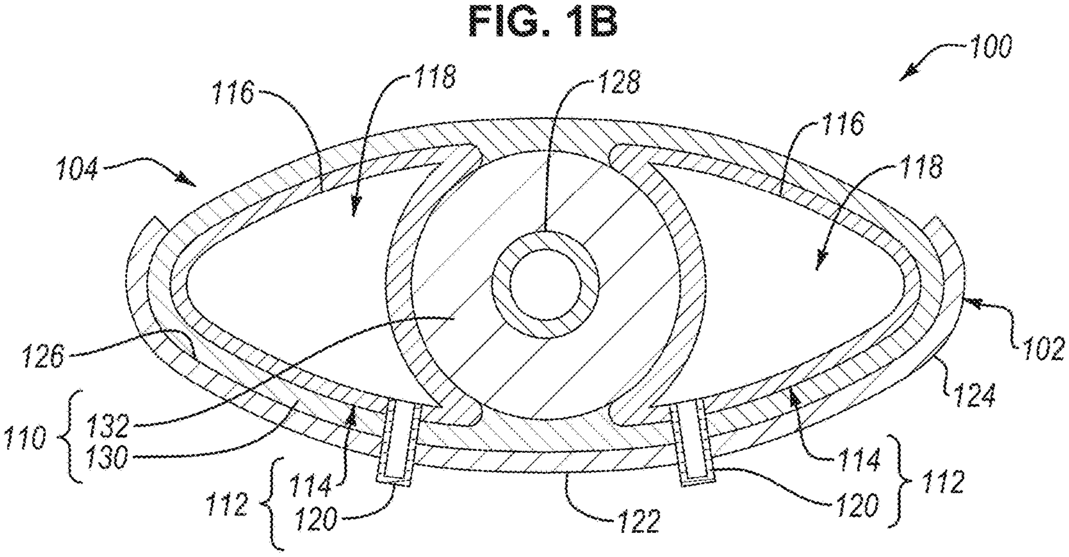
Figure 1D:
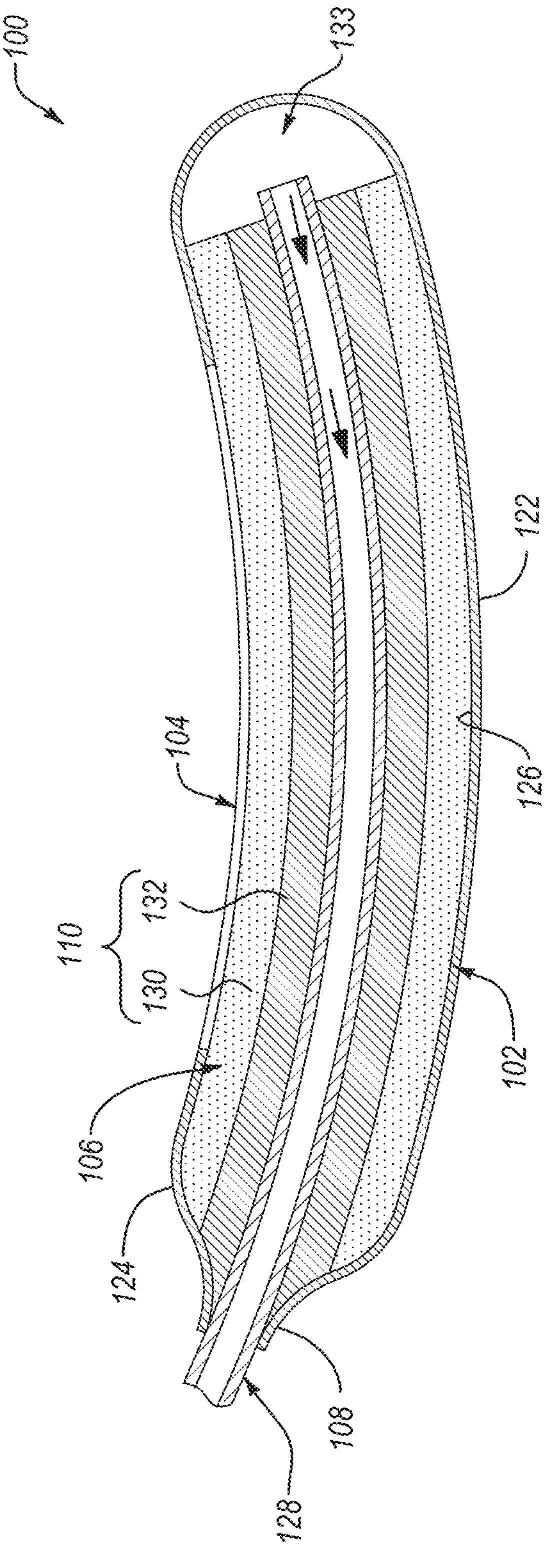
FIG. 1D is a schematic cross-sectional view of the fluid collection assembly taken along plane 1D-1D, according to an embodiment.

FIG. 1A is an isometric view of a fluid collection assembly 100 configured to be used to collect bodily fluids from a female urethral opening, according to an embodiment. FIGS. 1B and 1C are schematic cross-sectional views of the fluid collection assembly 100 taken along plane 1B-1B when a bladder 114 of the fluid collection assembly 100 is in a first state and in a second state, respectively, according to an embodiment. FIG. 1D is a schematic cross-sectional view of the fluid collection assembly 100 taken along plane 1D-1D, according to an embodiment. The fluid collection assembly 100 includes a fluid impermeable barrier 102 defining at least one opening 104, a chamber 106, and at least one fluid outlet 108. The fluid collection assembly 100 also includes at least one porous material 110 disposed chamber 106. The fluid collection assembly 100 further includes at least one inflation device 112 configured to change the shape and/or size of the fluid collection assembly 100.

The inflation device 112 includes a bladder 114. The bladder 114 includes one or more walls 116 defining an interior region 118. The inflation device 112 also includes at least one valve 120 in fluid communication with the interior region 118. The valve 120 is configured to selectively permit flow of an inflation fluid into and/or out the interior region 118. For example, the valve 120 may allow an inflation fluid to enter the interior region 118 when it is desirable to at least one of increase the size or change the shape of the bladder 114 which, in turn, at least one of increases the size or changes the shape of the fluid collection assembly 100. The valve 120 may also enable removing the inflation fluid from the interior region 118 when it is desirable to at least one of decrease the size or change the shape (e.g., return to the initial shape) of the bladder 114 which, in turn, at least one of decreases the size or changes the shape of the fluid collection assembly 100.

Disposing or removing the inflation fluids into and from the inflation region 118 changes the state of the bladder 114. The bladder 114 may exhibit at least a first state and a second state. The amount (volume or weight) of inflation fluids present in the inflation region 118 is greater when the bladder 114 is in the second state than when the bladder 114 is in the first state. In an example, as shown in FIG. 1B, the bladder 114 is in the first state when the bladder 114 is in a deflated state (e.g., there are no or substantially no fluids in the inflation region 118). However, it is noted that the bladder 114 may be in the first state when some inflation fluids are present in the inflation region 118. The bladder 114 generally also correspond to an initial state of the bladder 114 (i.e., generally, the bladder 114 is not provided with inflation fluids) though, in some examples, the first state of the bladder 114 may not correspond to the initial state of the bladder 114 (e.g., the bladder 114 is provided with fluids). In an example, as shown in FIG. 1C, the bladder 114 is in the first state when the bladder 114 is in an at least partially inflated state. The bladder 114 is generally not in the initial state when the bladder 114 is in the second state though, in some examples, the initial state and the second state of the bladder 114 are the same (e.g., when the bladder 114 is provided with fluids).

The bladder 114 may exhibit one or more additional states (e.g., third state, fourth state, and so forth) besides the first and second states discussed above. In an embodiment, the one or more additional states may include less inflation fluids in the inflation region 118 (e.g., is more deflated) than the first state (e.g., the first state is a partially inflated state). In such an embodiment, the one or more additional states may include a deflated or partially deflated state and may be formed by removing inflation fluids from the inflation region 118 when the bladder 114 is in the first or second state. In an embodiment, the one or more additional states may include more inflation fluids in the inflation region 118 (e.g., is more inflated) than the first state (e.g., the first state is a deflated or partially inflated state) and include less inflation fluids in the inflation region 118 than the second state. In such an embodiment, the one or more additional states include a partially inflated state and may be formed by adding or removing inflation fluids to the inflation region 118 when the bladder 114 is in the first state or second state, respectively. In an embodiment, the one or more additional states may include more inflation fluids in the inflation region 118 than the second state (e.g., the second state is a partially inflated state). In such an embodiment, the one or more additional states may be an at least partially inflated state and may be formed by adding inflation fluids to the inflation region 118 when the bladder 114 is in the first state or second state. It is noted that, in some embodiments, the bladder 114 may only include the first and second states.

As shown in FIGS. 1B and 1C, switching the bladder 114 from the first state to the second state (or any of the other states thereof) changes the shape and/or size of the fluid collection assembly 100 and the bladder 114. For example, referring to FIG. 1B, the fluid collection assembly 100 may exhibit a generally circular cross-sectional shape (e.g., the fluid collection assembly 100 exhibits a generally cylindrical shape, as shown in FIG. 1A) when the bladder 114 is in the first state. The bladder 114 may also exhibit a thin generally crescent cross-sectional shape when the bladder 114 is in the first state. It is noted that the fluid collection assembly 100 and/or the bladder 114 may exhibit different shapes when the bladder 114 is in the first state than the shapes illustrated in FIG. 1B. Switching the bladder 114 to the second state changes the shape of the fluid collection assembly 100, as shown in FIG. 1C, to a generally oblong cross-sectional shape and the bladder 114 into a wide generally crescent shape (i.e., a generally triangular shape). Further, switching the bladder 114 from the first state to the second state increases the size of the fluid collection assembly 100 and the bladder 114. For example, the increased size of the fluid collection assembly 100 may allow the fluid collection assembly 100 to contact and press against the inner thighs of a patient, even an underweight patient or a patient with thin thighs, allowing the fluid collection assembly 100 to remain conformed to the pubic region of the patient. It is noted that inflation fluids may be removed from the inflation region 118 using the valve 120, for example, when too much inflation fluids are added to the inflation region 118 which may at least one of increase the risk that the bladder 114 ruptures, make the fluid collection assembly 100 more uncomfortable, or increase the likelihood that the fluid collection assembly 100 leaks bodily fluids.

The walls 116 are formed from a material is substantially impermeable to the inflation fluid (e.g., substantially impermeable to a gas and/or a liquid) which allows the bladder 114 to retain the inflation fluids without embarrassing leaks. The walls 116 may also be formed from a flexible material. The flexible material of the walls 116 allows the bladder 114 and, by extension, the fluid collection assembly 100 to at least one of increase in size or change a shape thereof. For example, the flexible material of the walls 116 allow the interior region 118 to increase a volume thereof when the interior region 118 receives an inflation fluid and decrease a volume thereof when inflation fluids are removed from the interior region 118. Examples of materials that may form the walls 116 of the bladder 114 include silicone, rubber, latex, polychloroprene, nylon fabric, polypropylene, polyvinyl chloride, nitrile rubber, other suitable polymers, a metal foil, a composite, or combinations thereof. It is noted that the walls 116 do not contact the patient in the illustrated embodiment and might be formed from a biocompatible material. In an embodiment, the walls 116 are configured to stretch (e.g., elastically or plastically stretch) so the walls 116 remain taut when the bladder 114 is at least partially inflated. In an embodiment, the wall 116 forms a plurality of wrinkles when the bladder 114 is at least partially deflated and adding inflation fluid into the inflation region 118 decreases the wrinkles, similar to an accordion.

The valve 120 may include any suitable valve configured to allow for the controllable addition and remove of inflation fluids from the inflation region 118. In an embodiment, the valve 120 is a luer valve and includes a male-tapper fitting or a female-taper fitting. In an embodiment, the valve 120 includes a fluid impermeable membrane with a slit or opening formed. The slit or opening of the fluid impermeable membrane remains substantially closed when no external load is applied thereto but opens when an external load is applied thereto (e.g., an external load caused by pressing a syringe against the fluid impermeable membrane). In an embodiment, the valve 120 may include a mechanical valve, such as a ball valve, a butterfly valve, or any other suitable mechanical valve. The mechanical valve may be manually operated or controlled using a computer. In an embodiment, the valve 120 may include a check valve to limit leaks from the bladder 114 and to make the fluid collection assembly 100 easier to use. In such an embodiment, the valve 120 may only add or remove (but not both) inflation fluid from the inflation region 118 and, as such, the fluid collection assembly 100 is configured for single use.

In an embodiment, as illustrated, the valve 120 may extend outwardly from the bladder 114. For example, the valve 120 may extend from the bladder 114, through a portion of the porous material 110, and through the fluid impermeable barrier 102 thereby allowing a user (e.g., medical practitioner or patient) of the fluid collection assembly 100 easily access to the valve 120. As shown, the valve 120 may extend a short distance only from the fluid impermeable barrier 102, such as about 2 cm or less, about 1.5 cm or less, about 1 cm or less, about 0.75 cm or less, about 0.5 cm or less, about 0.25 cm or less, or in ranges of about 0.25 cm to about 0.75 cm, about 0.5 cm to about 1 cm, about 0.75 cm to about 1.5 cm, or about 1 cm to about 2 cm. However, the valve 120 may extend a significant distance from the fluid impermeable barrier 102, such as a distance that is about 2 cm or greater, about 5 cm or greater, about 10 cm or greater, about 50 cm or greater, about 100 cm or greater, about 500 cm or greater, about 1 m or greater, about 2 m or greater, or in ranges of about 2 cm to about 10 cm, about 5 cm to about 50 cm, about 10 cm to about 100 cm, about 50 cm to about 500 cm, about 100 cm to about 1 m, or about 500 cm to about 2 m. When the valve 120 extends a significant distance from the fluid impermeable barrier 102, the valve 120 may include a flexible tube which allows a user of the fluid collection assembly 100 to easily access to the valve 120 while the fluid collection assembly 100 is positioned adjacent to the pubic region without having the user near the pubic region (which the patient may find uncomfortable).

In an embodiment, as illustrated, the valve 120 extends from or near a back surface 122 of the fluid impermeable barrier 102. The back surface 122 of the fluid impermeable barrier 102 is the surface of the fluid impermeable barrier 102 opposite the opening 104. The valve 120 at or near the back surface 122 may allow a user of the fluid collection assembly 100 to access the valve 120 when the fluid collection assembly 100 is adjacent to the pubic region since, generally, the pubic region and the inner thighs of the patient may contact or obstruct the surfaces of the fluid impermeable barrier 102 except the back surface 122. Further, the valve 120 at or near the back surface 122 prevents the valve 120 from pressing against the pubic region and the inner thighs during use which may cause discomfort.

In an embodiment, the fluid collection assembly 100 may only include a single bladder 114 and/or a single valve 120. In an embodiment, the fluid collection assembly 100 may include a plurality of bladders 114 and/or a plurality of valves 120. For example, as illustrated, the fluid collection assembly 100 may include two bladders 114 on each lateral side of the fluid collection assembly 100 which allows the fluid collection assembly 100 to increase is size laterally which allows the fluid collection assembly 100 to contact the thighs of the patient. Each bladder 114 may include one or more valves 120 to allow for independent inflation of the bladders 114 which allows for better control of the shape and size of the fluid collection assembly 100. However, the fluid collection assembly 100 may only include a single valve 120 for two or more bladders 114. In some examples, a single bladder 114 may include a plurality of valves 120, for instance, to increase the likelihood that one valve 120 is easily accessible.

The inflation device 112 may include additional components other than the components discussed above. For example, the inflation device 112 may include less flexible material (e.g., rigid material or material that is less flexible than the walls 116) that are used to control the shape of the bladder 114 when the bladder 114 is inflated (e.g., switched from the first state to the second state). The less flexible material may form parts of the walls 116, wrap around the walls 116, or extend in the inflation region 118 between opposing portions of the walls 116 which limits expansion of the walls 116 at and near the less flexible material.

The at least one inflation fluid added or removed from the interior region 118 may include any suitable fluid, such as any suitable liquid or any suitable gas. In an embodiment, the inflation fluids are formed from a generally regarded as safe ("GRAS") material. Forming the inflation fluids from a GRAS materials may decrease health risks caused by inadvertently exposing the patient to the inflation fluids. Examples of GRAS materials that may form the inflation fluids includes water, saline solution, alcohol solution, atmospheric air, nitrogen, any other GRAS material, or combinations thereof.

As previously discussed, the fluid collection assembly 100 includes a fluid impermeable barrier 102. In the illustrated embodiment, the fluid impermeable barrier 102 is distinct from the inflation device 112 and is spaced from the inflation device 112 by at least a portion of the porous material 110.

The fluid impermeable barrier 102 may be formed of any suitable fluid imperious material(s), such as a fluid impermeable polymer (e.g., silicone, polypropylene, polyethylene, polyethylene terephthalate, a polycarbonate, etc.), a metal film, natural rubber, another suitable material, or combinations thereof. The fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least a surface of the fluid impermeable barrier 102 that may contact the patient may be formed from a soft and/or smooth material (e.g., silicone), thereby reducing chaffing. In an embodiment, the fluid impermeable barrier 102 may be formed from a flexible material, such as silicone, which allows the fluid impermeable barrier 102 to be bent into a shape that conforms the anatomy of the individual. Further, as shown in FIGS. 1B and 1C, forming the fluid impermeable barrier 102 from a flexible material allows the fluid impermeable barrier 102 to accommodate the shape and/or size changes by switching the fluid collection assembly 100 and the bladder 114 between states.

The fluid impermeable barrier 102 may define a hole that allows the valve 120 to extend through the fluid impermeable barrier 102. For example, the fluid impermeable barrier 102 may define the hole at or near the back surface 122 thereof. The hole formed in the fluid impermeable barrier 102 is configured to form a substantially fluid tight seal against the valve 120 or a sealant is applied between the fluid impermeable barrier 102 and the valve 120 to prevent bodily fluids from leaking through the hole.

In some examples, the fluid impermeable barrier 102 may be tubular (ignoring the opening), such as substantially cylindrical (as shown), oblong, prismatic, or flattened tubes when the bladder 114 is in the first state and/or the second state. During use, the outer surface 124 of the fluid impermeable barrier 102 may contact the patient. The fluid impermeable barrier 102 may be sized and shaped to fit in the gluteal cleft between the legs of a female user when the bladder 114 are in at least the second state.

The opening 104 provides an ingress route for fluids to enter the chamber 106. The opening 104 may be defined by the fluid impermeable barrier 102 such as by an inner edge of the fluid impermeable barrier 102. For example, the opening 104 is formed in and extends through the fluid impermeable barrier 102, from the outer surface 124 to the inner surface 126, thereby enabling fluid(s) to enter the chamber 106 from outside of the fluid collection assembly 100. The opening 104 may be an elongated hole in the fluid impermeable barrier 102. For example, the opening 104 may be defined as a cut-out in the fluid impermeable barrier 102. The opening 104 may be located and shaped to be positioned adjacent to a female urethra.

The fluid collection assembly 100 may be positioned proximate to the female urethral opening and urine may enter the chamber of the fluid collection assembly 100 via the opening 104. The fluid collection assembly 100 is configured to receive the fluid(s) into the chamber 106 via the opening 104. When in use, the opening 104 may have an elongated shape that extends from a first location below the urethral opening (e.g., at or near the anus or the vaginal opening) to a second location above the urethral opening (e.g., at or near the top of the vaginal opening or the pubic hair).

The opening 104 may have an elongated shape because the space between the legs of a female is relatively small when the legs of the female are closed, thereby only permitting the flow of the fluid(s) along a path that corresponds to the elongated shape of the opening 104 (e.g., longitudinally extending opening). The opening 104 in the fluid impermeable barrier 102 may exhibit a length measured along the longitudinal axis of the fluid collection assembly 100 that may be at least about 10% of the length of the fluid collection assembly 100, such as about 25% to about 50%, about 40% to about 60%, about 50% to about 75%, about 65% to about 85%, or about 75% to about 95% of the length of the fluid collection assembly 100.

The opening 104 in the fluid impermeable barrier 102 may exhibit a width measured transverse to the longitudinal axis of the fluid collection assembly 100 that may be, when the fluid collection assembly 100 and the bladder 114 are in the first state, at least about 10% of the circumference of the fluid collection assembly 100, such as about 25% to about 50%, about 40% to about 60%, about 50% to about 75%, about 65% to about 85%, or about 75% to about 100% of the circumference of the fluid collection assembly 100. The opening 104 may exhibit a width that is greater than 50% of the circumference of the fluid collection assembly 100 since the vacuum (e.g., suction) through the conduit 128 pulls the fluid through the porous material 110 and into the conduit 128. As shown in FIGS. 1B and 1C, switching the bladder 114 from the first state to the second state increases the width of the opening 104. The increased width of the opening 104 may allow the opening 104 to receive more bodily fluids than if the opening 104 did not exhibit the increased width.

In some examples, the opening 104 may be vertically oriented (e.g., having a major axis parallel to the longitudinal axis of the fluid collection assembly 100). In some examples (not shown), the opening 104 may be horizontally oriented (e.g., having a major axis perpendicular to the longitudinal axis of the fluid collection assembly 100). In an example, the fluid impermeable barrier 102 may be configured to be attached to the individual, such as adhesively attached (e.g., with a hydrogel adhesive) to the individual. According to an example, a suitable adhesive is a hydrogel layer.

As previously discussed, the fluid impermeable barrier 102 may define fluid outlet 108 configured to remove bodily fluids from the chamber 106. The fluid outlet 108 is distinct from the opening 104 and the valve 120. In some examples, the fluid outlet 108 is sized to receive the conduit 128. The conduit 128 may be disposed in the chamber 106 via the fluid outlet 108. The fluid outlet 108 may be sized and shaped to form an at least substantially fluid tight seal against the conduit 128 or the at least one tube substantially preventing the bodily fluids from escaping the chamber 106.

The fluid impermeable barrier 102 may include markings thereon, such as one or more markings to aid a user in aligning the fluid collection assembly 100 on the patient. For example, a line on the fluid impermeable barrier 102 (e.g., opposite the opening 104) may allow a healthcare professional to align the opening 104 over the urethral opening of the patient. In examples, the markings may include one or more of alignment guide or an orientation indicator, such as a stripe or hashes. Such markings may be positioned to align the fluid collection assembly 100 to one or more anatomical features such as a pubic bone, etc.

As previously discussed, the fluid collection assembly 100 includes porous material 110 disposed in the chamber 106. The porous material 110 may cover at least a portion (e.g., all) of the opening 104. The porous material 110 is exposed to the environment outside of the chamber 106 through the opening 104. The permeable properties referred to herein may be wicking, capillary action, absorption, diffusion, or other similar properties or processes, and are referred to herein as "permeable" and/or "porous." The porous material 110 may also wick the bodily fluids generally towards an interior of the chamber 106, as discussed in more detail below. The porous material 110 may include one or more of a fluid permeable membrane 130 or a fluid permeable support 132.

In an embodiment, at least a portion of the porous material 110 may be a wicking material configured to wick and/or allow transport of the bodily fluids away from the opening 104, thereby preventing bodily fluids from escaping the chamber 106. The porous material 110 may not include absorption of the bodily fluids into the w porous material 110. Put another way, substantially no absorption of the bodily fluids into the porous material 110 may take place after the wicking material is exposed to the bodily fluids. While no absorption is desired, the term "substantially no absorption" may allow for nominal amounts of absorption of the bodily fluids into the wicking material (e.g., absorbency), such as about 30 wt % or less of the dry weight of the wicking material, about 20 wt % or less, 10 wt % or less, about 7 wt % or less, about 5 wt % or less, about 3 wt % or less, about 2 wt % or less, about 1 wt % or less, or about 0.5 wt % or less of the dry weight of the wicking material.

The fluid collection assembly 100 may include the fluid permeable membrane 130 disposed in the chamber 106. The fluid permeable membrane 130 may cover at least a portion (e.g., all) of the opening 104. The fluid permeable membrane 130 may be composed to pull/push the bodily fluids away from the opening 104, thereby promoting fluid flow into the chamber 106, prevent fluid remaining on the vulva of the patient, and preventing the bodily fluids from escaping the chamber 106.

The fluid permeable membrane 130 may include any material that may be permeable to the bodily fluids. For example, the fluid permeable membrane 130 may include fabric, such as a gauze (e.g., a silk, linen, or cotton gauze), another soft fabric, or another smooth fabric. Forming the fluid permeable membrane 130 from gauze, soft fabric, and/or smooth fabric may reduce chaffing caused by the fluid collection assembly 100 and makes wearing the fluid collection assembly more comfortable. In an embodiment, the fluid permeable membrane 130 is formed from a flexible material, such as gauze, since the shape and/or size of the fluid permeable membrane 130 may change when the fluid collection assembly 100 and the bladder 114 switch between states, as shown in FIGS. 1B and 1C. In an embodiment, the fluid permeable membrane 130 may define a plurality of perforations or may be continuous (e.g., does not define perforations). In an embodiment, the fluid permeable membrane 130 defines at least one hole that is configured to allow the valve 120 to extend through the fluid permeable membrane 130.

The fluid collection assembly 100 may include the fluid permeable support 132 disposed in the chamber 106. The fluid permeable support 132 is configured to support the fluid permeable membrane 130 and maintain the shape of the chamber 106 since the fluid impermeable barrier 102 and the fluid permeable membrane 130 may be formed from a relatively foldable, flimsy, or otherwise easily deformable material. For example, the fluid permeable support 132 may be positioned so the fluid permeable membrane 130 is disposed between the fluid permeable support 132 and the fluid impermeable barrier 102. The fluid permeable support 132 may support and maintain the position of the fluid permeable membrane 130 and the shape of the chamber 106. The fluid permeable support 132 may include any material that may be permeable to the bodily fluids, such as any of the fluid permeable membrane 130 materials disclosed above. For example, the fluid permeable membrane 130 material(s) may be utilized in a more dense or rigid form than in the fluid permeable membrane 130 when used as the fluid permeable support 132. The fluid permeable support 132 may be formed from any fluid porous material that is less deformable than the fluid permeable membrane 130. For example, the fluid permeable support 132 may include a porous polymer (e.g., nylon, polyester, polyurethane, polyethylene, polypropylene, etc.) structure (e.g., spun fibers such as spun nylon fibers), nonwoven material, or a foam (e.g., an open cell foam). In some examples, the fluid permeable support 132 may be formed from a natural material, such as cotton, wool, silk, or combinations thereof. In such examples, the material may have a coating to prevent or limit absorption of the bodily fluids into the material, such as a water repellent coating. In some examples, the fluid permeable support 132 may be formed from fabric, felt, gauze, or combinations thereof.

In an embodiment, as illustrated, the bladder 114 is positioned between the fluid permeable membrane 130 and the fluid permeable support 132 (e.g., the bladder 114 is positioned in the chamber 106). The bladder 114 may be positioned between the fluid permeable membrane 130 and the fluid permeable support 132 since that at least some materials that form the fluid impermeable barrier 102 and the fluid permeable membrane 130 exhibit a flexibility that allows the fluid impermeable barrier 102 and the fluid permeable membrane 130 to accommodate the size and/or shape changes discussed above. The fluid permeable membrane 130 also covers the bladder 114 thereby protecting the bladder 114 from objects that may puncture the bladder 114. The fluid impermeable barrier 102 may also cover at least a portion of the bladder 114 thereby also protecting the bladder 114 from objects. The bladder 114 may be positioned in the chamber 106 so the bladder 114 does not obstruct or only slight obstructs bodily fluids from flowing through the fluid permeable membrane 130 to the fluid permeable support 132. For example, the bladder 114 may be positioned so, at most, only a small portion of the bladder 114 (e.g., at most 20%, at most 10%, or at most 5%) is not positioned between the fluid impermeable barrier 102 and the support 132.

In some examples, the fluid permeable membrane 130 may be optional. For example, the porous material 110 may include only the fluid permeable support 132. In such examples, the bladder 114 may be positioned within the fluid permeable support 132 since, for instance, at least some materials of the support 132 disclosed herein are flexible enough to accommodate the shape and/or size changes discussed herein. In some examples, the fluid permeable support 132 may be optionally omitted from the fluid collection assembly 100 and the porous material 110 may only include the fluid permeable membrane 130. In such examples, the bladder 114 may be positioned within the fluid permeable membrane 130.

In an embodiment, the fluid permeable membrane 130 and/or the fluid permeable support 132 are wicking materials. In such an embodiment, the fluid permeable support 132 may have a greater ability to wick the bodily fluids than the fluid permeable membrane 130, such as to move the bodily fluids inwardly from the fluid permeable membrane 130. In some examples, the wicking ability of the fluid permeable support 132 and the fluid permeable membrane 130 may be substantially the same. In an embodiment, the fluid permeable membrane 130 and/or the fluid permeable support 132 are non-wicking materials (e.g., absorbent and/or adsorbent materials).

In an embodiment, not shown, the fluid permeable membrane 130 and the fluid permeable support 132 may at least substantially completely fill the portions of the chamber 106 not occupied by the inflation device 112 and the conduit 128. In an embodiment, as shown in FIG. 1D, the fluid permeable membrane 130 and the fluid permeable support 132 may not substantially completely fill the portions of the chamber 106 not occupied by the inflation device 112 or the conduit 128. In such an embodiment, the fluid collection assembly 100 includes the fluid reservoir 133 disposed in the chamber 106.

The fluid reservoir 133 is a substantially unoccupied portion of the chamber 106. The fluid reservoir 133 may be defined between the fluid impermeable barrier 102 and at least one of the inflation device 112, the fluid permeable membrane 130, or the fluid permeable support 132. The bodily fluids in the chamber 106 may flow through the fluid permeable membrane 130 and/or fluid permeable support 132 to the fluid reservoir 133. The fluid reservoir 133 may retain of the bodily fluids. The bodily fluids in the chamber 106 may flow through the fluid permeable membrane 130 and/or fluid permeable support 132 and, optionally, to the fluid reservoir 133. The fluid impermeable barrier 102 may retain the bodily fluids in the fluid reservoir 133. The fluid reservoir 133 may be in a portion of the chamber 106 designed to be in a gravimetrically low point of the fluid collection assembly 100 when the fluid collection assembly 100 is worn.

Figure 2A:
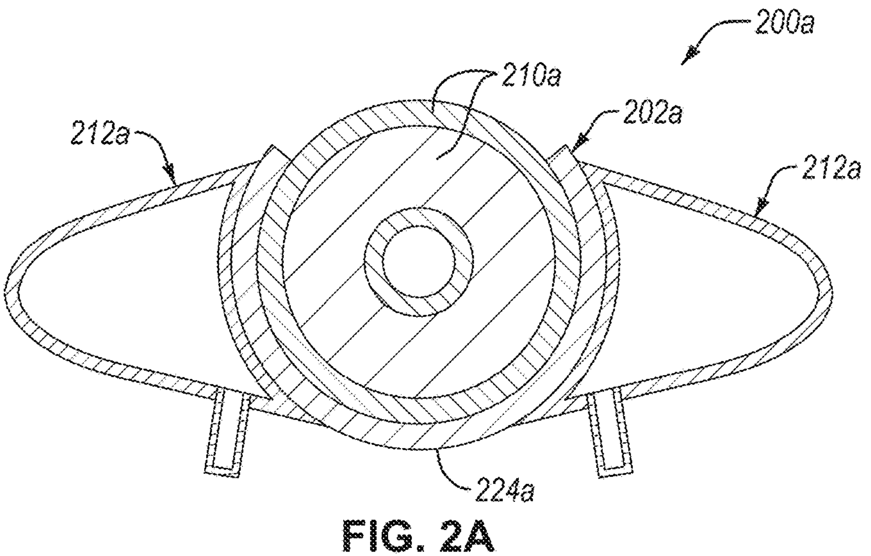
FIGS. 2A to 2C are schematic cross-sectional views of different fluid collection assemblies that each have inflation devices positioned differently, according to different embodiments.
Figure 2B:
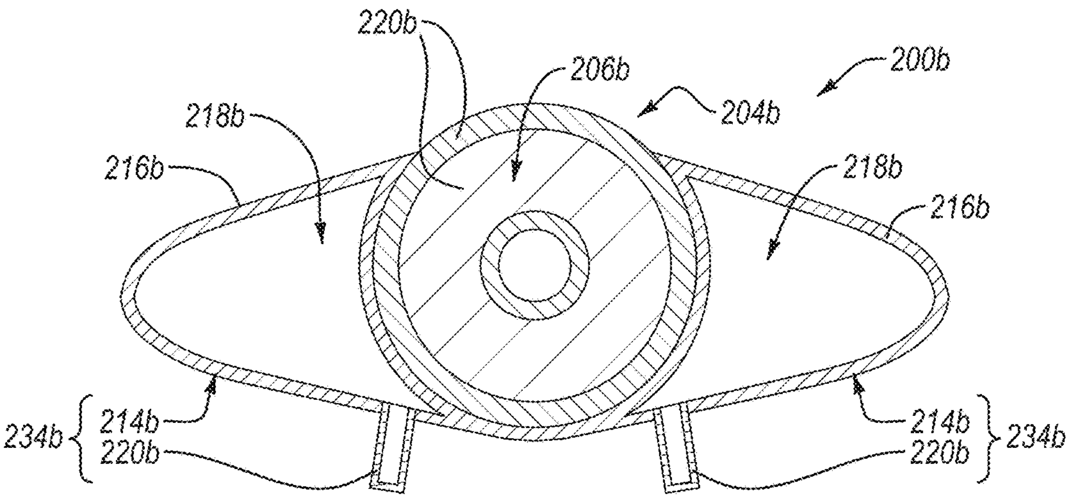
Figure 2C:
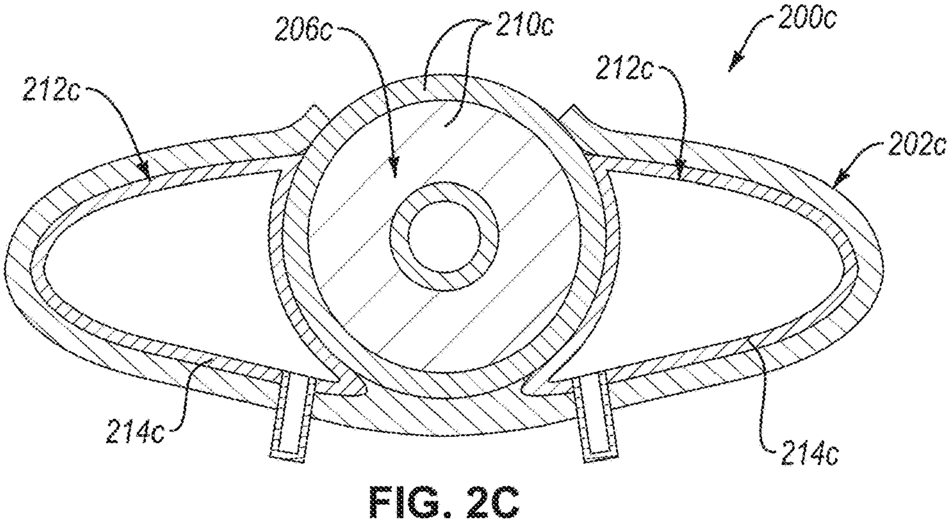

The inflation devices disclosed herein may be positioned in locations of the fluid collection assemblies disclosed herein other than between the fluid permeable membrane and the fluid permeable support. For example, FIGS. 2A to 2C are schematic cross-sectional views of different fluid collection assemblies that each have the inflation devices positioned differently, according to different embodiments. Except as otherwise disclosed herein, the fluid collection assemblies illustrated in FIGS. 2A-2C may be the same or substantially similar to any of the fluid collection assemblies disclosed herein. For example, the fluid collection assemblies illustrated in FIGS. 2A-2C may include a fluid impermeable barrier defining an opening, chamber, and fluid outlet; at least one porous material; and a conduit.

Referring to FIG. 2A, a fluid collection assembly 200*a* includes a fluid impermeable barrier 202*a* and at least one porous material 210*a*. The fluid impermeable barrier 202*a* includes an outer surface 224*a*. The fluid collection assembly 200*a* includes an inflation device 212*a* that is distinct from the fluid impermeable barrier 202*a*. The inflation device 212*a* is positioned on and attached to at least a portion of the outer surface 224*a*. For example, the inflation device 212*a* may be attached to the outer surface 224*a* using an adhesive, ultrasonic welding, heat staking, or any other suitable technique. Since the inflation device 212*a* is disposed on the outer surface 224*a*, switching the fluid collection assembly 202*a* and the inflation device 212*a* between different states will have limited effect on the size and shape of the fluid impermeable barrier 202*a* and the porous material 210*a* compared to the fluid impermeable barrier 102 and the fluid permeable membrane 130 shown in FIGS. 1A-1D. The fluid impermeable barrier 202*a* and the porous material 210*a* may, optionally, be formed from more rigid materials than the fluid impermeable barrier 102 and the fluid permeable membrane 130 shown in FIGS. 1A-1D. Positioning the inflation device 212*a* on the outer surface 224*a* may make manufacturing of the fluid collection assembly 200*a* easier since the inflation device 212*a* need not be positioned between two components of the fluid collection assembly 200*a*.

Referring to FIG. 2B, the fluid collection assembly 200*b* includes an inflation barrier 234*b*. The inflation barrier 234*b* is a fluid impermeable barrier and an inflation device integrally formed together. The inflation barrier 234*b* may exhibit any of the properties and functions as any of the fluid impermeable barriers and inflation devices disclosed herein. For example, the inflation barrier 234*b* may define an opening 204*b*, a chamber 206*b*, and a fluid outlet (not shown) and may be configured to prevent bodily fluids from leaking from the chamber 206*b*. The inflation barrier 234*b* may also include a bladder 214*b* and a valve 220*b*. The bladder 214*b* includes one or more walls 216*b* defining an interior region 218*b*. The inflation barrier 234*b* is configured to switch between one or more states (e.g., a first state and a second state) by adding or removing fluids from an inflation region 218 using the valve 220.

Switching the fluid collection assembly 202*b* and the inflation barrier 234*b* between different states will have limited effect on the size and shape of the porous material 210*b* compared to the fluid impermeable barrier 130 shown in FIGS. 1A-1C. The porous material 210*b* may, optionally, be formed from more rigid materials than the fluid permeable membrane 130 shown in FIGS. 1A-1C. Further, the inflation barrier 234*b* may make manufacturing of the fluid collection assembly 200*b* easier since the inflation barrier 234*b* need not be positioned between two components of the fluid collection assembly 200*b* and decreases the number of components that form the fluid collection assembly 200*b*.

Referring to FIG. 2C, the fluid collection assembly 200*c* includes a fluid impermeable barrier 202*c* and at least one porous material 210*c*. The fluid collection assembly 200*c* also includes an inflation device 212*c* that is distinct from the fluid impermeable barrier 202*c*. At least a portion of the inflation device 212*c* (e.g., at least the bladder 214*c*) is positioned between the fluid impermeable barrier 202*c* and the porous material 210*c*. The fluid impermeable barrier 202*c* may protect the inflation device 212*c* from objects that may puncture the inflation device 212*c*. Since the inflation device 212*c* is disposed between the fluid impermeable barrier 202*c* and the porous material 210*c*, switching the fluid collection assembly 202*c* and the inflation device 212*c* between different states will have limited effect on the size and shape of the porous material 210*c* compared to the porous material 110 shown in FIGS. 1A-1D. The porous material 210*c* may, optionally, be formed from more rigid materials than the fluid permeable membrane 130 shown in FIGS. 1A-1D. Positioning the inflation device 212*c* between the fluid impermeable barrier 202*c* and the porous material 210*c* may make manufacturing of the fluid collection assembly 200*c* easier since the inflation device 212*c* may be positioned in the chamber 206*c* before or while the porous material 210*c* is positioned in the chamber 206*c*. The method for forming the fluid collection assembly 200*c* does not require the additional step of positioning the inflation device 212*c* in the porous material 210*c*.

It is noted that the inflation devices disclosed herein may have positions other that the positions illustrated in FIGS. 1B and 2A-2C. For example, the inflation devices may be positioned within the fluid permeable membrane, within the fluid permeable support, between the fluid permeable support and the conduit, within the conduit, or integrally formed with the conduit.

Figure 3:
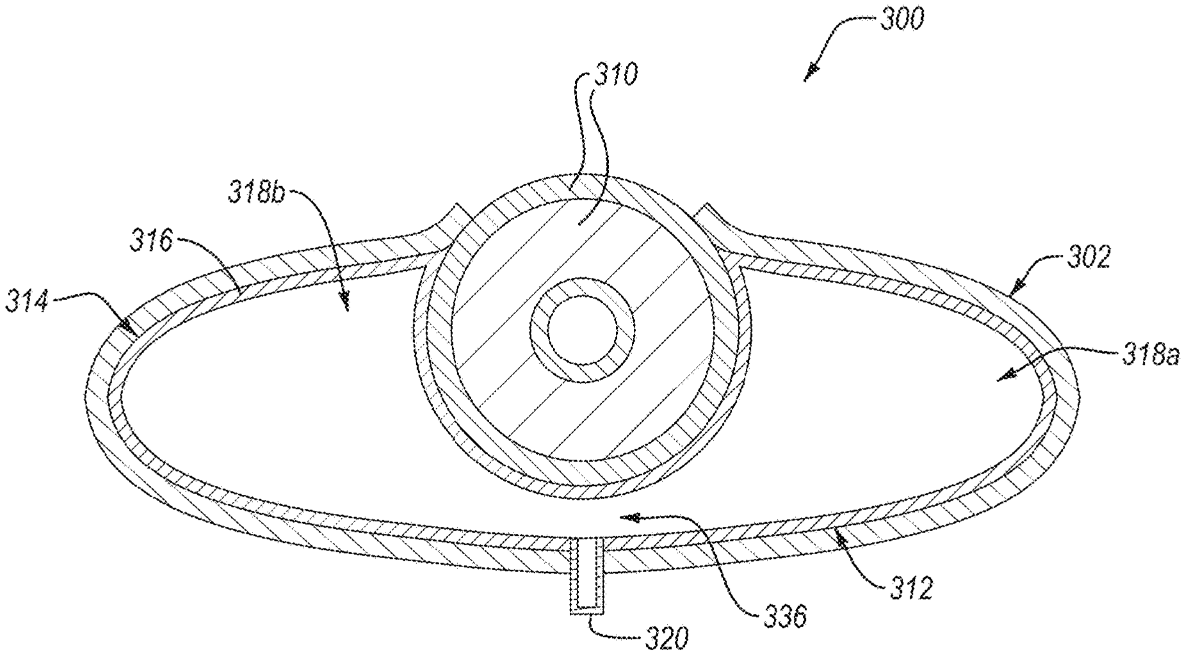
FIG. 3 is a cross-sectional schematic view of a fluid collection assembly when the at least one bladder thereof is in the second state, according to an embodiment.

FIG. 3 is a cross-sectional schematic view of a fluid collection assembly 300 when the at least one bladder thereof is in the second state, according to an embodiment. Except as otherwise disclosed herein, the fluid collection assembly 300 is the same or substantially similar to any of the fluid collection assemblies disclosed herein. For example, the fluid collection assembly 300 includes a fluid impermeable barrier 302 and at least one porous material 310. The fluid collection assembly 300 also includes at least one inflation device 312. In an embodiment, as illustrated, at least a portion of the inflation device 312 is positioned between the fluid impermeable barrier 302 and the porous material 310. However, the inflation device 312 may include any of the other positions disclosed herein.

The inflation device 312 includes a bladder 314. The first bladder 314 includes one or more walls 316. The one or more walls 316 define a first inflation region 318*a* and a second inflation region 318*b*. The inflation device 312 includes at least one passageway 336 extending between and fluidly coupling the first inflation region 318*a* to the second inflation region 318*b*. For example, the one or more walls 316 defines the passageway 336. Inflation fluids present in the first inflation region 318*a* may flow to the second inflation region 318*b* by entering the passageway 336, flowing through the passage way 336, and then exiting the passageway 336 and vice versa. The pressure inside each of the first inflation region 318*a* and the second inflation region 318*b* remains the same thereby preventing over inflation or under inflation of one of the first inflation region 318*a* or the second inflation region 318*b*.

In an embodiment, the inflation device 312 may include a single valve 320 since the first inflation region 318*a* is in fluid communication with the second inflation region 318*b*. The valve 320 may be in direct fluid communication with one of the first inflation region 318*a*, the second inflation region 318*b*, or the passageway 336. However, it is noted that the inflation device 312 may include at least one valve 320 that is in direct fluid communication with at least two of the first inflation region 318*a*, the second inflation region 318*b*, or the passageway 336.

In an embodiment, inflation device 310 may include one or more additional inflation regions (not shown) that are in fluid communication with the first inflation region 318*a* and the second inflation region 318*b* through the passageway 336 or through one or more additional passageways. In an embodiment, the passageway 336 may include a passageway valve that selective permits or restricts fluid flow between the first inflation region 318*a* to the second inflation region 318*b*. For example, the passageway valve may be open (e.g., permit fluid flow between the first inflation region 318*a* and the second inflation region 318*b*) when it is desirable for the first inflation region 318*a* and the second inflation region 318*b* to exhibit the same pressure. However, the passageway valve may be closed when it is desirable to independently inflate at least one of the first inflation region 318*a* or the second inflation region 318*b* (e.g., when it is desirable for one of the first inflation region 318*a* or the second inflation region 318*b* to be inflated more than the other). The passageway valve may include any suitable valve, such as a mechanical valve or a clamp.

Figure 4A:
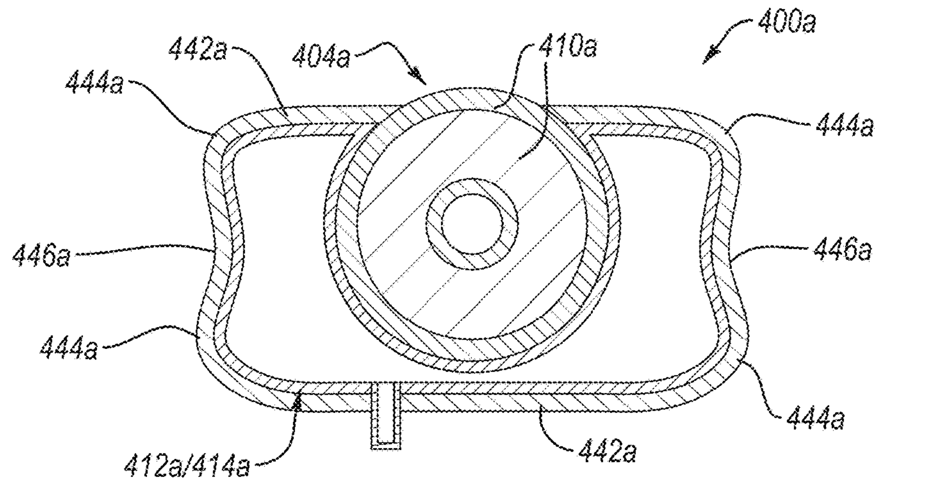
FIGS. 4A to 4C are schematic cross-sectional views of fluid collection assemblies exhibiting different shapes when the bladders of the fluid collection assemblies are in the second state, according to different embodiments.
Figure 4B:
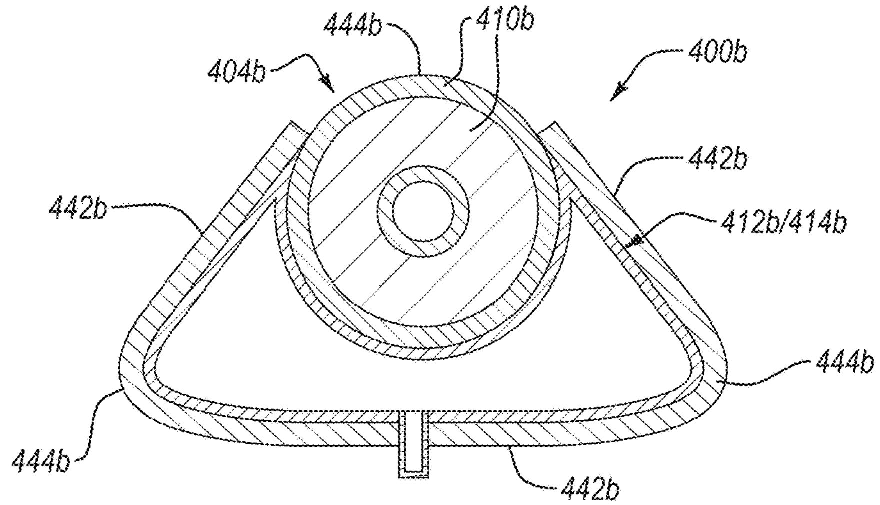
Figure 4C:
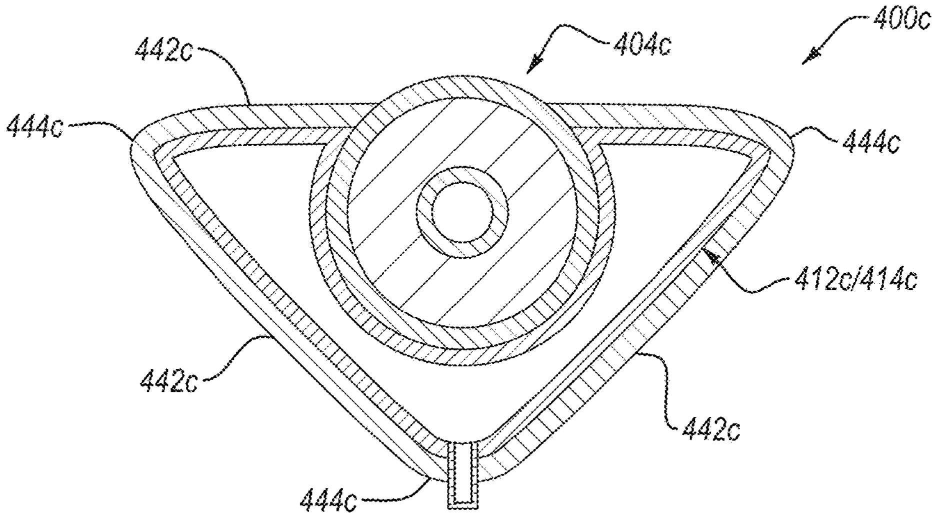

The fluid collection assemblies illustrated in FIGS. 1C and 2A-3 exhibit the same general oblong cross-sectional shape when the bladders of the fluid collection assemblies are in the second state. However, it is noted that the fluid collection assemblies may exhibit other cross-sectional shapes, without limitation. FIGS. 4A to 4C are schematic cross-sectional views of fluid collection assemblies exhibiting different shapes when the bladders of the fluid collection assemblies are in the second state, according to different embodiments. Except as otherwise disclosed herein, the fluid collection assemblies illustrated in FIGS. 4A-4C are the same or substantially similar to any of the fluid collection assemblies disclosed herein. For example, the fluid collection assemblies include fluid impermeable barrier, at least one porous material, and at least one inflation device. In an embodiment, as illustrated, the inflation device is positioned between the fluid impermeable barrier and the porous material. However, it is noted that the inflation device may have any of the positions disclosed herein.

Regarding FIG. 4A, a fluid collection assembly 400*a* includes an inflation device 412*a*. The inflation device 412*a* includes at least one bladder 414*a*. When the bladder 414*a* is in the second state, the fluid collection assembly 400*a* exhibits a generally hour-glass cross-sectional shape. Similarly, when the bladder 414*a* is in the second state, the bladder 414*a* may form a generally hour-glass cross-sectional shape that corresponds to the generally hour-glass cross-sectional shape of the fluid collection assembly 400*a* except that the bladder 414*a* defines a cutout in which some components of the fluid collection assembly 400*a* (e.g., the at least one porous material 410*a*) may be positioned. In an embodiment, as illustrated, the bladder 414*a* includes a plurality of bladders each in fluid communication with each other. In an embodiment, the bladder 414*a* may include a plurality of bladders not in fluid communication with each other. In an embodiment, the bladder 414*a* may include a single bladder.

The generally hour-glass shape of the fluid collection assembly 400*a* includes two opposing edges 442*a*, four apexes 444*a* at the ends of the edges 442*a*, and two concave surfaces 446*a* extending between adjacent apexes 444*a*. The opening 404*a* is formed on one edge 442*a*. The two apexes 444*a* that are most proximate to the opening 404*a* are configured to fit at least partially in the fold formed between the inner thighs and the rest of the pubic region of the patient. The concave surfaces 446*a* are configured to press against and generally correspond to the convex shape inner thighs of the patient. The ability of the two apexes 444*a* to fit at least partially into the fold formed between the inner thighs and the rest of the pubic region and the concave surfaces 446*a* to correspond to the concave inner thighs help secure the fluid collection assembly 400*a* to the patient, maintain the opening 404*a* against the vulva of the patient, and make the fluid collection assembly 400*a* more comfortable compared to some other shapes.

Regarding FIG. 4B, a fluid collection assembly 400*b* includes an inflation device 412*b*. The inflation device 412*b* includes at least one bladder 414*b*. When the bladder 414*b* is in the second state, the fluid collection assembly 400*b* exhibits a generally triangular cross-sectional shape. Similarly, when the bladder 414*b* is in the second state, the bladder 414*b* may also form a generally triangular cross-sectional shape that corresponds to the generally triangular cross-sectional shape of the fluid collection assembly 400*b* except that the bladder 414*b* defines a cutout in which some components of the fluid collection assembly 400*b* (e.g., the at least one porous material 410*b*) may be positioned. In an embodiment, as illustrated, the bladder 414*b* may include a single bladder. In an embodiment, the bladder 414*b* includes a plurality of bladders each in fluid communication with each other. In an embodiment, the bladder 414*b* may include a plurality of bladders not in fluid communication with each other.

The generally triangular cross-sectional shape of the fluid collection assembly 400*b* includes three edges 442*b* and three apexes 444*b* at the intersection of each edge 442*b*. The opening 404*b* is formed at one of the three apexes 444*b* which allows that porous material 410*b* to partially fit between the labia and to press more closely to the urethral opening of the patent. Positioning a portion of the porous material 410*b* between the labia helps secure the fluid collection assembly 400*b* to the patient.

FIG. 4C illustrates a fluid collection assembly 400*c* that, except as otherwise disclosed herein, in the same as the fluid collection assembly 400*b* of FIG. 4B. For example, when the bladder 414*c* of the inflation device 412*c* is in the second state, the fluid collection assembly 400*c* exhibits a generally triangular cross-sectional shape and the bladder 414*c* exhibits a corresponding generally triangular cross-sectional shape with a cutout. However, the opening 404*c* is formed in one edge 442*c*. Forming the opening 404*c* allows two of the apexes 444*c* that are closest to the opening 404*c* to fit into the fold between the inner thighs and the rest of the pubic region. Fitting the edges 442*c* into the fold helps secure the fluid collection assembly 400*c* to the patient. Further, the two edges 442*c* that do not include the opening 404*c* better conform to the convex shape of the inner thighs of the patient compared to the fluid collection assembly 400*b* of FIG. 4B which may make the fluid collection assembly 400*c* more comfortable to use.

Figure 5A:
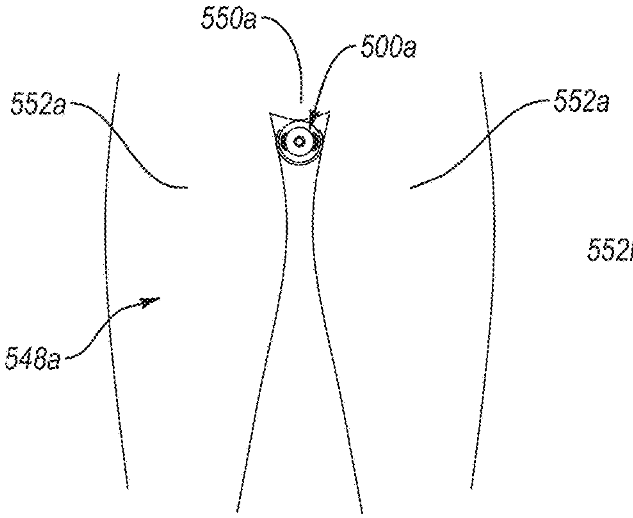
FIG. 5A is a schematic illustration of a first fluid collection assembly being used with a first female patient, according to an embodiment.

FIG. 5A is a schematic illustration of a first fluid collection assembly 500*a* being used with a first female patient 548*a*, according to an embodiment. During use, the first fluid collection assembly 500*a* is positioned between the thighs 552*a* of the first female patient 548*a* so the opening 504*a* of the first fluid collection assembly 500*a* is adjacent to the vulva 550*a* of the first female patient 548*a*. The first fluid collection assembly 500*a* may include any of the fluid collection assemblies disclosed herein that are configured to be used with a female patient. The thighs 552*a* of the first female patient 548*a* are sufficiently large that the first fluid collection assembly 500*a* presses against the thighs of the first female patient 548*a* even when the bladder of the first fluid collection assembly 500*a* is in the first state. The first fluid collection assembly 500*a* may be conformed to the vulva 550*a* and other portions of the pubic region of the first female patient 548*a* and the thighs 552*a* of the first female patient 548*a* may maintain the shape of the first fluid collection assembly 500*a*. The first fluid collection assembly 500*a* may be used with female patients whose thighs are sufficiently large that the first fluid collection assembly 500*a* need not be inflated even though the first fluid collection assembly 500*a* can be inflated.

Figure 5B:
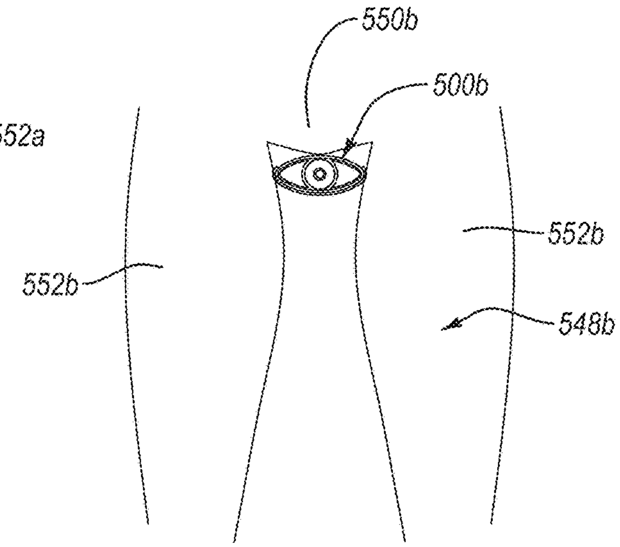
FIG. 5B is a schematic illustrated of a second fluid collection assembly being used with a second female patient, according to an embodiment.

FIG. 5B is a schematic illustrated of a second fluid collection assembly 500*b* being used with a second female patient 548*b*, according to an embodiment. During use, the second fluid collection assembly 500*b* is positioned between the thighs 552*b* of the second female patient 548*b* so the opening 504*b* of the second fluid collection assembly 500*b* is adjacent to the vulva 550*b* of the first female patient 548*b*. The second fluid collection assembly 500*b* is the same as the first fluid collection assembly 500*a*. The thighs 552*b* of the second female patient 548*b* are sufficiently small that the second fluid collection assembly 500*b* does not contact the thighs 552*b* or does not contact the thighs 552*b* with sufficient force to keep the second fluid collection assembly 500*b* conformed to the pubic region of the second female patient 548*b*. The bladder of the second fluid collection assembly 500*b* may be inflated from the first state to the second state. The second fluid collection assembly 500*b* is sufficiently inflated in the second state that the second fluid collection assembly 500*b* presses against the thighs 552*b* of the second female patient 548*b* with sufficient force that the thighs 552*b* keep the second fluid collection assembly 500*b* conformed to the pubic region. FIG. 5B illustrates how the fluid collection assemblies disclosed herein may be used with female patients that are underweight or have thin thighs.

Figure 6:
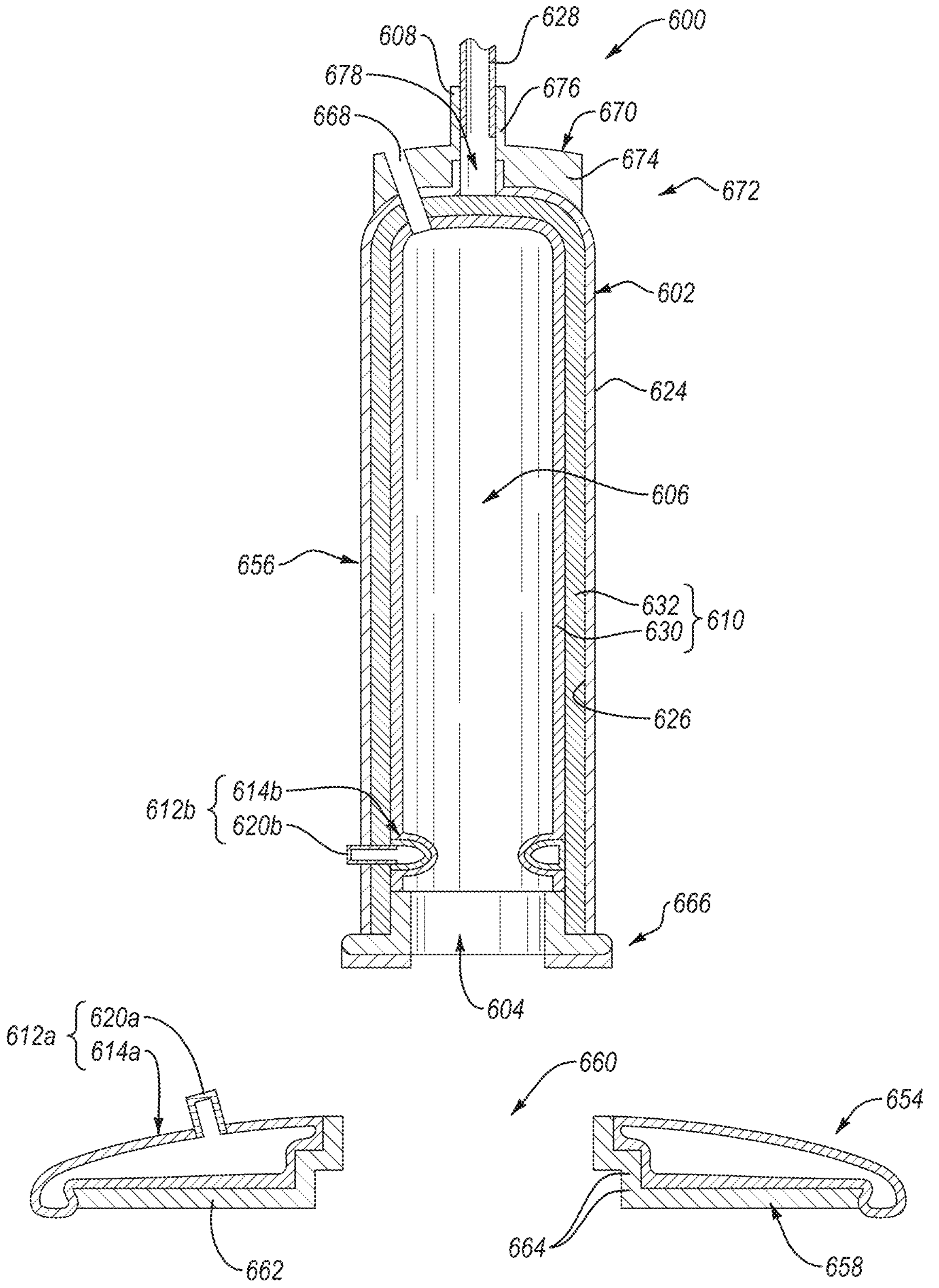
FIG. 6 is a cross-sectional view of a male fluid collection assembly, according to an embodiment.

The fluid collection assemblies shown in FIGS. 1A-5B are examples of female fluid collection assemblies configured to collect bodily fluids from females (e.g., collection urine from a female urethral opening). However, the fluid collection assemblies, systems, and method disclosed herein may include male fluid collection assemblies shaped, sized, and otherwise configured to collection bodily fluids from males (e.g., collection urine from a penis). FIG. 6 is a cross-sectional view of a male fluid collection assembly 600, according to an embodiment.

The fluid collection assembly 600 includes a receptacle 654 and a sheath 656. The receptacle 654 is sized, shaped, and made of a material to be coupled to skin that surrounds the penis (mons pubis, testicles, perineum, etc.) and have the penis positioned therethrough. For example, the receptacle 654 may include an annular base 658 that defines an opening 660 in the receptacle 654. The annular base 658 is sized and shaped to be positioned around the penis and have the penis positioned therethrough. The annular base 658 may also be sized, shaped, made of a material, or otherwise configured to be coupled (e.g., adhesively attached, such as with a hydrogel adhesive) to the skin around the penis. In an example, the annular base 658 may exhibit the general shape or contours of the skin surface that the annular base 658 is selected to be coupled with. The annular base 658 may be flexible thereby allowing the annular base 658 to conform to any shape of the skin surface. The annular base 658 may include a laterally extending flange 662. The receptacle 654 also defines a hollowed region configured to receive (e.g., seal against) the sheath 656. For example, the receptacle 654 may include a longitudinally extending flange 664 that extends upwardly from the annular base 658. The longitudinally extending flange 664 may be tall enough to prevent the sheath 656 from being accidentally removed from the receptacle 654 (e.g., at least 0.25 cm tall, 1 cm tall, at least 9 cm tall, or at least 5 cm tall). The receptacle 654 is at a proximal region 666 (regarding a patient) of the fluid collection assembly 600.

The sheath 656 includes (e.g., may be formed from) a fluid impermeable barrier 602 sized and shaped to fit into the hollowed region of the receptacle 654. For example, the sheath 656 may be generally tubular or cup-shaped, as shown. The generally tubular or cup-shaped fluid impermeable barrier 602 may at least partially define the outer surface 624 of the sheath 656. The fluid impermeable barrier 602 may be similar or identical to the fluid impermeable barrier 102 as disclosed herein, in one or more aspects. For example, the fluid impermeable barrier 602 may be constructed of any of the materials disclosed herein for the fluid impermeable barrier 102. The fluid impermeable barrier 602 at least partially defines the chamber 606. For example, the inner surface 626 of the fluid impermeable barrier 602 at least partially defines the perimeter of the chamber 606. The chamber 606 may be similar or identical to the chamber 106 in one or more aspects. For example, the chamber 606 may at least temporarily retain fluids. As shown, the fluid collection assembly 600 may include at least one porous material 610. The porous material 610 may be similar or identical to the porous material 110 in one or more aspects. For example, the porous material 610 may include one or more of a fluid permeable membrane 630 or a fluid permeable support 632. The fluid impermeable barrier 602 may also define an opening 604 extending through the fluid impermeable barrier 602 configured to have a penis positioned therethrough.

The sheath 656 and fluid impermeable barrier 602 may also include at least one aperture 668 (e.g., vacuum relief hole) that allows the chamber 606 to remain substantially at atmospheric pressure. The at least one aperture 668 may be at any point on the sheath 656, such as near or nearer the opening 660. In some examples (not shown), the aperture 668 may extend through the cap 670 or be disposed beneath the cap 670. In some examples, the fluid collection assembly 600 may not include the aperture 668, such as when a more complete seal as desired for the chamber 606.

The sheath 656 also includes at least a portion of the conduit 628, such as at least partially disposed in the chamber 606. For example, the conduit 628 may extend from the sheath 656 at the distal region 672 to a proximal region 666 at least proximate to the opening 660. The proximal region 666 may be disposed near or on the skin around the penis or pubic area therearound. When a patient lays on their back, bodily fluids may aggregate near the opening 660 against the skin of the patient. The bodily fluids may be removed from the chamber 606 via the conduit 628.

In some examples, the fluid impermeable barrier 602 may be constructed of a material and/or have a thickness that allows the sheath 656 to collapse when placed under vacuum, such as to remove air around a penis in the fluid collection assembly 600 during use. In such examples, the conduit 628 may extend only to or into the distal region 672 in the chamber 606 (e.g., not through to the area adjacent the opening). In such examples, bodily fluids may be collected and removed from the fluid collection assembly 600 at the end nearest the aperture 668. In such examples, the at least one aperture may be located nearest the opening 660.

In an example, portions of the chamber 606 may be substantially empty due to the varying sizes and rigidity of the male penis. However, in some examples, the outermost regions of the chamber 606 (e.g., periphery of the interior regions of the sheath 656) may include porous material 610 (e.g., one or more of the fluid permeable membrane 630 and fluid permeable support 632). For example, the porous material 610 may be bonded to the inner surface 626 of the fluid impermeable barrier 602. The porous material 610 may be positioned (e.g., at the distal end of the chamber 606) to blunt a stream of urine from the penis thereby limiting splashing and/or to direct the fluid(s) to a selected region of the chamber 606. Since the chamber 606 is substantially empty (e.g., substantially the chamber 606 forms a reservoir), the fluids are likely to pool at a gravimetrically low point of the chamber 606. The gravimetrically low point of the chamber 606 may be at an intersection of the skin of an patient and the fluid collection assembly 600, a corner formed in the sheath 656, or another suitable location depending on the orientation of the patient.

The porous material 610 may include one or more of the fluid permeable membrane 630 or the fluid permeable support 632. The fluid permeable membrane 630 and the fluid permeable support 632 may be similar or identical to the fluid permeable membrane 130 or the fluid permeable support 132 as respectively disclosed herein, in one or more aspects such as material make-up or wicking ability. One or more of the fluid permeable membrane 630 or the fluid permeable support 632 may be disposed between the fluid impermeable barrier 602 and a penis inserted into the chamber 606. The fluid permeable membrane 630 may be positioned between the fluid impermeable barrier 602 and a penis inserted into the chamber 606, such as between the fluid permeable support 632 and penis of a wearer as shown. The fluid permeable support 632 may be positioned between the fluid permeable membrane 630 and the fluid impermeable barrier 602. The inner surface 626, optionally including the end of the chamber 606 substantially opposite the opening 604, may be covered with one or both the fluid permeable membrane 630 or the fluid permeable support 632. The fluid permeable support 632 or the fluid permeable membrane 630 may be affixed (e.g., adhered) to the fluid impermeable barrier 602. The fluid permeable support 632 or the fluid permeable membrane 630 may be affixed to each other. In some examples, the porous material 610 only includes the fluid permeable membrane 630 or the fluid permeable support 632.

The fluid collection assembly 600 includes one or more inflation devices in one or more portions thereof. For example, the fluid collection assembly 600 will be discusses as having a first inflation device 612*a* and a second inflation device 612*b*. However, it is noted that the fluid collection assembly 600 may only include a single inflation device (e.g., the first inflation device 612*a*, the second inflation device 612*b*, or another inflation device) or three or more inflation devices (e.g., the first inflation device 612*a*, a second inflation device 612*b*, and another inflation device). The inflation devices of the fluid collection assembly 600 may be similar or identical to any of the inflation devices disclosed herein in one or more aspects. For example, the first inflation device 612*a* may include at least one first bladder 614*a* and at least one first valve 620*a* and the second inflation device 612*b* may include at least one second bladder 614*b* and at least one second valve 620*b*.

The first inflation device 612*a* may be disposed on (as shown) or in the receptacle 654. In an embodiment, the first inflation device 612*a* increases the width (measure perpendicular to the longitudinal axis of the fluid collection assembly 600) of the receptacle when the pubic region of the patient is large enough to accommodate the increased width. The increase width of the receptacle 654 increases the surface area of the receptacle 654 that contacts the patient which may facilitate securement of the receptacle 654. For example, the increased surface area may allow for additional adhesive to be applied to the surface of the receptacle 654 that contacts the patient. In an embodiment, the first inflation device 612*a* changes the cross-sectional shape (measured perpendicular to the longitudinal axis of the fluid collection assembly 600) of the receptacle 654 which allows the receptacle 654 to conform to differently shaped pubic regions. In an embodiment, the first inflation device 612*a* increases a thickness of the receptacle 654 which may increase a contact pressure that, at least partially, secures the receptacle 654 to the pubic region.

The second inflation device 612*b* may be disposed on or in (as shown) the sheath 656. The second inflation device 612*b* may be configured to decrease a width of the chamber 606. For example, decreasing the width of the chamber 606 may cause the sheath 656 to contact a smaller diameter penis, a non-erect penis, or to conform to a penis that is transitioning between erect and non-erect states. Decreasing the width of the chamber 606 may inhibit bodily fluids from flowing away from the fluid outlet 608 thereby facilitating removal of the bodily fluids from the chamber 606.

In some examples, the fluid collection assembly 600 includes a cap 670 at a distal region 672. The cap 670 defines an fluid outlet 608 through which the fluids may be removed from the fluid collection assembly 600. The fluid outlet 608 is in fluid communication with the chamber 606. The cap 670 may be disposed over at least a portion of the distal region 672 of one or more of the fluid impermeable barrier 602 or the porous material 610. The cap 670 may be made of a polymer, rubber, or any other fluid impermeable material. The cap 670 may be attached to one or more of the fluid impermeable barrier 602, the porous material 610, or the conduit 628. The cap 670 may have a laterally extending flange 674 and a longitudinally extending flange 676. The laterally extending flange 674 may cover at least a portion of the distal region 672 of the fluid collection assembly 600. The longitudinally extending flange 676 may laterally extend a distance from the sheath 656. The longitudinally extending flange 676 is sized and configured to receive and fluidly seal against the conduit 628, such as within the fluid outlet 608. The conduit 628 may extend a distance within or through the cap 670, such as to the porous material 610, through the porous material 610, or to a point set-off from the porous material 610. In an example, the cap 670 may define a reservoir 678.

The reservoir 678 is an unoccupied portion of device such as in the cap 670 and is void of other material. In some examples, the reservoir 678 is defined at least partially by the porous material 610 and the cap 670. During use, the fluids in the chamber 606 may flow through the porous material 610 to the reservoir 678. The reservoir 678 may store at least some fluids and/or position the fluids for removal by the conduit 628. In some examples, at least a portion of the porous material 610 may extend continuously between at least a portion of the opening of the fluid outlet 608 and chamber 606 to wick any fluid from the opening directly to the reservoir 678.

In some examples (not shown), the fluid impermeable barrier 602 may be disposed on or over the cap 670, such as enclosing the cap 670 within the chamber 606.

In some examples, the sheath 656 may include at least a portion of the conduit 628, such as at least partially disposed in the chamber 606. For example, the conduit 628 may extend from the sheath 656 to a region at least proximate to the opening 660. The inlet of the conduit 628 may be positioned adjacent to the annular base 658. The inlet of the conduit 628 may be positioned to be adjacent or proximate to the gravimetrically low point of the chamber 606, such as adjacent to the annular base 658. For example, the inlet may be co-extensive with or offset from the opening 660. In examples, the inlet may be positioned adjacent to the distal region 672 of the sheath 656 (e.g., substantially opposite the opening).

The proximal region 666 may be disposed near or on the skin around the penis and the inlet of the conduit 628 may be positioned in the proximal region 666. The outlet of the conduit 628 may be directly or indirectly coupled to a vacuum source. Fluid may be removed from the proximal region 666 of the chamber 606 via the conduit 628.

The receptacle 654, the sheath 656, the cap 670, and the conduit 628 may be attached together using any suitable method. For example, at least two of the receptacle 654, the sheath 656, the cap 670, or the conduit 628 may be attached using at least one of an interference fit, an adhesive, stitching, welding (e.g., ultrasonic welding), tape, any other suitable method, or combinations thereof.

In some examples (not shown), the fluid collection assembly 600 may have a one piece design, with one or more of the sheath 656, the receptacle 654, and the cap 670 being a single, integrally formed piece.

Figure 7:
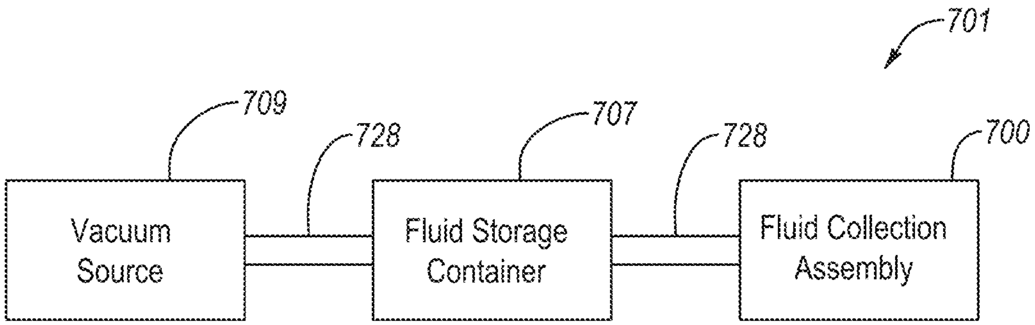
FIG. 7 is a block diagram of a system for fluid collection, according to an embodiment.

Also as shown, the conduit 628 may be at least partially disposed with the chamber of a fluid collection assembly. The conduit 628 may extend from the distal region 672 to the proximal region 666. For example, the conduit 628 may extend through the cap 670 to a point adjacent to the receptacle 654. The conduit 628 is sized and positioned to be coupled to a fluid storage container or the vacuum source (FIG. 7). An outlet of the conduit 628 may be operably coupled to the vacuum source, directly or indirectly. The inlet of the conduit 628 may be positioned within the chamber 606 such as at a location expected to be at the gravimetrically low point of the fluid collection assembly during use. By positioning the inlet in a location expected to be at the gravimetrically low point of the fluid collection assembly when worn by the user, fluids introduced into the chamber 606 may be removed via the conduit 628 to prevent pooling or stagnation of the fluid within the chamber 606.

In some examples, the vacuum source may be remotely located from the fluid collection assembly 600. In such examples, the conduit 628 may be fluidly connected to the fluid storage container, which may be disposed between the vacuum source and the fluid collection assembly 600.

During operation, a male using the fluid collection assembly 600 may discharge fluid(s) (e.g., urine) into the chamber 606. The fluid(s) may pool or otherwise be collected in the chamber 606. At least some of the fluid(s) may be pulled through the interior of the conduit 628 via the inlet. The fluid may be drawn out of the fluid collection assembly 600 via the vacuum/suction provided by the vacuum source. During operation, the aperture 668 may substantially maintain the pressure in the chamber 606 at atmospheric pressure even though fluid is introduced into and removed from the chamber 606.

Additional examples of male fluid collection assemblies that may include one or more inflation devices are disclosed in U.S. patent application Ser. No. 16/433,773 filed on Jun. 6, 2019, the disclose of which is incorporated herein, in its entirety, by this reference.

FIG. 7 is a block diagram of a system 701 for fluid collection, according to an embodiment. The system 701 includes a fluid collection assembly 700, a fluid storage container 707, and a vacuum source 709. The fluid collection assembly 700, the fluid storage container 707, and the vacuum source 709 may be fluidly coupled to each other via one or more conduits 728. For example, fluid collection assembly 700 may be operably coupled to one or more of the fluid storage container 707 or the vacuum source 709 via the conduit 728. Fluid (e.g., urine or other bodily fluids) collected in the fluid collection assembly 700 may be removed from the fluid collection assembly 700 via the conduit 728 which protrudes into the fluid collection assembly 700. For example, an inlet of the conduit 728 may extend into the fluid collection assembly 700, such as to a reservoir. The outlet of the conduit 728 may extend into the fluid collection assembly 700 or the vacuum source 709. Suction force may be introduced into the chamber of the fluid collection assembly 700 via the inlet of the conduit 728 responsive to suction (e.g., vacuum) force applied at the outlet of the conduit 728.

The suction force may be applied to the outlet of the conduit 728 by the vacuum source 709 either directly or indirectly. The suction force may be applied indirectly via the fluid storage container 707. For example, the outlet of the conduit 728 may be disposed within the fluid storage container 707 and an additional conduit 728 may extend from the fluid storage container 707 to the vacuum source 709. The vacuum source 709 may apply suction to the fluid collection assembly 700 via the fluid storage container 707. The suction force may be applied directly via the vacuum source 709. For example, the outlet of the conduit 728 may be disposed within the vacuum source 709. An additional conduit 728 may extend from the vacuum source 709 to a point outside of the fluid collection assembly 700, such as to the fluid storage container 707. In such examples, the vacuum source 709 may be disposed between the fluid collection assembly 700 and the fluid storage container 707.

The fluid collection assembly 700 may be similar or identical to any of the fluid collection assemblies disclosed herein in one or more aspects. The fluid collection assembly 700 may be shaped and sized to be positioned adjacent to a female urethral opening or receive a penis.

The fluid storage container 707 is sized and shaped to retain a fluid. The fluid storage container 707 may include a bag (e.g., drainage bag), a bottle or cup (e.g., collection jar), or any other enclosed container for storing bodily fluid(s) such as urine. In some examples, the conduit 728 may extend from the fluid collection assembly 700 and attach to the fluid storage container 707 at a first point. An additional conduit 728 may attach to the fluid storage container 707 at a second point thereon and may extend and attach to the vacuum source 709. A vacuum (e.g., suction) may be drawn through fluid collection assembly 700 via the fluid storage container 707. Fluid, such as urine, may be drained from the fluid collection assembly 700 using the vacuum source 709.

The vacuum source 709 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 709 may provide a vacuum or suction to remove fluid from the fluid collection assembly 700. In some examples, the vacuum source 709 may be powered by one or more of a power cord (e.g., connected to a power socket), one or more batteries, or even manual power (e.g., a hand operated vacuum pump). In some examples, the vacuum source 709 may be sized and shaped to fit outside of, on, or within the fluid collection assembly 700. For example, the vacuum source 709 may include one or more miniaturized pumps or one or more micro pumps. The vacuum sources 709 disclosed herein may include one or more of a switch, a button, a plug, a remote, or any other device suitable to activate the vacuum source 709.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean ±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

The invention claimed is:

1. A fluid collection assembly, comprising:

a fluid impermeable barrier defining a chamber, at least one opening, and at least one fluid outlet;

at least one porous material disposed in the chamber;

at least one inflation device including at least one bladder and at least one valve, the at least one bladder including one or more walls defining at least one interior region, the at least one valve configured to allow at least one inflation fluid to flow at least into the at least one interior region to switch the at least one bladder from a first state to at least a second state, wherein an amount of the at least one inflation fluid present in the at least one interior region is greater when the at least one bladder is in the second state than when the at least one bladder is in the first state, wherein switching the at least one bladder between the first state and the second state changes least one of a width or a cross-sectional shape of the fluid collection assembly, wherein the width and the cross-sectional shape are measured perpendicularly to the longitudinal axis of the fluid collection assembly; and a conduit disposed in the fluid outlet.

2. The fluid collection assembly of claim 1, wherein at least partially of the at least one inflation device is attached to at least a portion of at least one outer surface of the fluid impermeable barrier.

3. The fluid collection assembly of claim 1, wherein at least a portion of the at least one inflation device is positioned between the fluid impermeable barrier and the at least one porous material.

4. The fluid collection assembly of claim 1, wherein:

the at least one porous material includes at least one fluid permeable membrane and at least one fluid permeable support; and at least a portion of the inflation device is positioned between the at least one preamble membrane and the at least one fluid permeable support.

5. The fluid collection assembly of claim 1, wherein the at least one bladder includes a plurality of bladders and the at least one inflation device includes at least one passageway extending between at least two of the plurality of inflation devices.

6. The fluid collection assembly of claim 1, wherein the at least one inflation device includes two inflation devices, the conduit positioned between the two inflation devices.

7. The fluid collection assembly of claim 6, wherein the fluid impermeable barrier includes a back wall opposite the at least one opening and two lateral walls extending from the at least one opening to the back wall, each the two inflation devices attached to, abutting, or integrally formed with one of the two lateral walls.

8. The fluid collection assembly of claim 1, wherein the fluid impermeable barrier includes a back wall opposite the at least one opening, the at least one valve extending through, directly from, or adjacent to the back wall.

9. The fluid collection assembly of claim 1, wherein the fluid impermeable barrier includes a back surface opposite the at least one opening, the at least one valve extending from or near the back surface.

10. The fluid collection assembly of claim 1, wherein the at least one valve includes a check valve.

11. The fluid collection assembly of claim 1, wherein the at least one valve includes a two-way valve.

12. The fluid collection assembly of claim 1, wherein the fluid collection assembly exhibits a first width when the at least one inflation element is in the first state and a second width when the at least one bladder is in the second state, wherein the first width is less than the second width, the first width and the second width measured perpendicular to a longitudinal axis of the fluid collection assembly.

13. The fluid collection assembly of claim 1, wherein the fluid collection assembly exhibits a first cross-sectional shape when the at least one inflation element is in the first state and a second cross-sectional shape when the at least one bladder is in the second state, wherein the first shape is different than the second shape, the first cross-sectional shape and the second cross-sectional shape measured perpendicular to the longitudinal axis of the fluid collection assembly.

14. The fluid collection assembly of claim 13, wherein the first cross-sectional shape is generally circular and the second cross-sectional shape is one of generally oblong, generally triangular, or generally hourglass shaped.

15. The fluid collection assembly of claim 1, wherein the fluid collection assembly exhibits a generally triangular cross-sectional shape when in at least one of the first state or the second state, the generally triangular cross-sectional shape measured perpendicular to the longitudinal axis of the fluid collection assembly.

16. The fluid collection assembly of claim 15, wherein the at least one opening is at an edge of the generally triangular cross-sectional shape.

17. The fluid collection assembly of claim 15, wherein the at least one opening is at an apex of the generally triangular cross-sectional shape.

18. The fluid collection assembly of claim 1, wherein the conduit is separate from the at least one inflation device.

19. A fluid collection assembly, comprising:

a fluid impermeable barrier defining a chamber, at least one opening, and at least one fluid outlet;

at least one porous material disposed in the chamber;

at least one inflation device including at least one bladder and at least one valve, the at least one bladder including one or more walls defining at least one interior region, the at least one valve configured to selectively permit at least one inflation fluid to flow into and out of the at least one interior region to switch the at least one bladder between a first state and at least a second state, wherein an amount of the at least one inflation fluid present in the at least one interior region is greater when the at least one bladder is in the second state than when the at least one bladder is in the first state, and wherein the fluid collection assembly exhibits a first cross-sectional shape when the at least one inflation element is in the first state and a second cross-sectional shape when the at least one bladder is in the second state, the first cross-sectional shape and the second cross-sectional shape measured perpendicular to a longitudinal axis of the fluid collection assembly.

20. A fluid collection assembly, comprising:

a fluid impermeable barrier defining a chamber, at least one opening, and at least one fluid outlet;

at least one porous material disposed in the chamber;

at least one inflation device including at least one bladder and at least one valve, the at least one bladder including one or more walls defining at least one interior region, the at least one valve configured to selectively permit at least one inflation fluid to flow into and out of the at least one interior region to switch the at least one bladder between a first state and at least a second state, wherein an amount of the at least one inflation fluid present in the at least one interior region is greater when the at least one bladder is in the second state than when the at least one bladder is in the first state, and wherein the fluid collection assembly exhibits a first width when the at least one inflation element is in the first state and a second width when the at least one bladder is in the second state, wherein the first width is less than the second width, the first width and the second width measured perpendicular to a longitudinal axis of the fluid collection assembly.

* * * * *